United States Patent
Takahashi et al.

(10) Patent No.: US 6,306,082 B1
(45) Date of Patent: Oct. 23, 2001

(54) STEREOENDOSCOPE WHEREIN IMAGES HAVING PASSED THROUGH PLURAL INCIDENT PUPILS ARE TRANSMITTED BY COMMON RELAY OPTICAL SYSTEMS

(75) Inventors: Susumu Takahashi, Iruma; Shinichi Nakamura, Hino; Tsutomu Takebayashi, Hachioji, all of (JP)

(73) Assignee: Olympus Optical Co., Tokyo (JP)

( * ) Notice: Subject to any disclaimer, the term of this patent is extended or adjusted under 35 U.S.C. 154(b) by 0 days.

(21) Appl. No.: 09/053,094

(22) Filed: Apr. 1, 1998

Related U.S. Application Data

(62) Division of application No. 08/404,890, filed on Mar. 16, 1995, now Pat. No. 5,743,846.

(30) Foreign Application Priority Data

| Mar. 17, 1994 | (JP) | ................................. H6-047189 |
| May 17, 1994 | (JP) | ................................. H6-603084 |
| Oct. 27, 1994 | (JP) | ................................. H6-264004 |

(51) Int. Cl.$^7$ ............................. A61B 1/04; A61B 1/055
(52) U.S. Cl. ................ 600/173; 600/111; 600/112; 600/166; 600/171; 600/176
(58) Field of Search ................................. 600/176, 166, 600/111, 173, 181, 109; 359/618, 639, 640, 725, 226, 656, 738–740, 419, 420, 372, 433; 348/45, 65

(56) References Cited

U.S. PATENT DOCUMENTS

| 3,889,662 | * | 6/1975 | Mitsui ............................. 600/173 |
| 4,279,247 | * | 7/1981 | Kinoshita ............................. 600/170 |
| 4,364,629 | | 12/1982 | Lang et al. . |
| 4,697,577 | * | 10/1987 | Forkner ............................. 600/173 |
| 4,838,247 | * | 6/1989 | Forkner ............................. 600/173 |
| 4,846,154 | * | 7/1989 | MacAnally et al. ................. 600/173 |
| 4,873,572 | | 10/1989 | Miyazaki et al. . |
| 5,122,650 | | 6/1992 | McKinley . |
| 5,282,085 | | 1/1994 | Volkert et al. . |
| 5,522,789 | | 6/1996 | Takahashi . |

FOREIGN PATENT DOCUMENTS

| 134370 | 3/1985 | (EP) . |
| 016812 | 1/1992 | (JP) . |

* cited by examiner

Primary Examiner—John P. Leubecker
(74) Attorney, Agent, or Firm—Armstrong, Westerman, Hattori, McLeland & Naughton, LLP.

(57) ABSTRACT

The illuminating light transmitted by the light guide inserted through the elongate inserted section is projected out of the distal end surface of the inserted section. The illuminated objects pass through the respective non-superimposed pupils of the two objective lens systems arranged in parallel within the distal end section of the inserted section and their images, which are not equal to each other are formed on the focal surface. The respective images are transmitted to the rear side by one common relay lens system having a single optical axis. The transmitted final images are formed respectively on the image taking surfaces of the image taking devices. The respective images photoelectrically converted by the respective image taking devices are processed to be signals, are displayed in the monitor and are stereo-inspected through shutter spectacles.

16 Claims, 51 Drawing Sheets

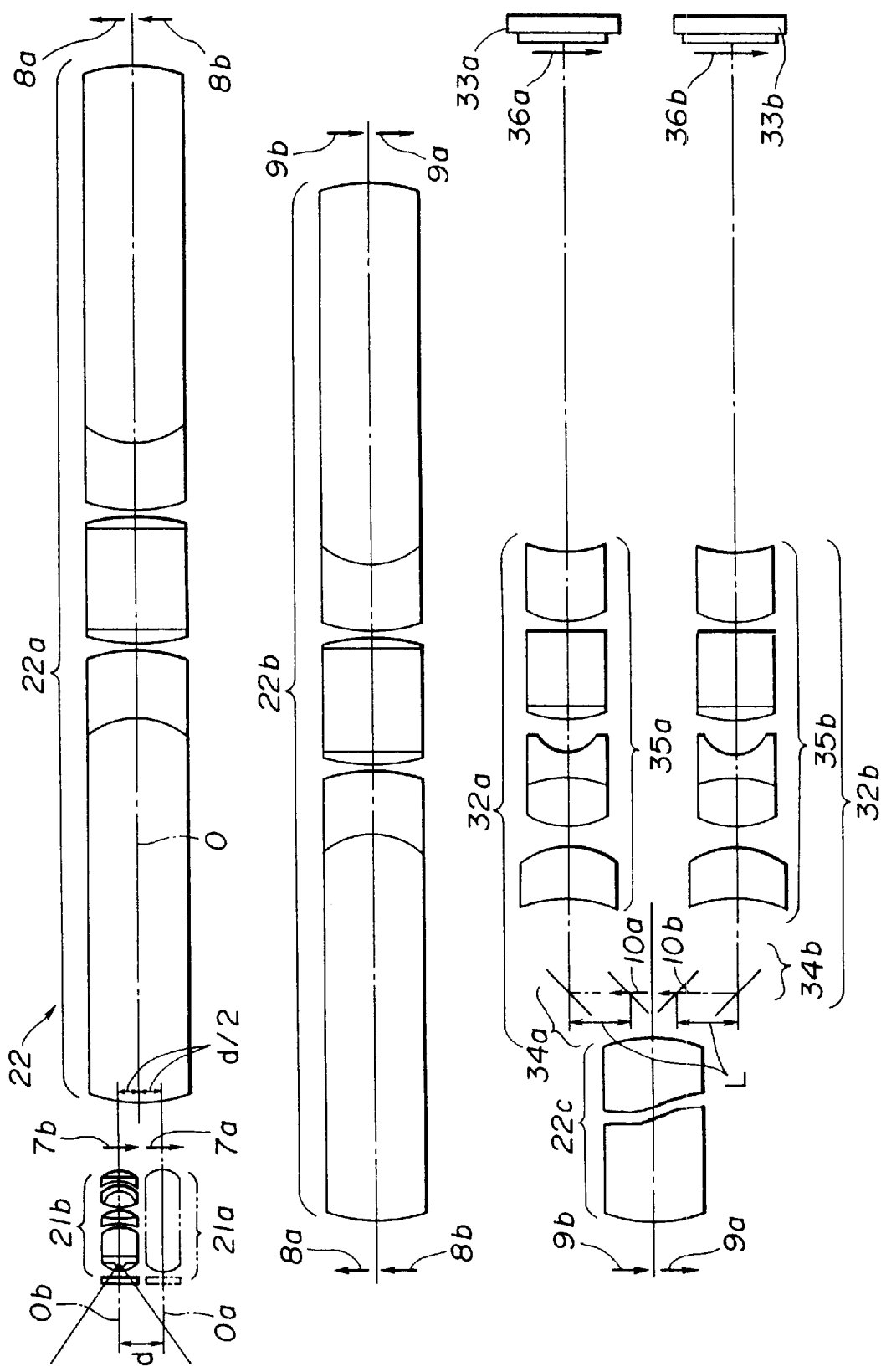

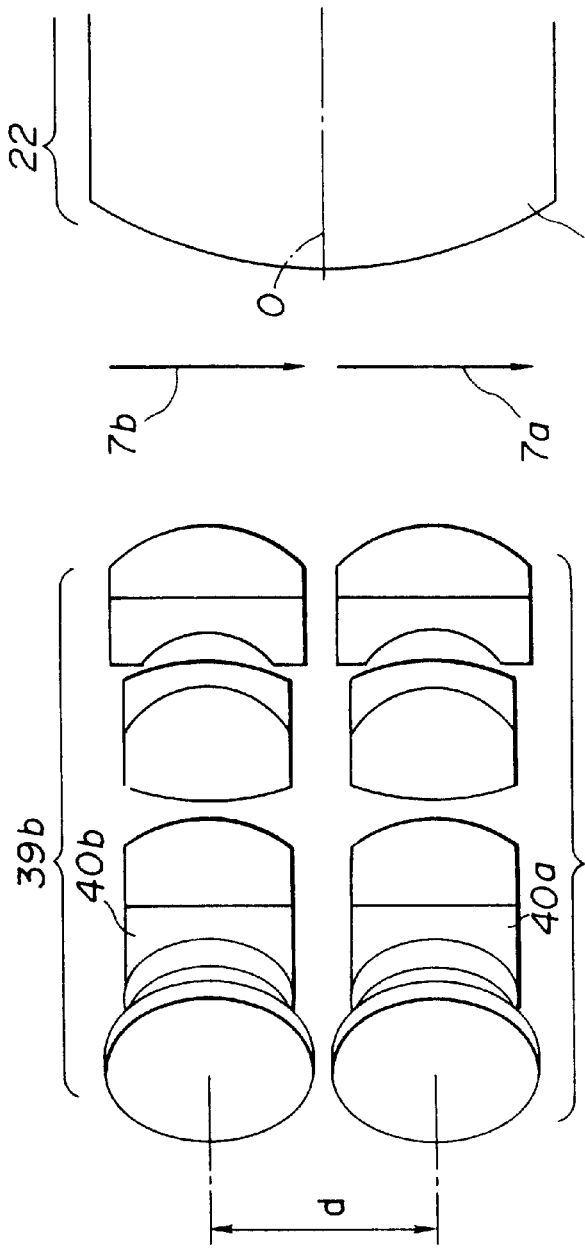
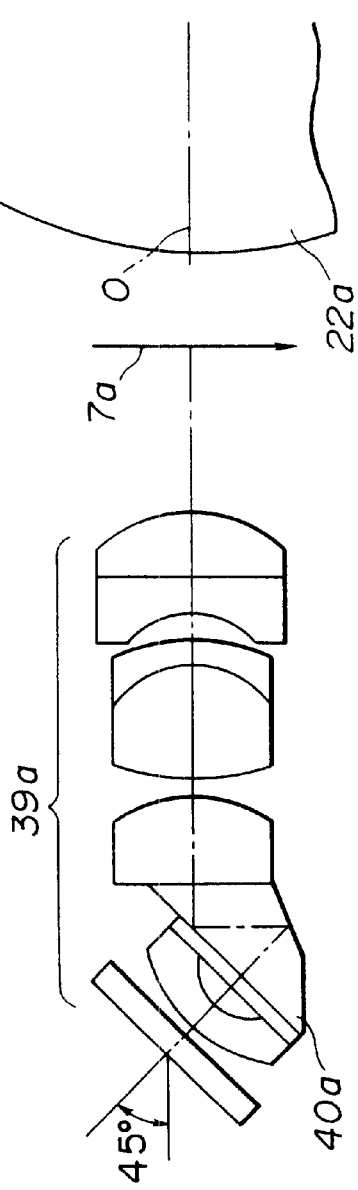
FIG.15A
FIG.15B

FIG.18 A
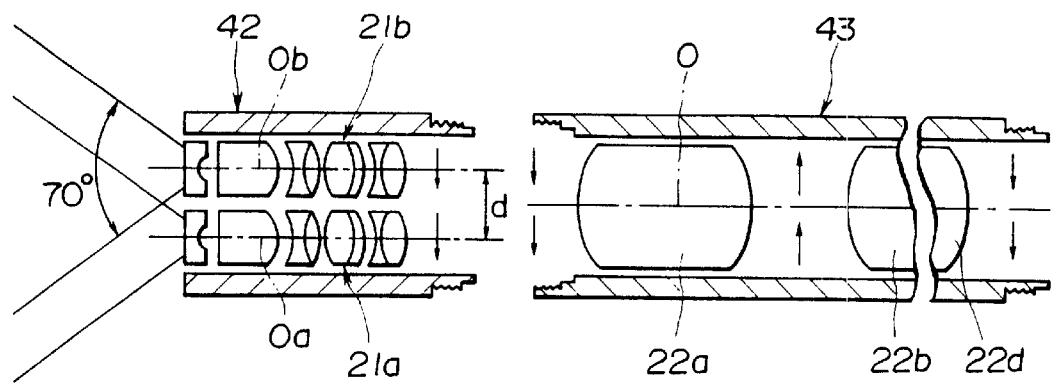
FIG.18 B
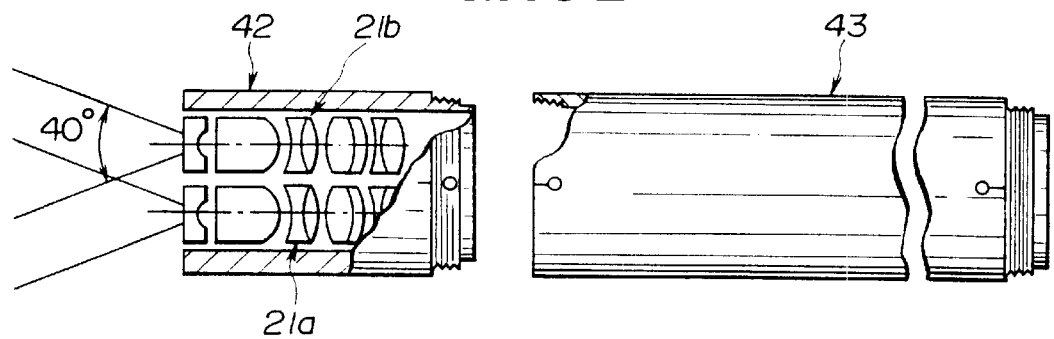
FIG.18 C     FIG.18 D
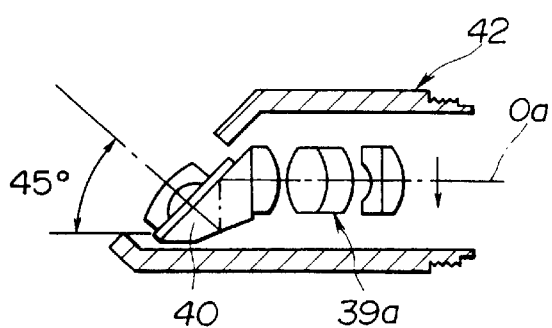 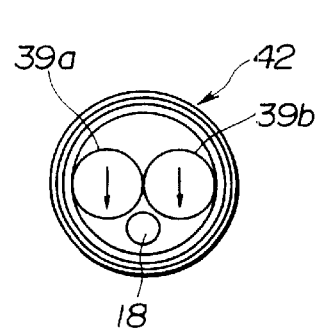
FIG.18 E
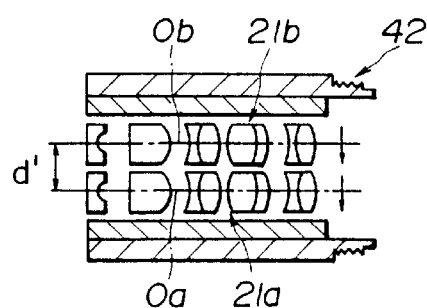

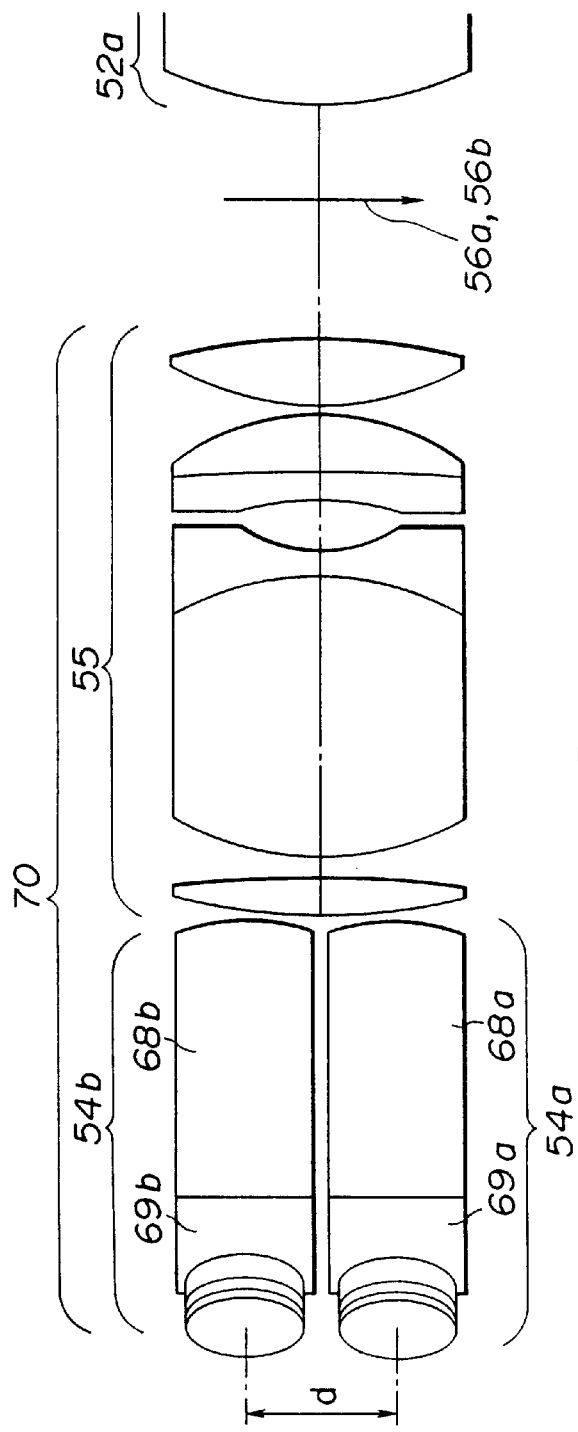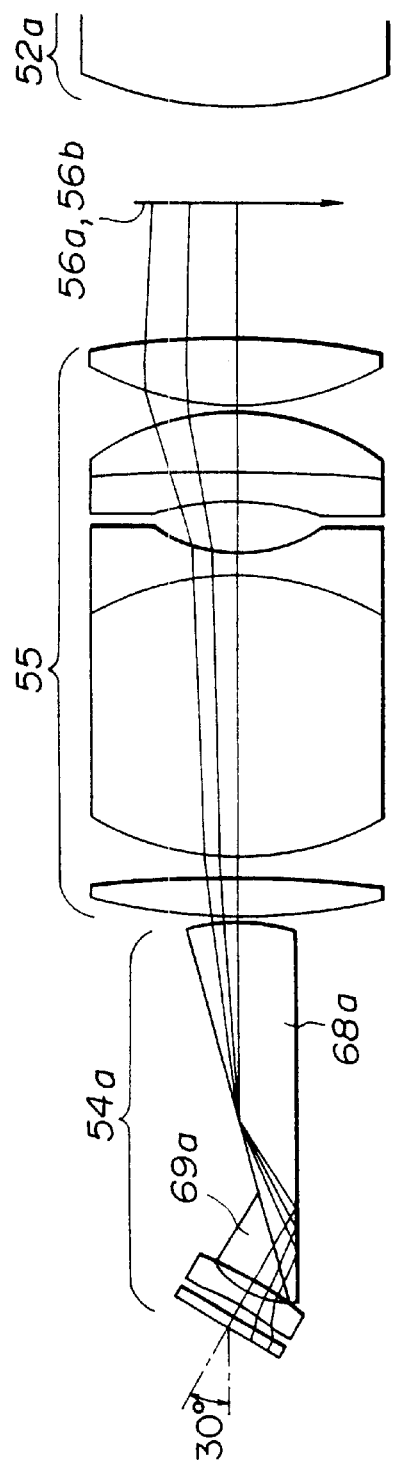
FIG.26A
FIG.26B

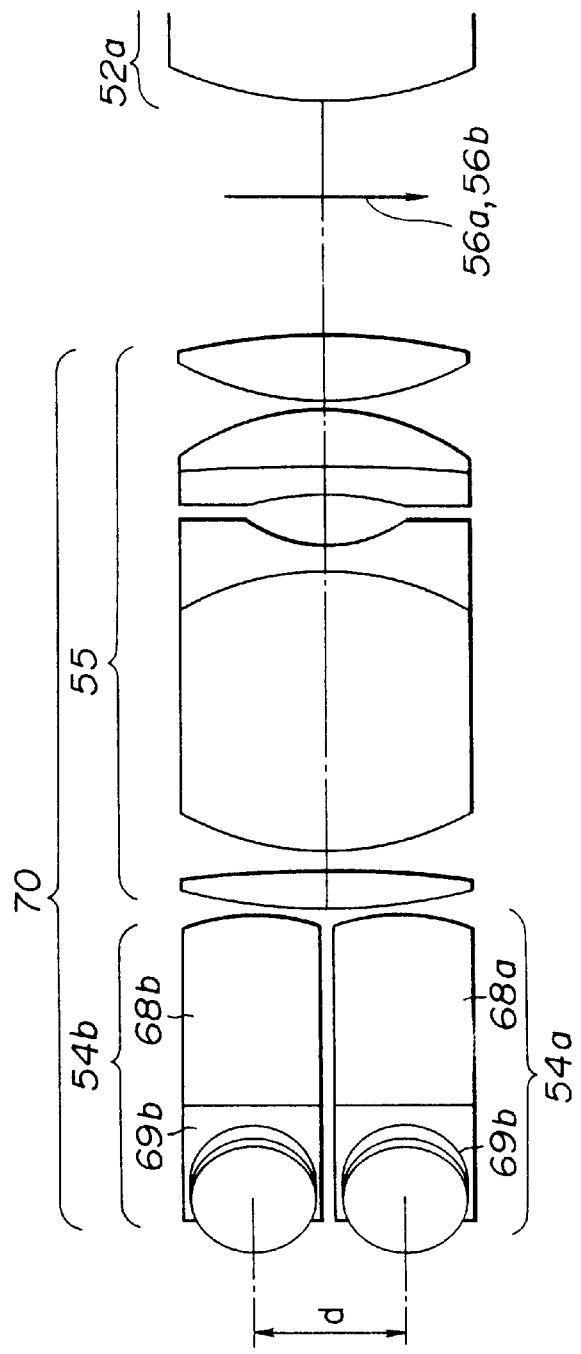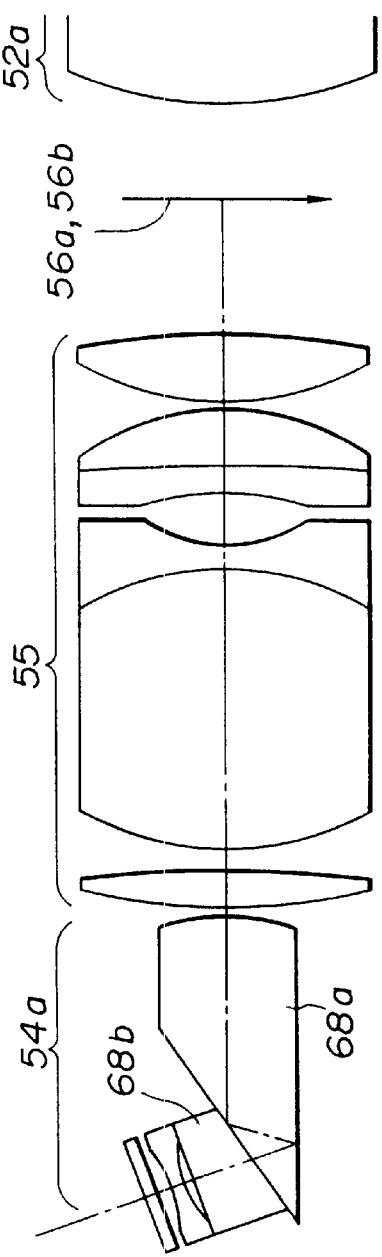

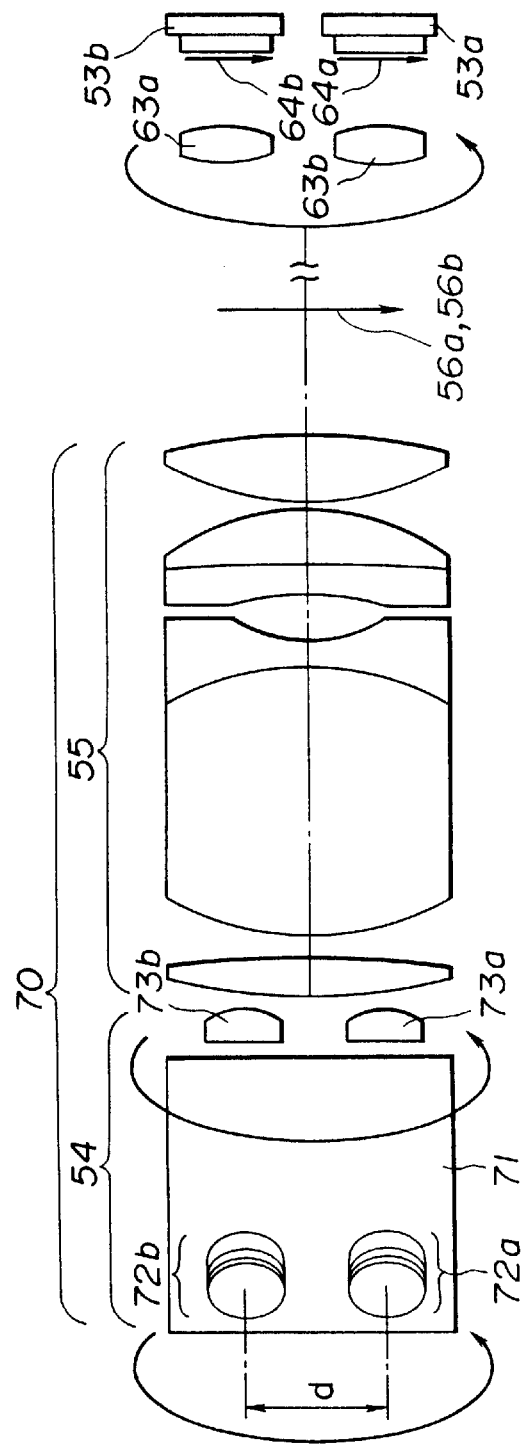
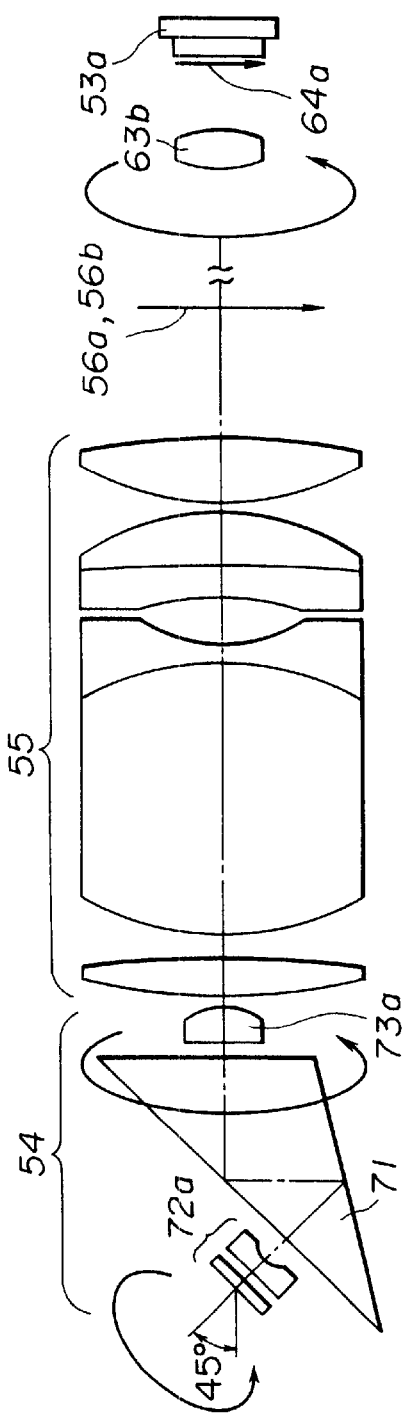
FIG. 28A
FIG. 28B

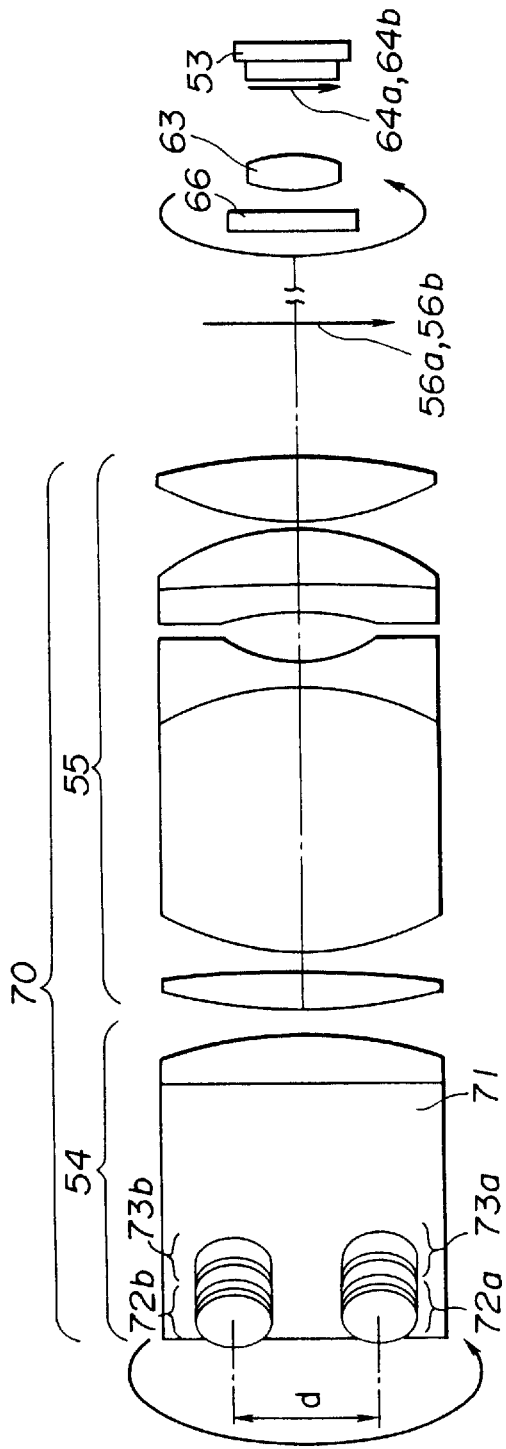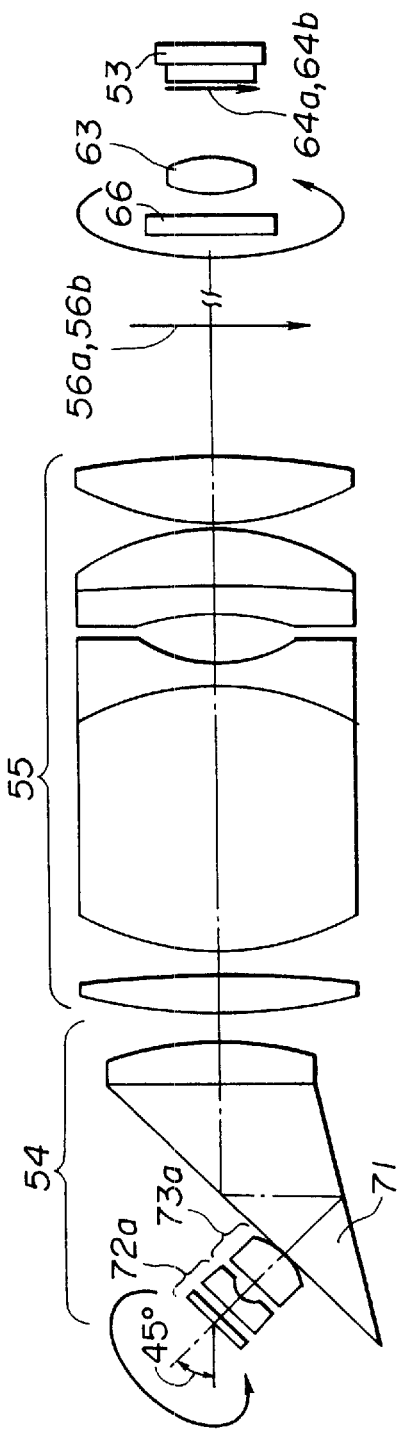

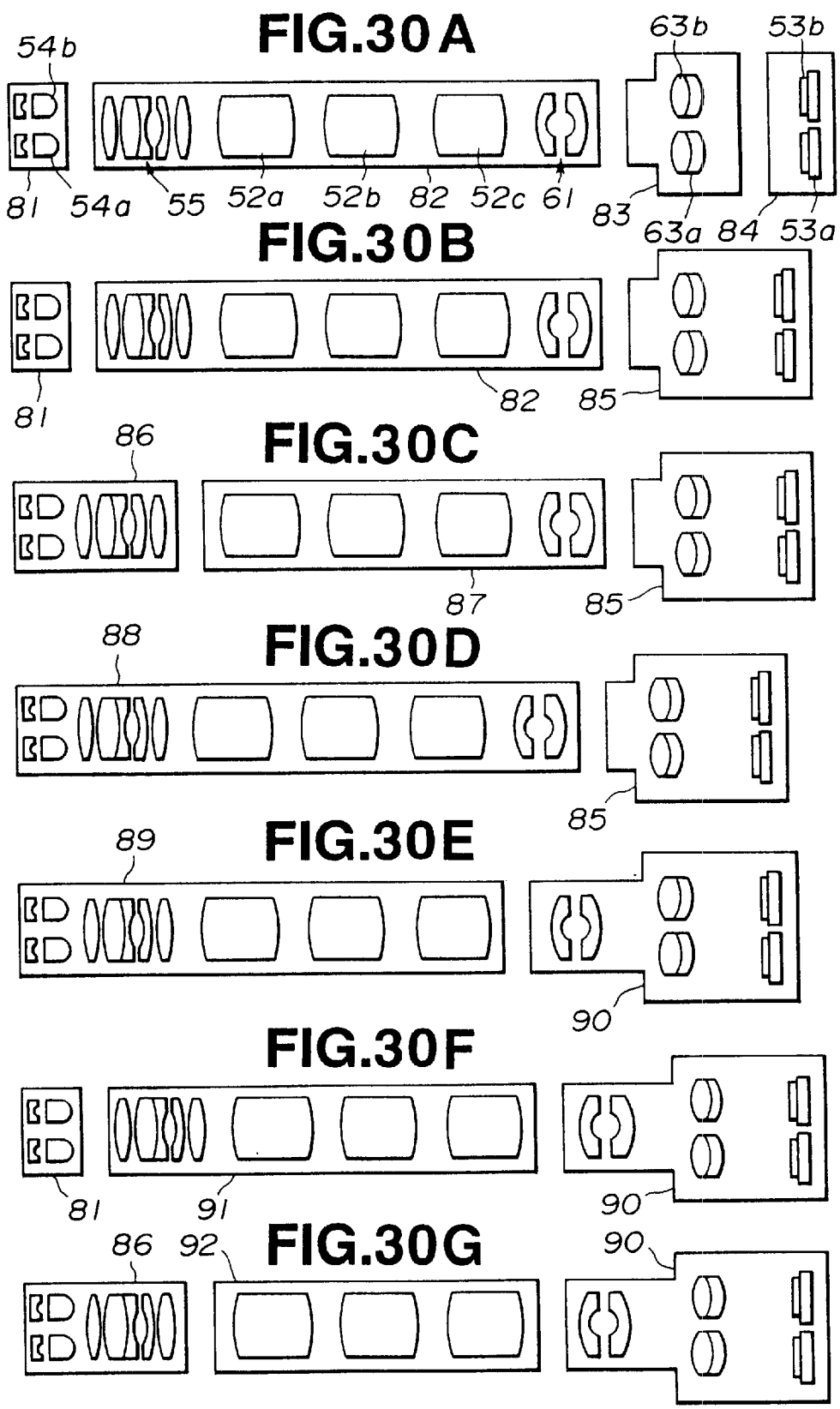

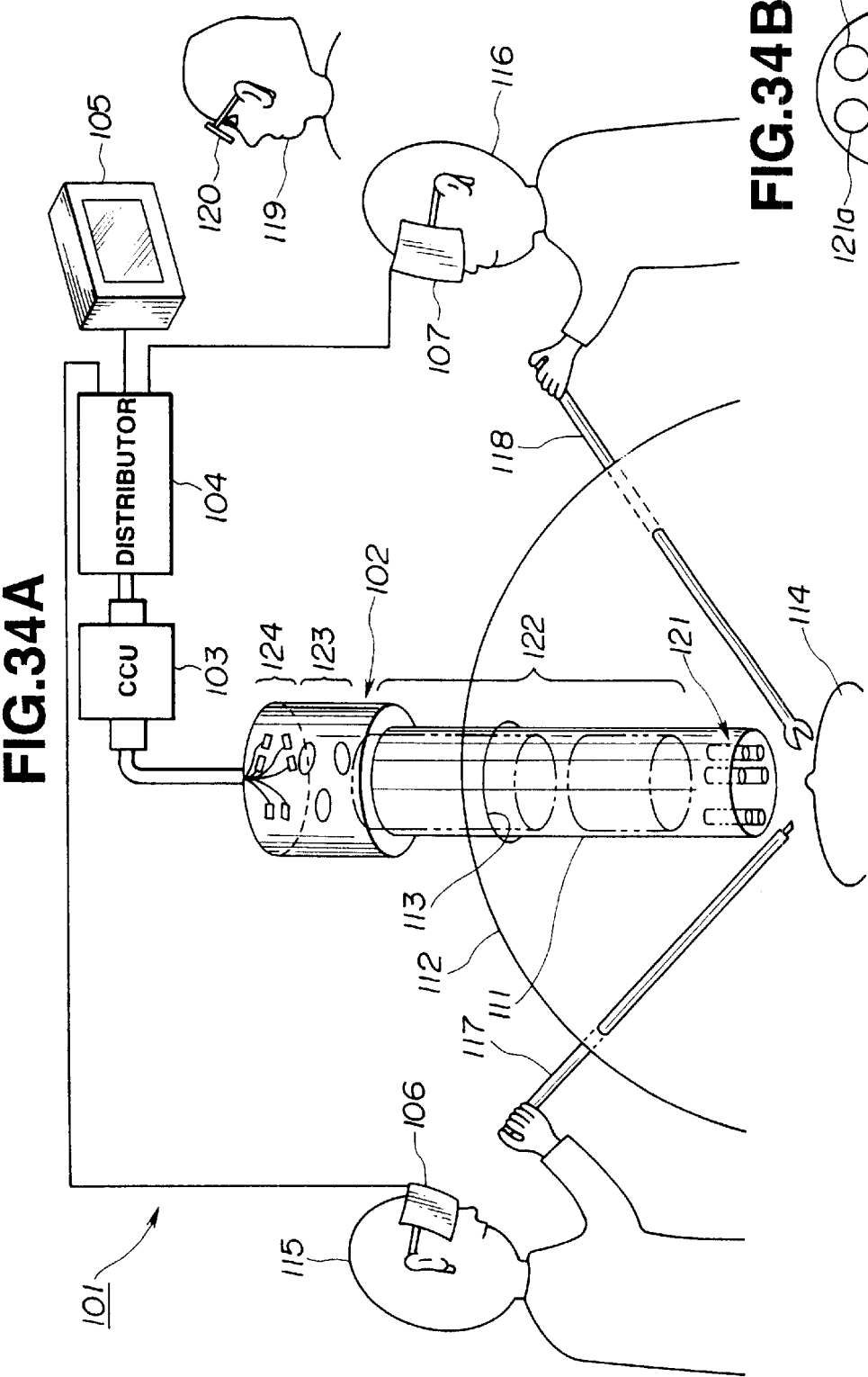
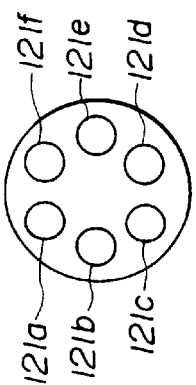
FIG. 34A
FIG. 34B

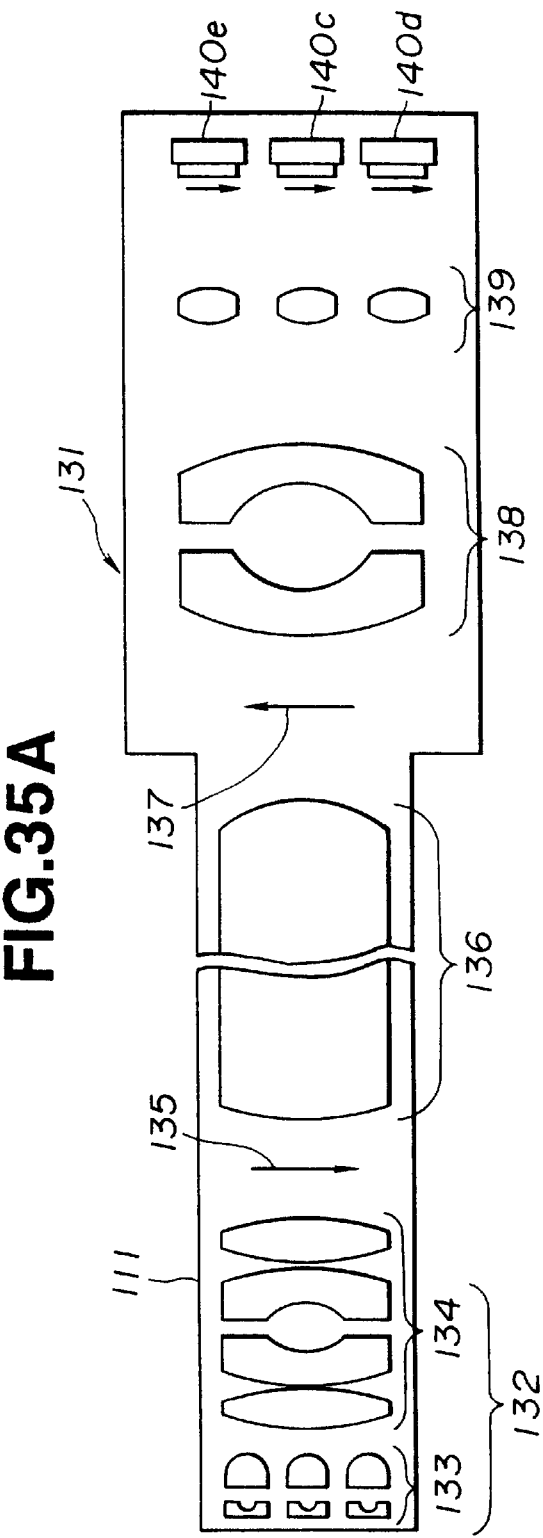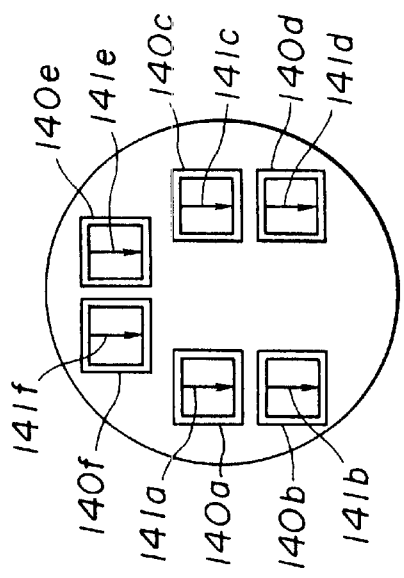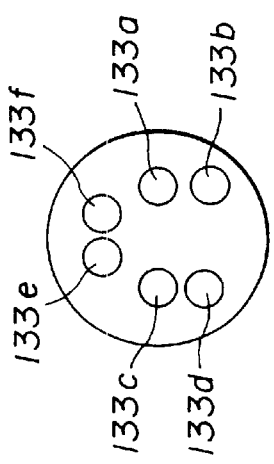
FIG.35A
FIG.35B
FIG.35C

FIG.36B     FIG.36A
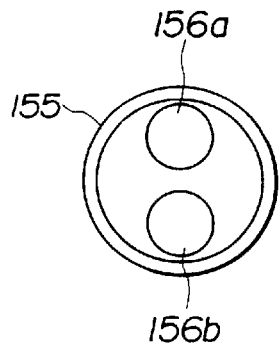
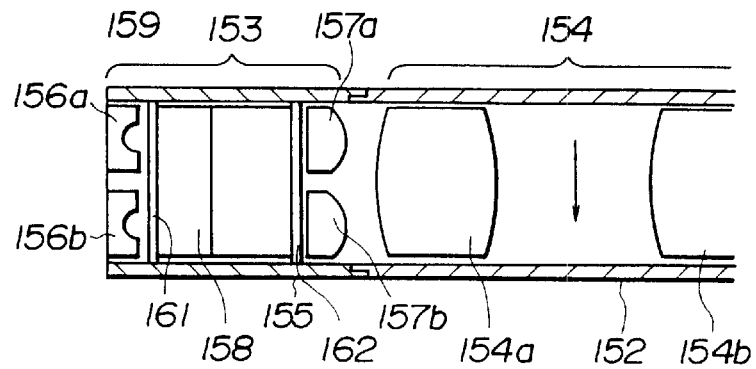
FIG.36D     FIG.36C
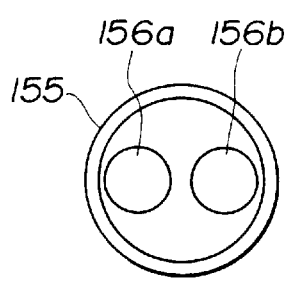
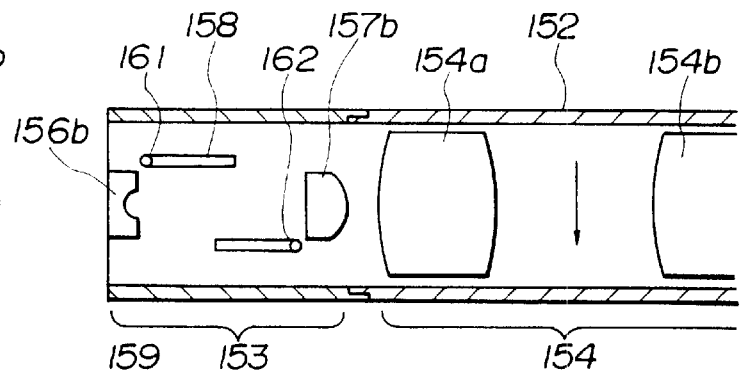
FIG.36F     FIG.36E
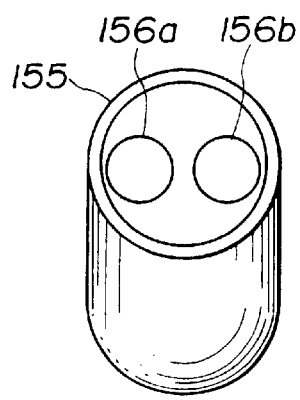
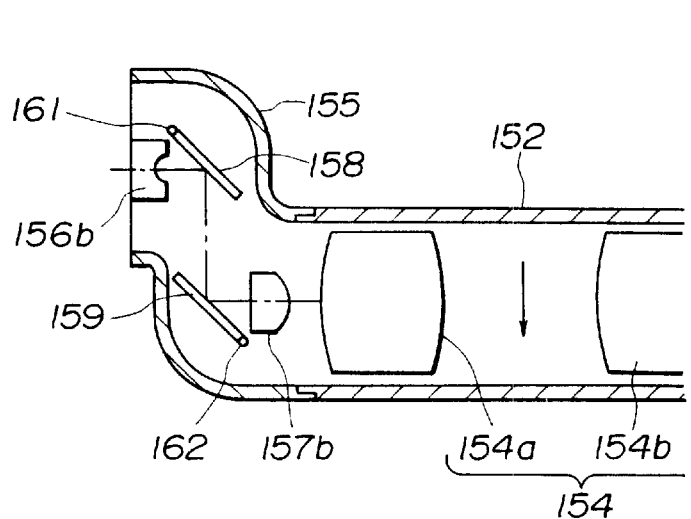

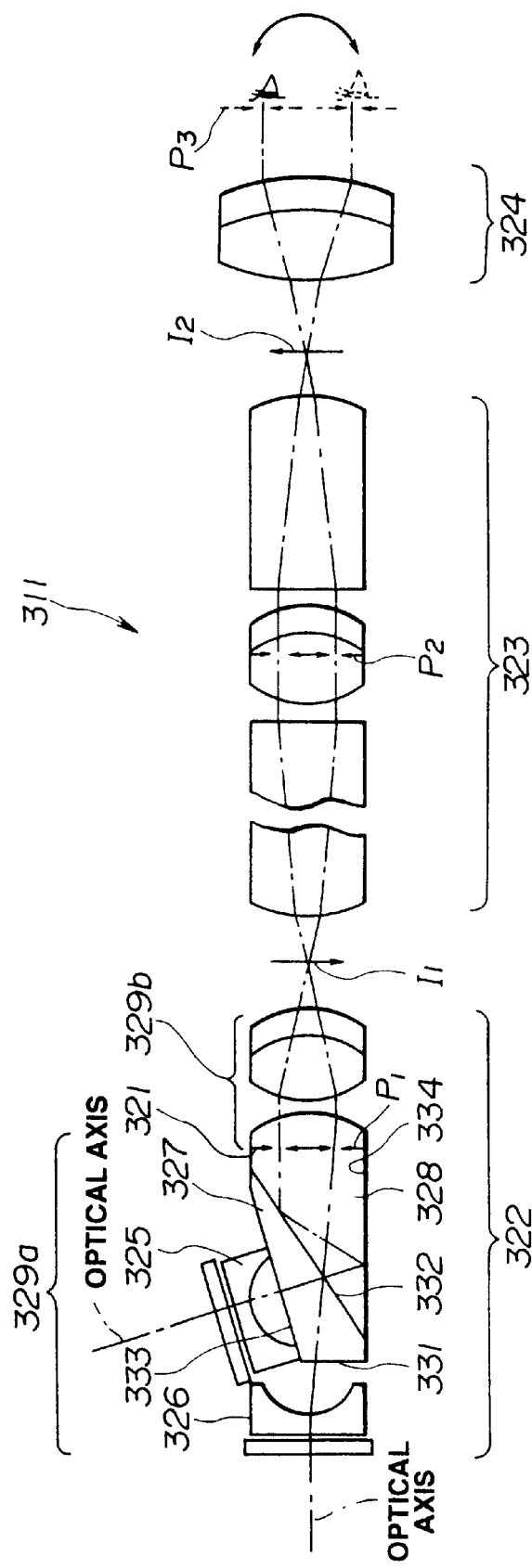

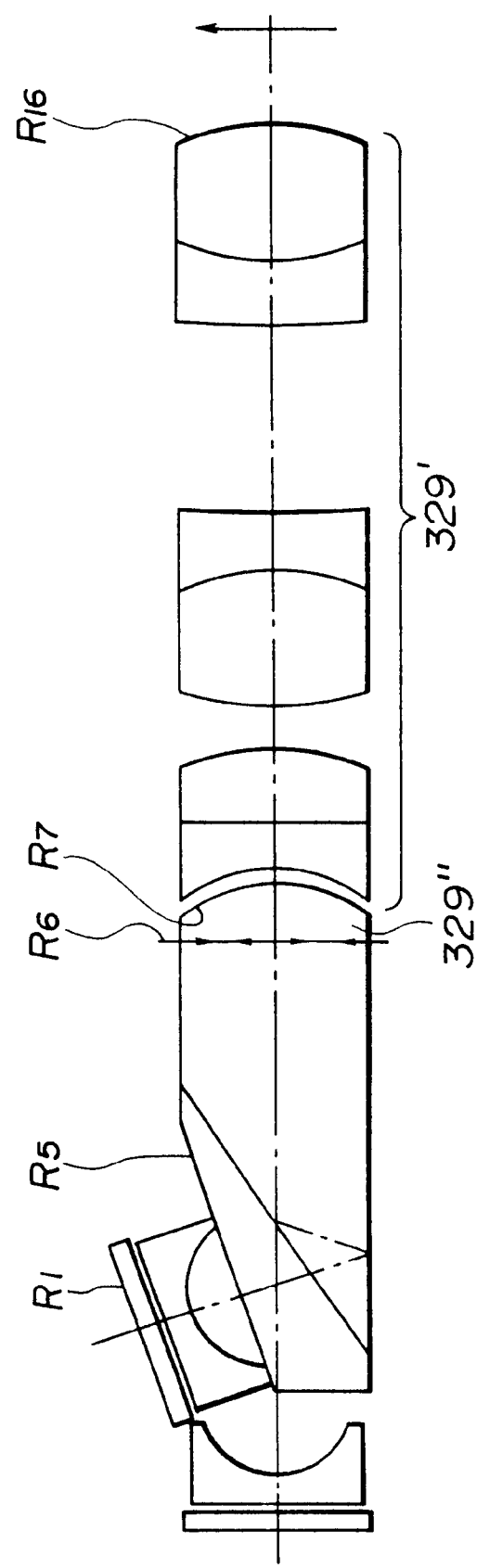

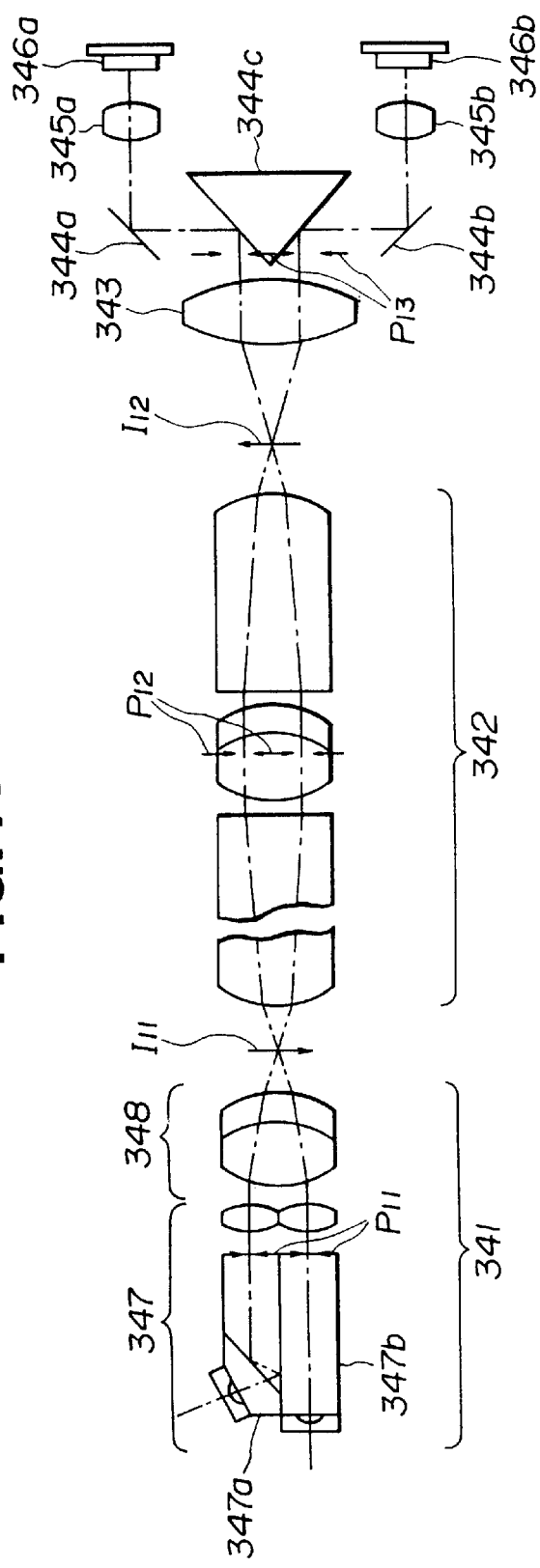
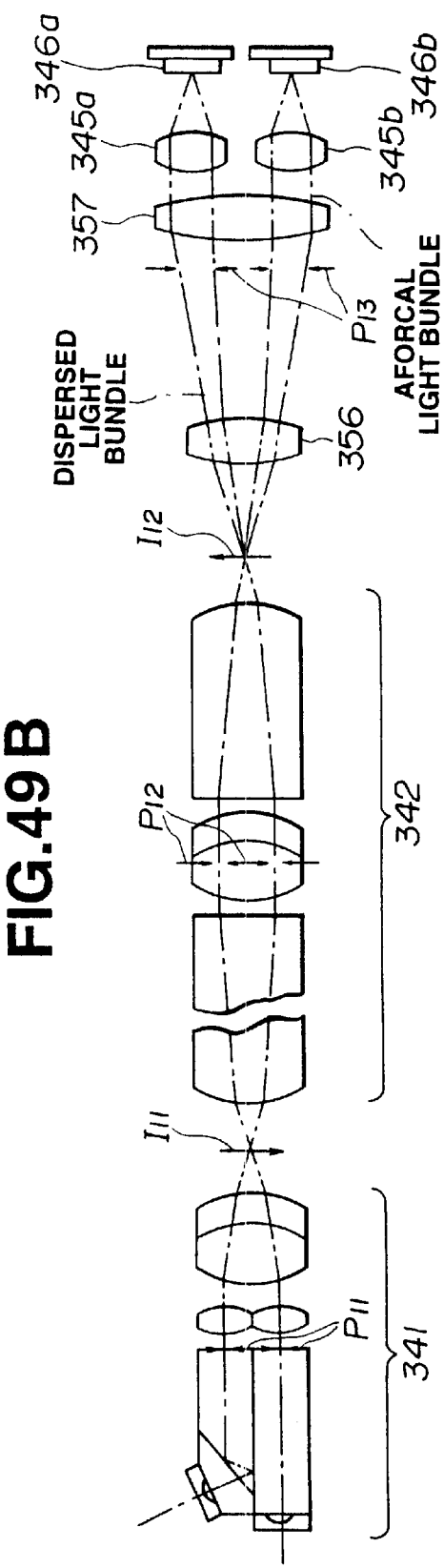
FIG.49A
FIG.49B

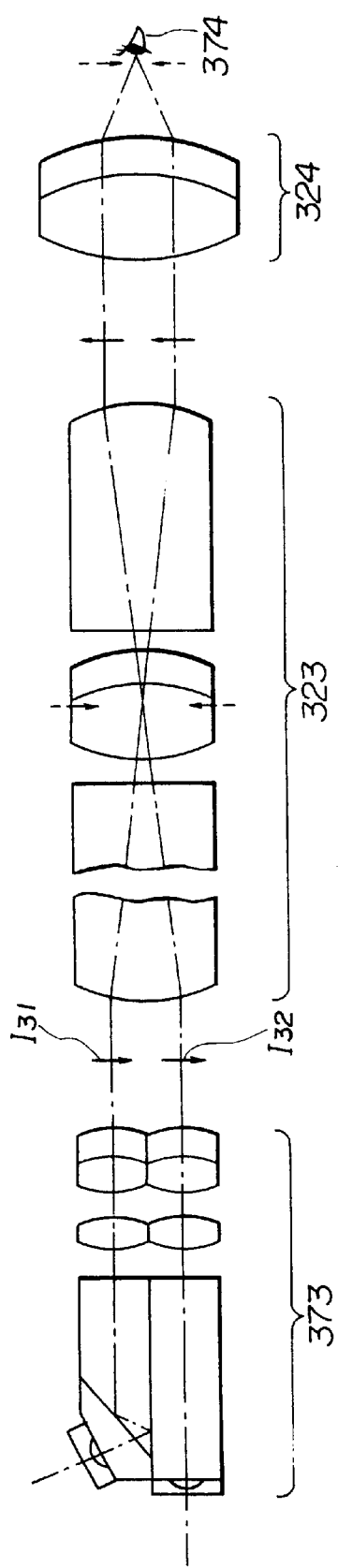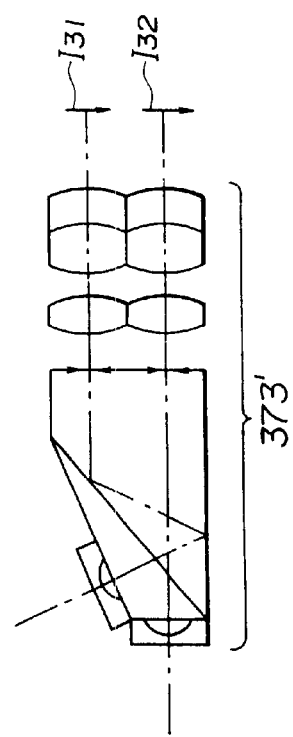
FIG.59A
FIG.59B

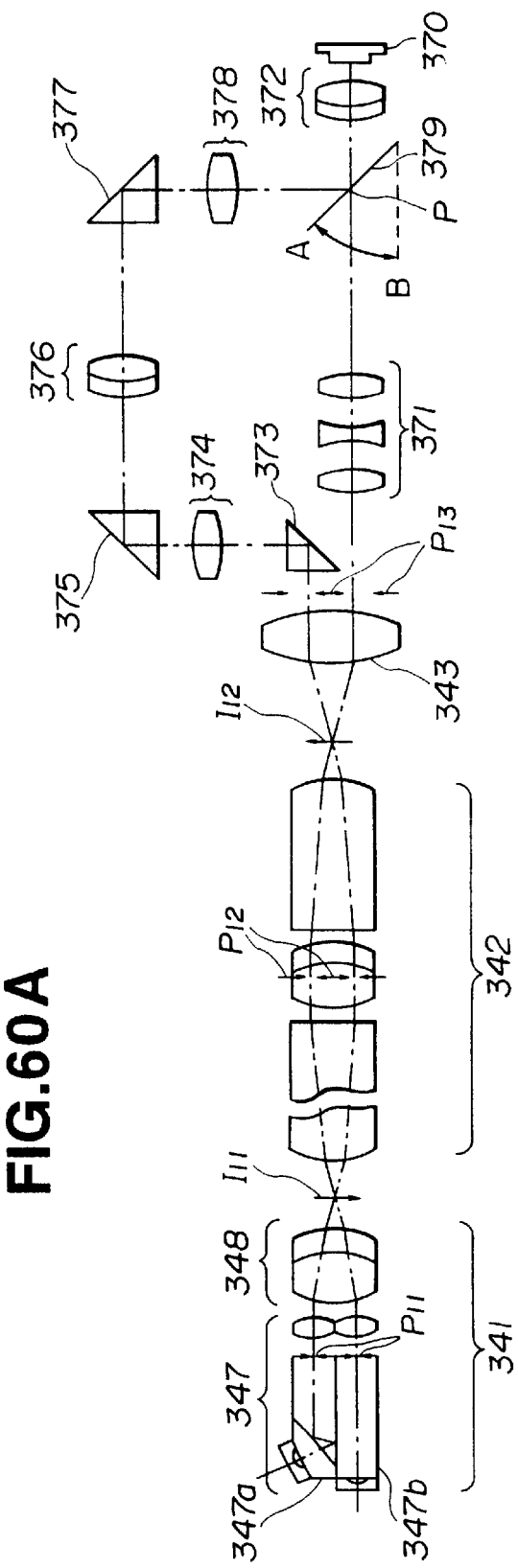
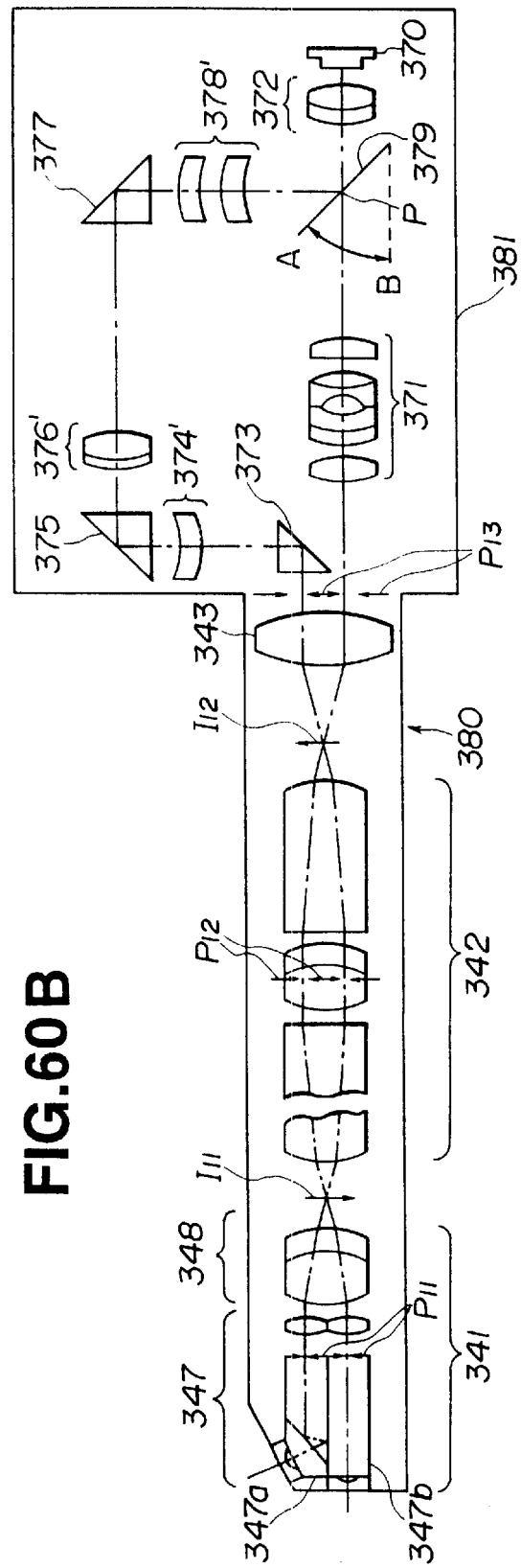
FIG.60A
FIG.60B

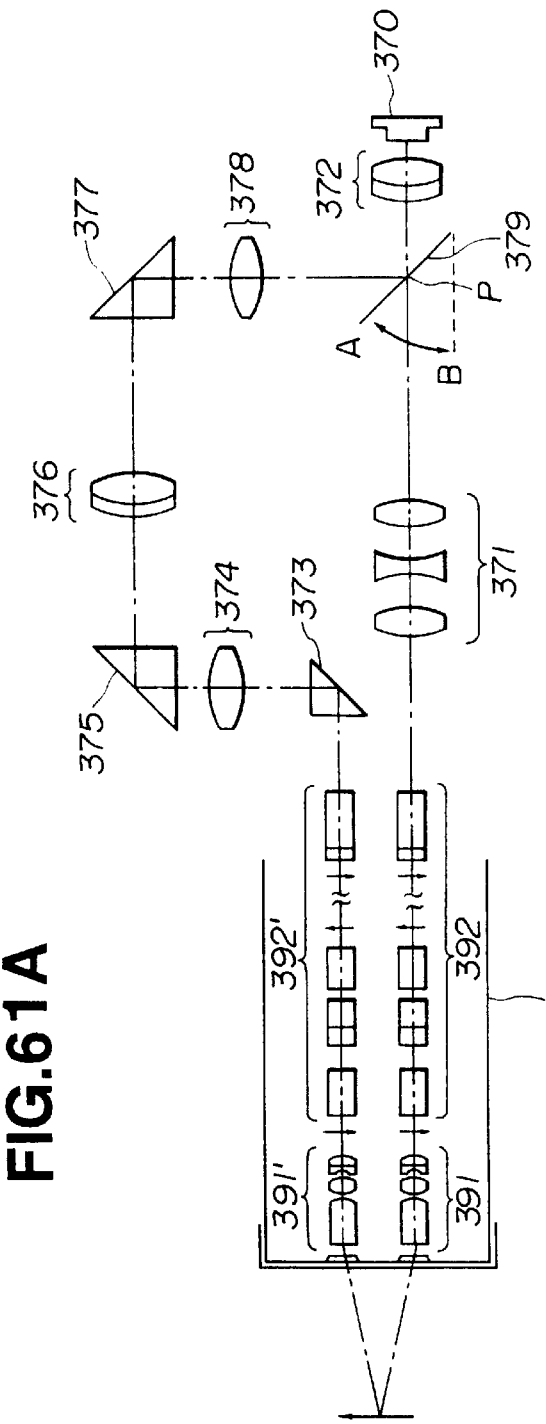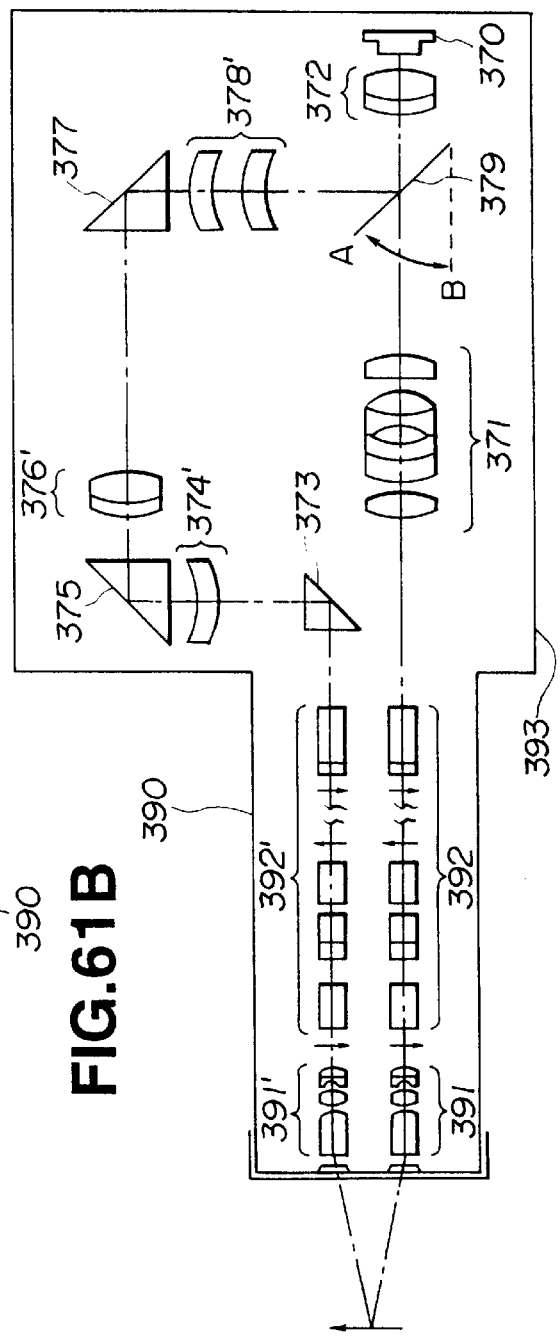
FIG.61A
FIG.61B

STEREOENDOSCOPE WHEREIN IMAGES HAVING PASSED THROUGH PLURAL INCIDENT PUPILS ARE TRANSMITTED BY COMMON RELAY OPTICAL SYSTEMS

This Appl is a Div. of Ser. No. 08/404,890 filed Mar. 16, 1995 U.S. Pat. No. 5,743,846.

BACKGROUND OF THE INVENTION

1. Field of the Invention

The present invention relates to a stereoendoscope wherein images having passed through plural incident pupils are transmitted by common relay optical systems so that an observation providing a stereo-feel may be possible.

2. Description of the Related Art

Recently, particularly in the surgical field, there is known a so-called endoscope operation wherein, in order to reduce the burden on the patient, without opening the abdomen, a small hole is made in the abdominal part, and an endoscope is inserted through the hole for the observation and treatment. In this field, the operation has been already made by directly and stereoscopically viewing the affected part with both eyes and therefore, even in the endoscope operation, stereo-inspection is strongly desired. If the stereo-inspection can be made, the operation will be easy, the operation time will be reduced and the hardship on the patient will be further reduced.

As a stereo-inspection endoscope whereby stereo-inspection is possible, there is a first related art example suggested in a Japanese patent application No. 309078/1992 shown in FIG. 1A wherein two identical optical systems are arranged in parallel and the images formed by the objective optical systems 401 and 401' are transmitted for a predetermined distance by the transmitting optical systems 402 and 402' (in this case, relay lens systems) and are taken by such image taking devices 403 and 403' as CCD's.

The taken pair of the right and left images are converted to electrical signals and are displayed in a TV monitor (not illustrated). At this time, when the displayed right and left images are switched at a high speed and simultaneously shutter spectacles synchronized with the images are used, the image for the right eye will be observed with the right eye and the image for the left eye will be observed with the left eye so as to be able to be stereo-inspected.

Also, as another type stereoendoscope, there is a second related art example suggested in a Japanese patent application No. 28278/1993 shown in FIG. 2A wherein the objective optical system 414 and the relay lens system 415 which is a transmitting optical system are formed of one axially symmetrical optical system. A prism 416 is arranged at the rear end of the relay lens system 415 and a pair of right and left images having a parallax are formed and taken in the image taking devices 417 and 417' by spatially dividing the pupil into two with the prism. FIGS. 1B and 2B on the left side of FIGS. 1A and 2A show respective incident pupils.

In order to make a stereo-inspection, it is necessary to obtain a pair of right and left images having a parallax from each other. Therefor, the incident pupil for the right image of the optical system and the incident pupil for the left image must be spatially separated. Also, the magnitude of the stereo-feel in the case of the stereo-inspection is proportional to the center distance between the right and left incident pupils.

In the two above-mentioned related art examples, in the case of the first type in which the same two optical systems are arranged, when the objective optical systems 401 and 401' to the image taking means 403 and 403' are separately formed and the left and right incident pupils 407 and 407' are separately positioned, images having a parallax from each other will be obtained. The center distance d between the left and right incident pupils 407 and 407' coincides with the optical axis distance D between the left and right objective optical systems 407 and 407'.

In the second type in which the pupil is divided among the above-mentioned related art, the objective optical system 414 and transmitting optical system 415 are formed of one axially symmetrical optical system and the pupil is one in this part but, when this one pupil is spatially divided into two by the pupil dividing means (in the above mentioned case, the pupil dividing prism) 416 and respective images are produced, images having a parallax from each other will be obtained. The center distance d between the left and right incident pupils 418 and 418' is ½ the size of the incident pupil 419 of the objective lens.

In the type in which the same two optical systems are arranged, as it is formed of separate right and left parts, the number of the parts is high, thereby increasing the difficulty in assembly. Also, the magnification difference between the right and left images due to the errors of the respective parts is large, the displacement of the focusing position is large, the normal stereo-inspection cannot be made and therefore a fine adjustment is necessary.

In the type of dividing pupil, there are advantages that the parts common to the right and left light paths are many, the number of parts is low and the displacement of the right and left images can be made small. On the other hand, when compared with the same thickness, the magnitude of the parallax will be smaller than in the first type and a sufficient stereo-feel will be difficult to obtain. That is to say, there is a problem in that the center distance between the right and left incident pupils is difficult to make large. This point shall be explained with reference to FIGS. 3A to 4B.

FIG. 3A is a magnified view of the objective optical system on the distal end side of the first related art example. FIG. 3B shows its incident pupil. Also, FIG. 4A is a magnified view of the objective optical system on the distal end side of the second related art example. FIG. 4B shows its incident pupil.

In the type in which the same two optical systems are arranged, that is, the first related art example, against the inside diameter $\Phi$ of the objective lens frame 421 of the endoscope distal end 420, the optical axis distance between the right and left objective optical systems is substantially $\Phi/2$. Therefore, the center distance between the right and left incident pupils 407 and 407' is also substantially $\Phi/2$.

On the other hand, in the type in which the pupil is divided, against the inside diameter $\Phi$ of the objective lens frame 421 at the endoscope distal end 420, the diameter of the incident pupil 419 of the objective optical system is smaller than $\Phi$, because the incident pupil of the objective optical system is smaller than the pupil of the relay lens system as the NA of the endoscope is limited by the outside diameter of the relay lens system and the picture angle of the objective optical system is larger than of the relay lens system.

Therefore, the center distance between the right and left incident pupils is less then $\Phi/2$ and is usually about $\Phi/6$ to $\Phi/10$. Therefore, in this type, the magnitude of the parallax is about ⅓ that in the above mentioned type. Particularly, when the distal end is thin, no sufficient stereo-feel will be obtained.

SUMMARY OF THE INVENTION

In view of such circumstances, an object of this invention is to provide a stereoendoscope wherein, as in the type in which the pupil is divided, the commonality of parts for the right and left light paths is made as high as possible, the variations of the right and left images by the production errors or the like can be made few and images having a stereo-feel by a parallax as great as of the type in which the same two optical systems are arranged are obtained.

The stereoendoscope of the present invention comprises an objective optical system which has a plurality of incident pupils formed in different positions and forms a plurality of images passing through the incident pupils and having a parallax from each other and a common image transmitting optical system which transmits the plurality of images having a parallax from each other.

When thus formed, as the objective optical system has a plurality of independent incident pupils, irrespective of the size of the diameter of the incident pupil of the objective optical system, the parallax will be able to be made large. Also, as the plurality of images and pupils are not separately transmitted by the plurality of transmitting systems but are transmitted by the common image transmitting optical system, the number of parts will be able to be reduced. Even if a production error is present in the individual image transmitting optical system, as the images are transmitted by the common image transmitting system, the variation between the plurality of transmitted images will be able to be reduced.

In order to realize such formation, there are the following two systems (a) and (b):

(a) A formation comprising an objective optical system which forms a plurality of images having parallaxes in spatially separated positions and one image transmitting optical system which transmits the plurality of incident pupils and the plurality of images of the object optical system so that the images transmitted by this image transmitting optical system may be taken finally by one or more image taking means. More specifically, the system includes:

A stereoendoscope having an objective optical system, image transmitting optical system and image taking device, where the objective optical system comprises a plurality of optical systems arranged in parallel and forms a plurality of images having a parallax from each other and the image transmitting optical system comprises an optical system arranged along one optical axis and transmits a plurality of images formed by the objective optical system.

In this formation, as the operation common to (a) and (b) is made and the image transmitted by the image transmitting optical system is also spatially separated, the image can be stereo-inspected through an image taking means taking images or an ocular optical system making observation with the naked eyes. The image taking means can use one or more image taking devices and can take a plurality of images transmitted and spatially separated by the transmitting optical system and stereo-inspection is thereby possible.

The other formation realizing such formation is as follows:

(b) A formation comprising an objective optical system forming a plurality of images having parallaxes where they spatially substantially coincide (superimposed), jetting pupils corresponding to the plurality of incident pupils of the objective optical system and one image transmitting optical system transmitting the plurality of images, wherein the images transmitted by the image transmitting optical system are taken finally by one or more image taking means.

More specifically, the system includes:

A stereoendoscope having an objective optical system, image transmitting optical system and image taking device, where the objective optical system comprises a plurality of front group optical systems arranged in parallel to take in a plurality of images having a parallax from each other and rear group optical systems arranged so as to be on the same optical axis as of the image transmitting optical system and forming images of beams from the plurality of front group optical systems where the beams are substantially superimposed. The image transmitting optical system transmits the plurality of images formed by the rear group optical systems, having a parallax from each other and substantially superimposed. The jetting pupils of the objective optical system.

In this formation, because a common operation is made and images having parallaxes are transmitted to be formed where they are substantially superimposed, the diameter of the relay optical system can be made small.

BRIEF DESCRIPTION OF THE DRAWINGS

FIG. 1A is a formation view showing its stereoendoscope and FIG. 1B is an explanatory view showing incident pupils.

FIG. 2A is a formation view showing its stereoendoscope and FIG. 2B is an explanatory view showing an incident pupil.

FIG. 5 is a formation view showing the whole of a stereoendoscope apparatus provided with the first embodiment.

FIG. 6 is a formation view showing an image taking optical system in the stereoendoscope of the first embodiment of the present invention.

FIG. 10A is an explanatory view showing images formed by an objective optical system and relay optical system and a final image by the image transmission and FIG. 10B is an explanatory view showing the arrangement of a final image and an image taking device arranged in the position in case the objective optical system and relay optical system of FIG. 10A are used.

FIG. 11 is a formation view showing an image taking optical system in the fourth embodiment of the present invention.

FIGS. 15A and 15B relate to the eighth embodiment of the present invention, where FIG. 15A is a plan view showing an objective optical system and FIG. 15B is a side view showing the objective optical system.

FIG. 16A is a plan view showing a unit formation of the ninth embodiment and FIG. 16B is a side view of FIG. 16A.

FIG. 16C is a plan view showing a unit formation of the first modification and FIG. 16D is a side view of FIG. 16C as an ocular adapter is connected.

FIGS. 18A to 18E are views respectively showing formations of objective optical system units.

FIG. 23A is a sectioned plan view and FIG. 23B is a side view as seen from the side of FIG. 23A. FIGS. 23C and 23D are respectively a front view and back view as seen from the front surface and back surface sides.

FIGS. 26A and 26B show an objective optical system in the fifteenth embodiment of the present invention, where FIG. 26A is a plan view and FIG. 26B is a side view.

FIGS. 27A and 27B show an objective optical system in a modification of the fifteenth embodiment, where FIG. 27A is a plan view and FIG. 27B is a side view.

FIGS. 28A and 28B show an image taking optical system in the sixteenth embodiment, where FIG. 28A is a plan view and FIG. 28B is a side view.

FIGS. 29A and 29B show an image taking optical system in the seventeenth embodiment, where FIG. 29A is a plan view and FIG. 29B is a side view.

FIGS. 30A to 30G are explanatory views respectively showing unit formations of the eighteenth embodiment.

FIGS. 33A to 32D are sectioned views respectively showing formations of rear group and relay lens system units.

FIGS. 34A and 34B relate to the nineteenth embodiment of the present invention, where FIG. 34A is a general formation view of a stereoendoscope apparatus provided with the nineteenth embodiment and FIG. 34B is a view of the arrangement of an objective optical system on the distal end surface of the stereoendoscope of the nineteenth embodiment.

FIGS. 35A to 35C relate to the twentieth embodiment of the present invention, where FIG. 35A is a view showing the formation of a stereoendoscope of the twentieth embodiment, FIG. 35B is an elevation showing the arrangement of an objective optical system as seen from the distal end surface and FIG. 35C is an explanatory view showing the arrangement of an image taking device as seen from the distal end side.

FIGS. 36A to 36F show the formation on the distal end side of the twenty-first embodiment of the present invention, where FIG. 36A is a vertically sectioned view; FIG. 36B is an elevation of FIG. 36A;

FIG. 36C is a horizontally sectioned view;

FIG. 36D is an elevation of FIG. 36B;

FIG. 36E is a horizontally sectioned view; and

FIG. 36F is an elevation of FIG. 36F.

FIG. 37A is a vertically sectioned view and FIG. 37B is an elevation of FIG. 37A.

FIG. 38A is a formation view showing the formation of an objective optical system in a stereoendoscope of the prior example and FIG. 38B is an explanatory view of a power arrangement for the objective optical system of FIG. 38A.

FIG. 39 is a general formation view of a stereoendoscope apparatus provided with the twenty-third embodiment;

FIG. 40 is a formation view of an image taking optical system including the objective optical system in the stereoendoscope of the twenty-third embodiment;

FIG. 41 is an explanatory view of a power arrangement of the objective optical system of FIG. 40; and FIG. 42 is a sectioned view showing a frame structure at the distal end of the stereoendoscope in FIG. 39.

FIGS. 46 to 48 relate to the twenty-sixth embodiment, where FIG. 46 is a general formation view of an endoscope apparatus;

FIG. 47A is a formation view of a plural of visual field direction type endoscope;

FIG. 47B is a view showing the formation of a brightness diaphragm; and

FIG. 48 is a formation view of an objective optical system utilizing a pupil division.

FIGS. 49A to 54 relate to the twenty-seventh embodiment, where FIG. 49A is a formation view of a plural visual field direction type endoscope including an objective optical system utilizing an eccentric optical system; FIG. 49B is a formation view of an endoscope relating to a modification of the twenty-seventh embodiment;

FIG. 50 is a formation view of an objectiveoptical system in which an eccentric optical system is utilized and an afocal part is partly in common;

FIG. 51 is a formation view of an objective optical system in which an eccentric optical system is utilized and a perspective is made by refraction;

FIG. 52 is a formation view of a design of an objective optical system in which an eccentric optical system is utilized;

FIG. 53 is a formation view of a design in which a relay lens system is combined with an objective optical system; and FIG. 54 is an elevation of an objective optical system having three visual field directions.

FIGS. 55 to 58 relate to the twenty-eighth embodiment, where FIG. 55 is a formation view of a plural visual field direction type endoscope having a pupil switching apparatus;

FIG. 57 is a formation view of a plural visual field direction type endoscope in which the visual field direction can be switched by the movement of a solid state image taking device or the like;

FIG. 58A is a formation view of a plural visual field direction type endoscope in which a pupil switching apparatus is provided near the pupil of an objective optical system; and FIG. 58B is a formation view of a plural visual field direction type endoscope different from that of FIG. 58A.

FIG. 59A is a formation view of a plural visual field direction type endoscope relating to the twenty-ninth embodiment. FIG. 59B is a formation view of an endoscope in which the objective optical system is made partly common.

FIG. 60A is a formation view of an optical system of a plural visual field direction type endoscope of the thirtieth embodiment.

FIG. 60B is a formation view of an optical system of a plural visual field direction type endoscope of a modification of the thirtieth embodiment.

FIG. 61A is a formation view of an optical system of a plural visual field direction type endoscope of the thirty-first embodiment.

FIG. 61B is a formation view of an optical system of a plural visual field direction type endoscope of a modification of the thirty-first embodiment.

DESCRIPTION OF THE PREFERRED EMBODIMENTS

The present invention shall be explained as follows with reference to the drawings.

The stereoendoscope in each of the first to the twenty-second embodiments is characterized by having an objective optical system which has a plurality of incident pupils formed in different positions and forms a plurality of images having passed through these incident pupils and having a parallax from each other and a common image transmitting optical system which transmits the plurality of images having a parallax from each other.

Each of the first embodiment to the modification of the ninth embodiment is of the formation (a). That is to say, images having a parallax from each other are formed in separated positions by a plurality of objective optical systems arranged at the distal end of an endoscope and the images separated from each other are transmitted by one common image transmitting optical system.

Figure 5:
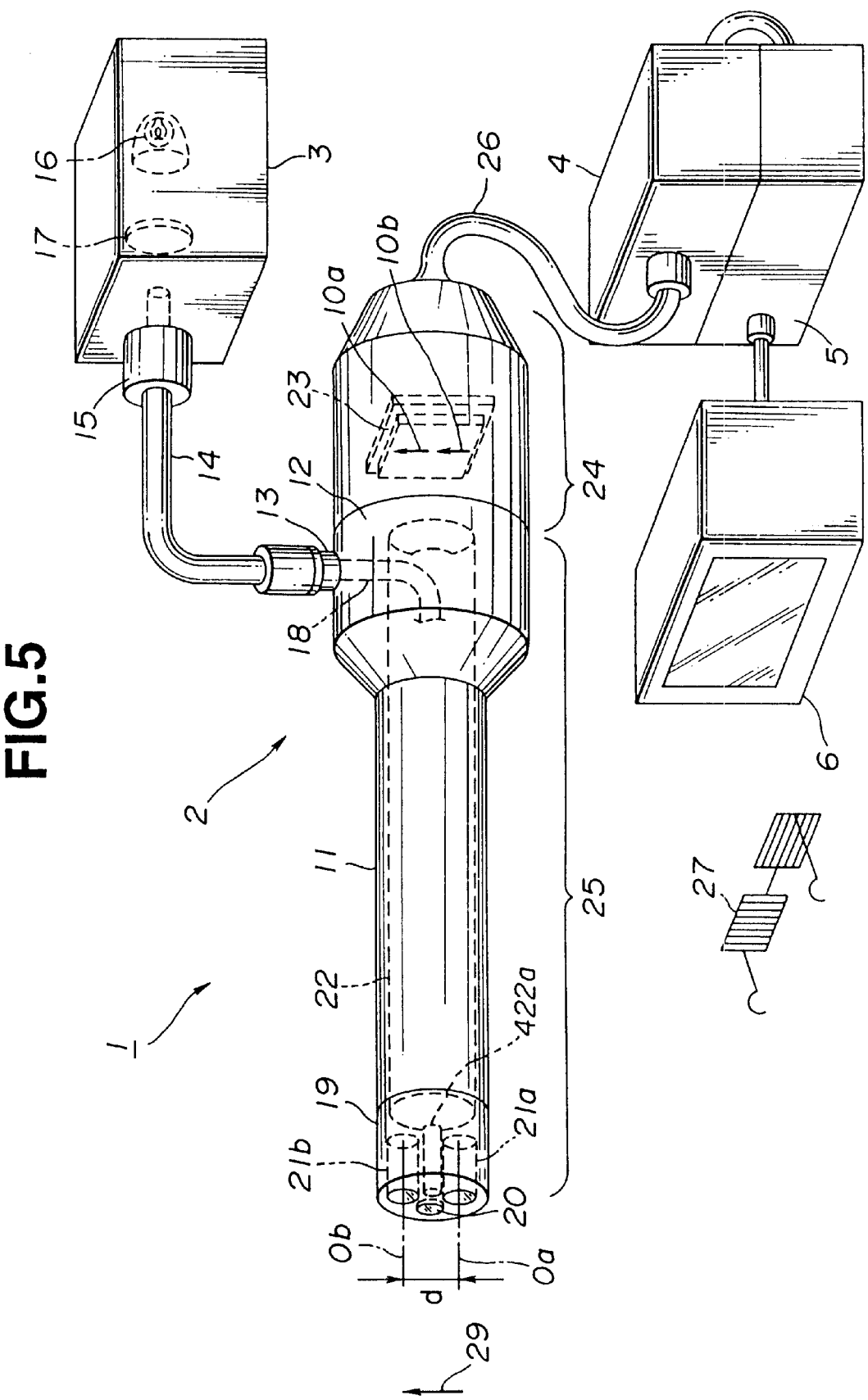
FIGS. 5 and 6 relate to the first embodiment of the present invention, where

As shown in FIG. 5, a stereoendoscope apparatus 1 comprises a stereoendoscope 2 of the first embodiment having an image taking optical system for stereo-inspection built-in, a light source apparatus 3 feeding an illuminating light to an illuminating light transmitting means provided in this stereoendoscope to transmit the illuminating light, a camera controlling unit (abbreviated as a CCU hereinafter) 4 processing signals for an image taking means built-in in this stereoendoscope 2, a scan converter 5 converting the signal from this CCU 4 to a video signal, a color monitor 6 displaying the video signal put out of this scan converter 5 and shutter spectacles 27 having a shutter function for stereo-inspecting the image displayed in this color monitor 6.

The stereoendoscope 2 has an elongate inserted section 11 to be inserted into a body cavity or the like and a gripped section formed to be large in the diameter at the proximal end of this inserted section so as to be gripped by the operator. This inserted section 11 is formed of a cylindrical rigid jacket tube made of metal such as stainless steel. That is to say, this stereoendoscope 2 is a rigid endoscope having the rigid inserted section 11.

As is an ordinary endoscope, this stereoendoscope has an illuminating light transmitting means transmitting the illuminating light fed from the light source apparatus 3, an illuminating optical system projecting this transmitted illuminating light out of an illuminating window and illuminating the object side and an observing optical system obtaining two images having a parallax so that the object illuminated by this illuminating optical system may be stereo-inspected.

By the way, in this specification, this observing optical system is mostly explained in an embodiment acting to form two images having a parallax on an image taking device provided with a photoelectrically converting function and is therefore also called an image taking optical system.

The gripped section 12 is provided with a light guide mouthpiece 13 and a light guide connector 15 at the other end of a light guide cable 14 removably connected at one end to this light guide mouthpiece 13 is removably connected to the light source apparatus 3.

A lamp 16 generating a white illuminating light and a lens 17 condensing this white light are arranged within the light source apparatus 3. The illuminating light condensed by this lens 17 is radiated on the end surface of the light guide connector 15, the illuminating light radiated on this end surface is transmitted by the light guide within the light guide cable 14 and the transmitted illuminating light is fed to the light guide 18 side within the stereoendoscope 2 from the light guide mouthpiece 13.

The light guide 18 used as an illuminating light transmitting means is bent within the gripped section 12 and is inserted through the inserted section 11. This light guide 18 transmits the fed illuminating light and projects the illuminating light forward from the distal end surface fixed to the distal end 19 of the inserted section 11 and further through an illuminating lens 20 fitted to an illuminating window.

The respective optical images (represented by reference numerals 7a and 7b in FIG. 6) of the object (represented by the arrow in FIG. 5) 29 illuminated by this illuminating light are formed in image forming positions by objective optical systems 21a and 21b fitted to two observing windows arranged adjacently to the illuminating window within the distal end 19. The two objective optical systems 21a and 21b are of the same formation and are formed of optical lenses preferably of the same characteristics.

As shown in FIG. 5, the two objective optical systems 21a and 21b have the respective optical axes Oa and Ob in parallel with the center axis of the inserted section, are arranged substantially superimposed in parallel on both sides of this center axis and are separated from each other by d in the distance (interval) between both optical axes Oa and Ob. Also, both optical axes Oa and Ob are arranged as separated in the diametral direction crossing the center axis and are therefore arranged symmetrically with the center axis. Two optical images large in the parallax can be formed by the objective optical systems 21a and 21b of the same formation with the optical axes arranged in parallel as separated by the distance d between them.

Figure 6:
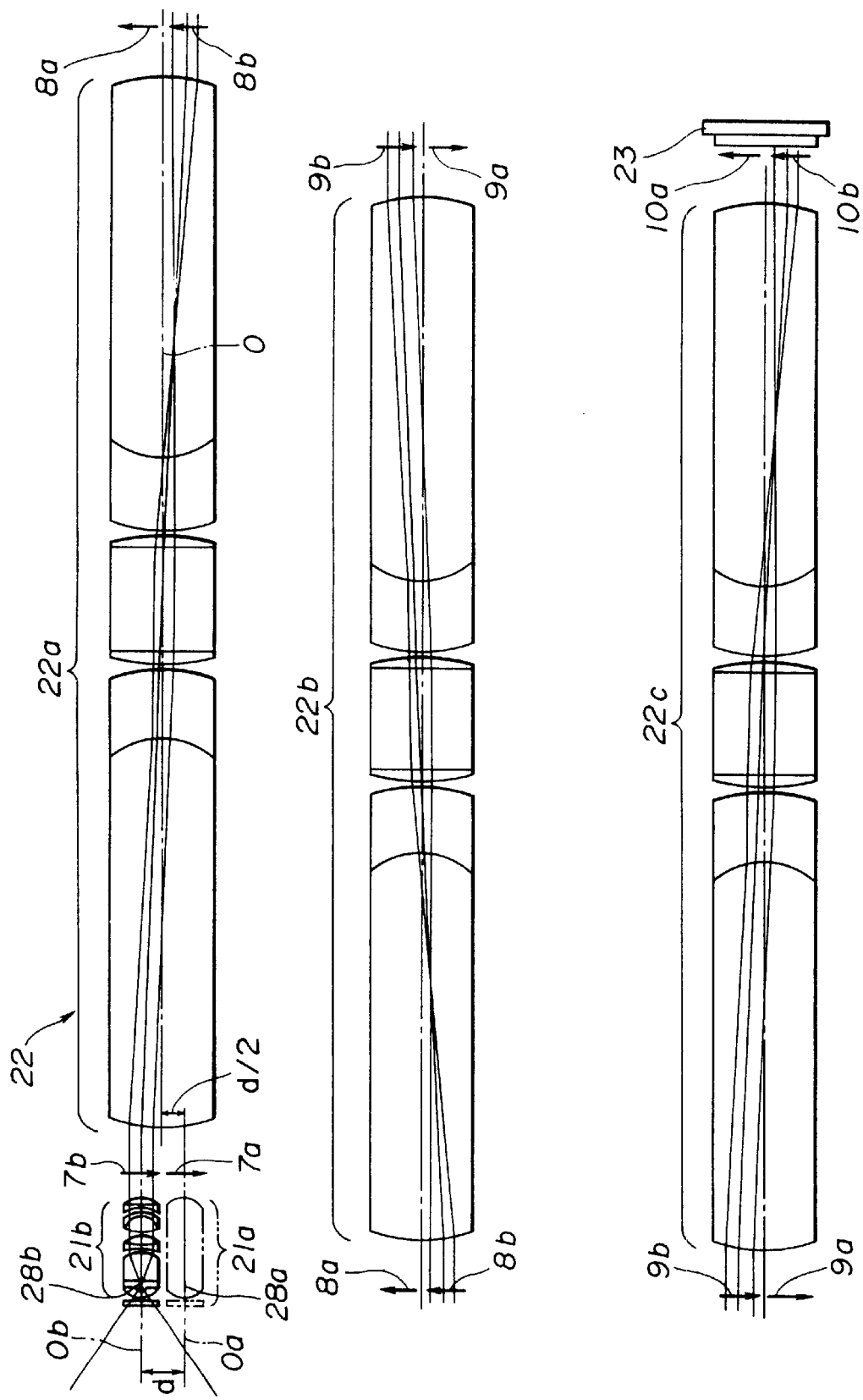

The images 7a and 7b are formed, as shown in FIG. 6, in separate positions by the two objective optical systems 21a and 21b and are transmitted rearward by a common relay optical system 22, that is, one image transmitting optical system or image transmitting means.

These images are both multiple-transmitted rearward by this relay optical system 22 and finally the same images 10a and 10b as the two images 7a and 7b by the two objective optical systems 21a and 21b are separately formed on a photoelectrically converting surface (image taking surface) of an image taking device 23 arranged within the gripped section 12. For example, in FIG. 5, if the separating direction in the two objective optical systems 21a and 21b is a horizontal direction, two images 10a and 10b will be separately formed in the horizontal direction on the image taking surface of the image taking device 23.

As shown in FIG. 5, the image taking device 23 has, for example, a square image taking surface and is arranged so that the vertical or horizontal direction of this image taking surface may coincide with the horizontal direction in which the two objective optical systems 21a and 21b are arranged as separated and the center of the image taking surface may be on the optical axis of the relay optical system.

By the way, the light guide 18 inserted through the inserted section 1 may be inserted through outside the relay optical system 22 (for example, like a ring). As shown in FIG. 5, a part of the vertical direction intersecting at right angles with the horizontal direction of the relay optical system 22 may be contained in an incised groove 422a formed by incising in the axial direction a part of the vertical direction intersecting at right angles with the horizontal direction of the relay optical system 22. (One incised groove 422a is shown in FIG. 5 but two incised grooves may be formed in the vertical direction.) When such an incised groove 422a is formed, the part which does not in principle substantially contribute to image transmission will be deleted, the image transmitting function will not be reduced, the illuminating light will be able to be transmitted and the inserted section 11 will be able to be made small in the diameter.

As the effective sectioned area of the relay optical system can be made large, the eccentricity (the distance d between the optical axes) of the two objective optical systems 21a and 21b arranged as opposed to each other eccentrically in the horizontal direction from the optical axis of this relay optical system 22 at the front end of this relay optical system 22, that is, the parallax will be able to be made large and the stereo-inspecting function will be able to be improved. Further, there is a function of reducing the superimposing (cross talk) of two images.

The gripped section can be fittably separated into the output section 24 in which the image taking device 23 is built-in and the input section 25 on its forward side. The input section 25 has an image taking optical system (observing optical system) comprising the two objective optical series 21a and 21b and relay optical system 22.

Figure 19:
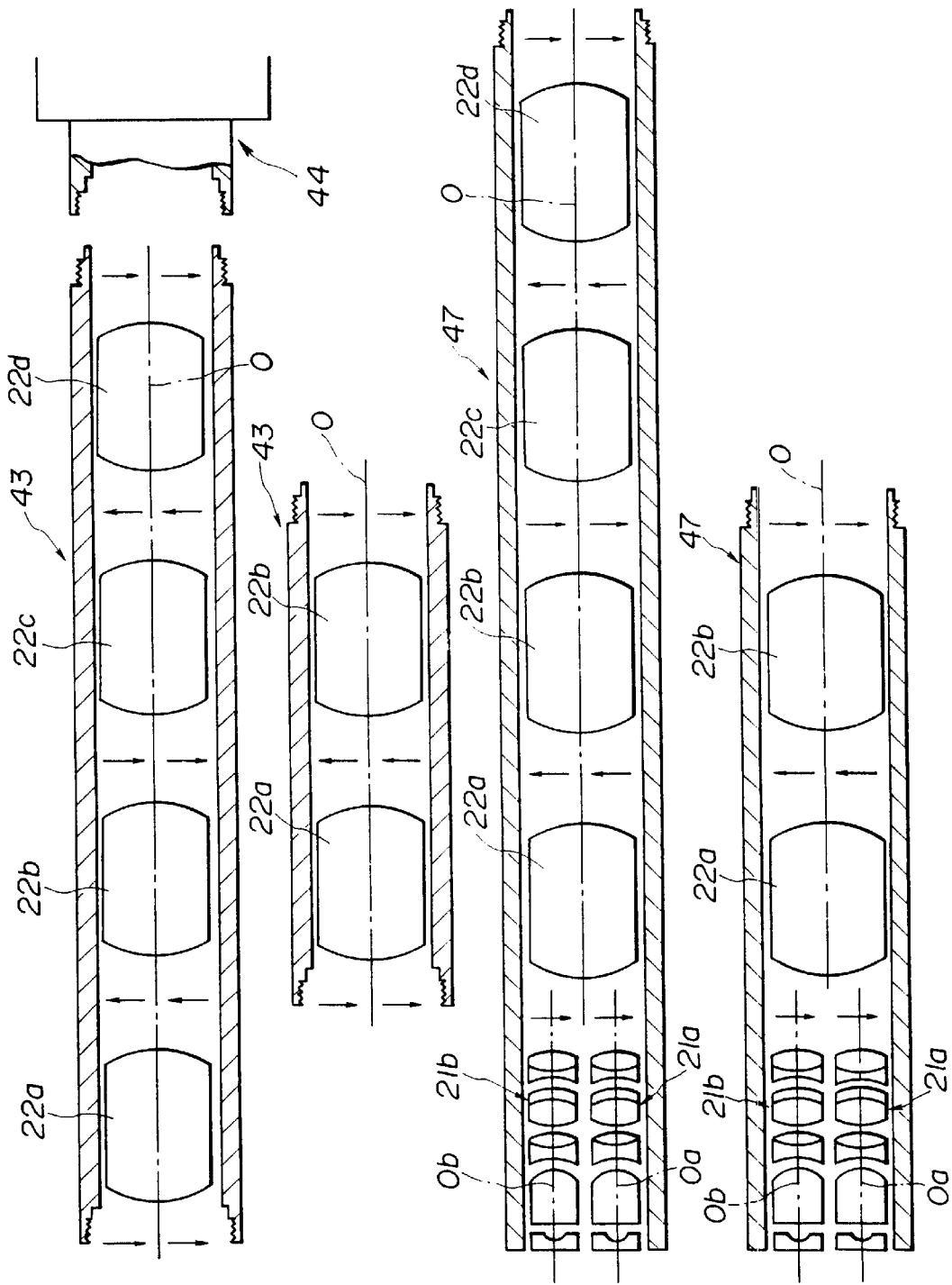
FIGS. 19A to 19D are views respectively showing formations of relay optical system units.

By making the output section 24 separable, there is made a flexible structure wherein the defective image taking device 23 can be easily repaired or can be replaced with one high in the sensitivity or the number of pixels to improve the performance and an ocular adapter can be connected to make stereo-inspection with the naked eyes. (The structure shown in the later described FIG. 19 may be adopted for the structure of the connecting part.)

The image taking device 23 is extended out of the rear end of the output section 24 and is connected with the CCU 4 through the signal cable 26 and the image taking signal photoelectrically converted by the image taking device 23 is processed. The image signal processed by this CCU 4 is further put into the scan converter 5, is converted to a video signal and is then put out to the color monitor 6. Two images corresponding to the optical images formed by the two objective optical systems 21a and 21b are alternately displayed in this color monitor 6. By observing the images of the color monitor 6 with shutter spectacles 27, the operator can stereo-inspect the images.

FIG. 6 shows the formations of the image taking optical systems, that is, the two objective optical systems 21a and 21b and relay optical system in the stereoendoscope 2 of the first embodiment.

The images 7a and 7b having a parallax from each other are formed by the plurality of (two in this embodiment) independent objective optical systems 21a and 21b arranged in the distal end section 19. These images 7a and 7b separated from each other are transmitted by the relay optical system 22 as one image transmitting optical system.

As shown in FIG. 6, the objective optical systems 21a and 21b, for example, the three relay lens systems 22a, 22b and 22c forming the relay optical system 22 and the image taking device 23 having a function of photoelectrically converting optical images are arranged in the order mentioned from the object side. The two images 7a and 7b having a parallax are formed in the spatially separated positions (in this case, in the positions separated from each other in the horizontal direction) by the objective optical systems 21a and 21b of the same formation arranged in parallel as separated from each other by d (for example, d=4 mm) of the distance between their optical axes.

The images 7a and 7b are both multiple-relayed by the relay lens systems 22a, 22b and 22c of the same formation arranged in series so that the optical axes may coincide with each other. That is to say, the images 7a and 7b formed on both left and right sides of the optical axis O of the relay optical system 22 (by the objective optical systems 21a and 21b arranged eccentrically on the left and right from this optical axis O) respectively form images 8a and 8b respectively on both right and left sides of this optical axis O in the rear side positions of the optical axis O by the relay lens system 22a. These images 8a and 8b respectively form images 9a and 9b on both left and right sides of this optical axis O in the rear side positions of the optical axis O by the relay lens system 22b. These images 9a and 9b respectively form images 10a and 10b on both right and left sides of this optical axis O in the rear side positions of the optical axis O by the relay lens system 22c.

In this position, the image taking surface of the image taking device 23 is arranged and the images 10a and 10b are photoelectrically converted and put out. A masking means is provided so that the two images 10a and 10b on this image taking surface may not be superimposed. As shown in the later described FIG. 8, for example, a visual field diaphragm 30 may be provided on the image forming surfaces of the objective optical systems 21a and 21b to limit the visual field. The invention is not limited to this. The visual field diaphragm may be provided, for example, in the image forming position in the relay optical system 22.

The optical axes 0 of the relay lens systems 22a, 22b and 22c are respectively eccentric by the same amount on the right and left from the optical axes Oa and Ob of the objective optical systems 21a and 21b. The eccentricity can be selected in conformity with the desired parallax magnitude, that is, stereo-feel size and is d/2 (for example, d/2=2 mm) in this embodiment.

The number of relaying times is three times in this embodiment but can be set from one time to ten times and several other times depending on such specification as the brightness of the optical system.

By the way, in FIG. 6, the reference numerals 28a and 28b respectively represent the positions of the incident pupils of the left and right objective optical systems 21a and 21b and the left and right images 7a and 7b are formed of the lights incident through the respective incident pupils 28a and 28b. The respective incident pupils 28a and 28b are transmitted by the relay lens systems 22a, 22b and 22c forming the relay optical system 22.

During the transmission by the relay lens systems 22a, 22b and 22c, the two pupils may be horizontally displaced but the relay lens systems 22a, 22b and 22c had better be superimposed in order to be made small. Therefor, it is preferable that the two objective optical systems 21a and 21b are respectively formed to be telecentric optical systems, that is, the projecting pupils are formed to be infinitely far.

By the way, the magnitude of the parallax, that is, the center distance between the left and right incident pupils 28a and 28b is determined by the distance d between the optical axes Oa and Ob of the objective optical systems 21a and 21b and is independent of the brightness of the optical system.

According to this embodiment, as the relay optical system 22 is made common, the trouble of adjusting the lenses can be more extremely omitted than in the case that it is not made common (in the first related art) and a favorable stereo-observation can be made.

Also, as can be judged from FIG. 5, as an image having a parallax can be obtained by arranging the two objective optical systems 21a and 21b as separated from each other, the parallax can be made larger than in the case of using a common objective optical system (in the second related art) and therefore the function of obtaining a stereo-feel can be made large. (The same stereo-feel as in the case that two optical systems are arranged as in the first related art can be obtained.)

Therefore, according to this embodiment, the common optical components can be made few, the adjusted parts can be made few, the cost can be made low and the image having the same stereo-feel as in the case that two optical systems are arranged in the related art can be obtained.

As the two images 7a and 7b having a parallax are transmitted by the relay lens systems 22a, 22b and 22c used in common with the axially symmetrical one, during the transmission, the qualities (the magnification, MTF, image position, chromatic aberration, coloring and the like) of the two images will lag little during the transmission.

That is to say, even if the individual characteristics of the relay lens system 22a and the others are dispersed by the production error, in this embodiment, as the left and right images are transmitted by the common relay lens system 22a and the others, the influence of the individual dispersion will not be substantially received. Therefore, the left and right images obtained by this embodiment will be images of a good quality having little lag.

In case an operation is made under the observation with this stereoendoscope, a good picture quality and a sufficient stereo-feel will be obtained, a picture image of an observation close to directly observing the affected part will be able to be realized and therefore an environment in which the operation is easy to make will be able to be provided.

Also, in this embodiment, as the left and right images 7a and 7b are formed in the positions spatially separated by the objective optical systems 21a and 21b and are formed in the positions spatially separated by the common relay optical system 22, therefore a stereo-inspection will be able to be made with the image taking device or the like without using an image separating means newly spatially separating the images.

Also, in this embodiment, the final images 10a and 10b by the relay lens system 22c are taken by one image taking device 23. Therefore, the output section 24 is very simplified in the structure and a light weight stereoendoscope can be realized.

By the way, the image taking device 23 may be any of various solid state image taking devices (known generally by the names of CCD, PCD, CMD, AMI and SIT) and image taking tubes (known generally by the names of Sachicon, Busicon and HARP TUBE).

Also, the sensitivity may be improved by utilizing an image intensifier or the like.

The image taking device 23 may be a device for taking color images with a single plate or may take colored images with a formation as a 2-plate or 3-plate camera. Also, as shown in FIG. 6, the final images 10a and 10b by the relay lens system 22c are taken by the common image taking device 23 to reduce cost and weight.

In order that a stereo-feel optimum to the desire or operation type of the operator may be obtained, the distance between the respective optical axes of the two objective optical systems 21a and 21b may be made variable so that the magnitude of the parallax may be variable.

In this case, in order that the distal end section 19 may be made small, the two objective optical systems 21a and 21b may be made movable to the side opposite to one another in the horizontal direction vertical to the optical axis O of the relay lens systems 22a, 22b and 22c. However, in this case, when the objective optical systems 21a and 21b move, the final images 10a and 10b will be also moved by the relay lens system 22c and therefore, in case the image taking device 23 is fixed, the movement will be limited to be within the image taking range.

By the way, it has been explained that the image taking surface of the image taking device 23 is square. However, a rectangular surface having a long horizontal direction in which the objective optical systems 21a and 21b are arranged as separated may be used. In this case, the image taking range in which the image having a parallax is obtained will be able to be substantially expanded.

By the way, FIG. 5 shows a simultaneous illuminating and image taking system wherein a color image is taken by using the image taking device 23 in which such color separating filter as a mosaic filter is arranged under a white color light illumination. However, the invention is not limited to this. A surface sequential image taking system wherein a color image is taken by obtaining such color component image as of three primary colors by taking an image with an image taking device having no color separating filter under a surface sequential illumination in which illuminating lights of such wavelength ranges as of red, green and blue are sequentially emitted on the object side will also do.

Figure 1A:
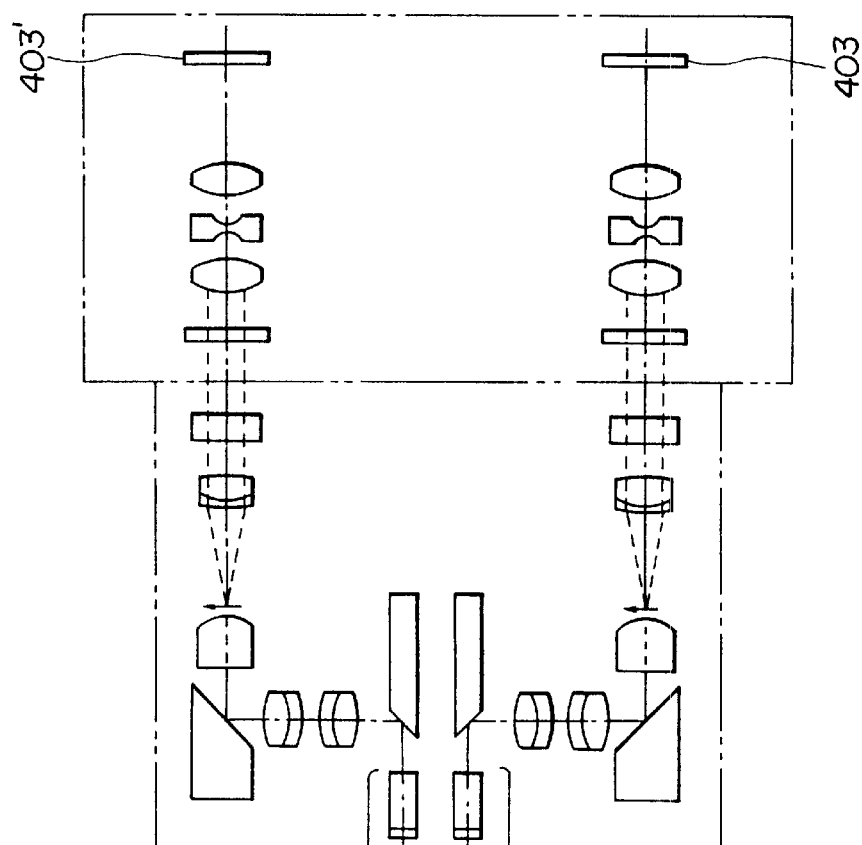
FIGS. 1A and 1B show a first related art example, where
Figure 1B:
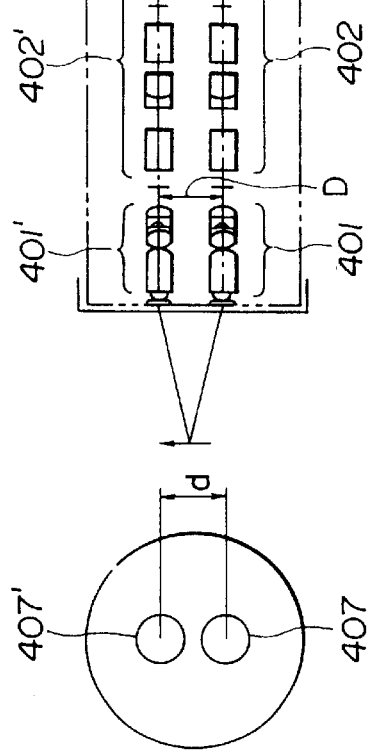
Figure 2A:
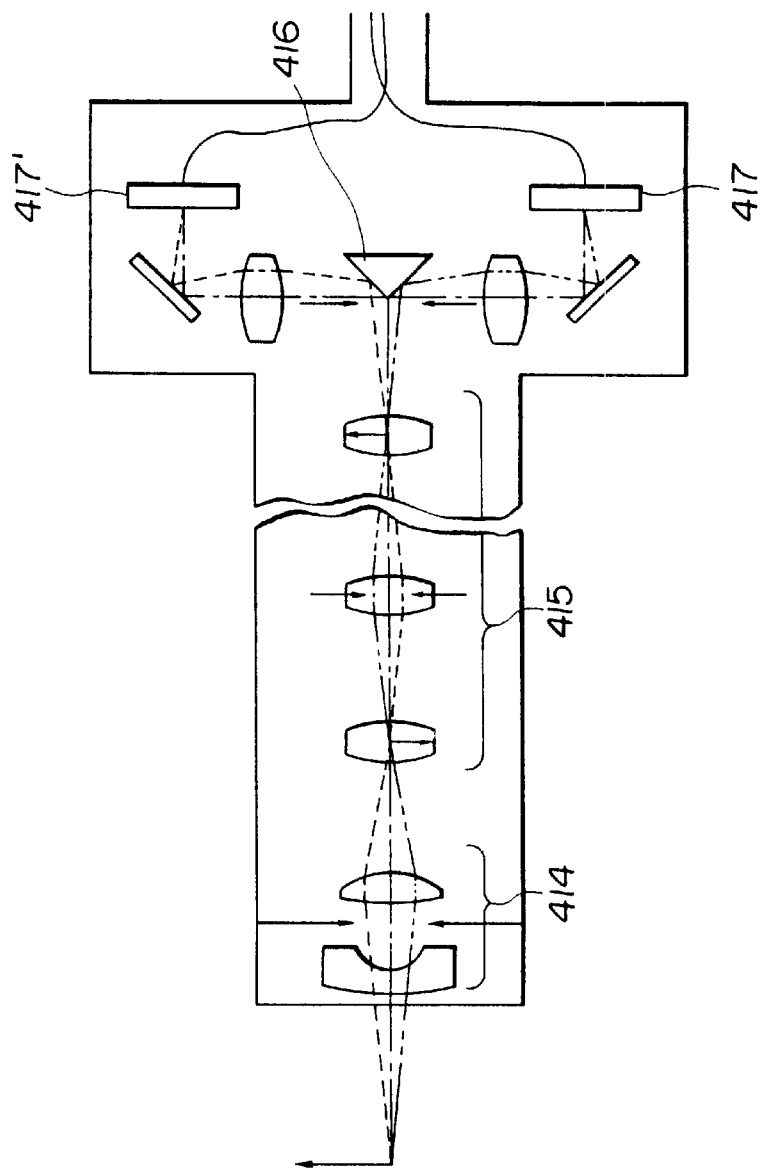
FIGS. 2A and 2B show a second related art example, where
Figure 2B:
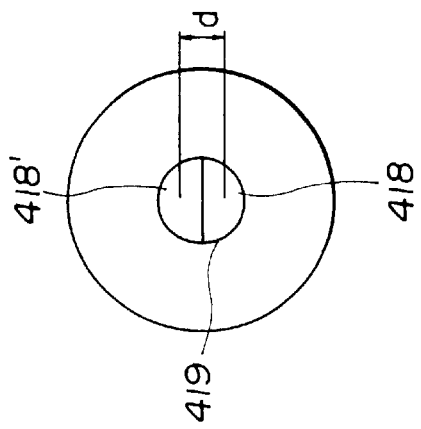
Figure 3:
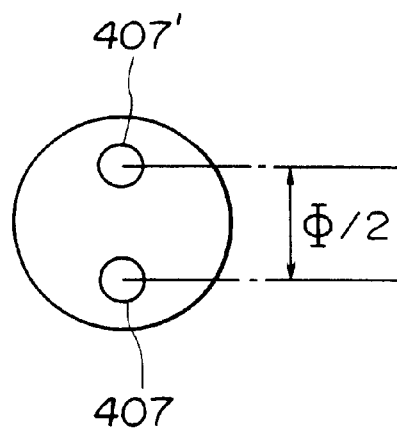
FIG. 3A is a magnified sectioned view of an objective optical system part on the distal end side of the first related art example and FIG. 3B is an explanatory view showing incident pupils of FIG. 3A.
Figure 3:
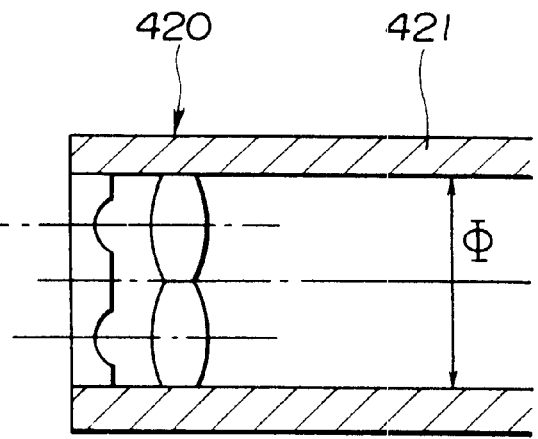
Figure 4:
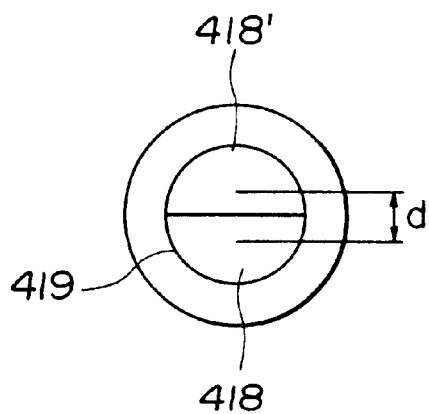
FIG. 4A is a magnified sectioned view of an objective optical system part on the distal end side of the second related art example and FIG. 4B is an explanatory view showing an incident pupil of FIG. 4A.
Figure 4:
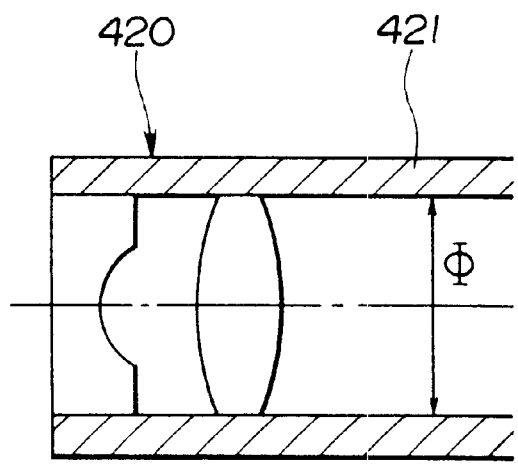
Figure 16:
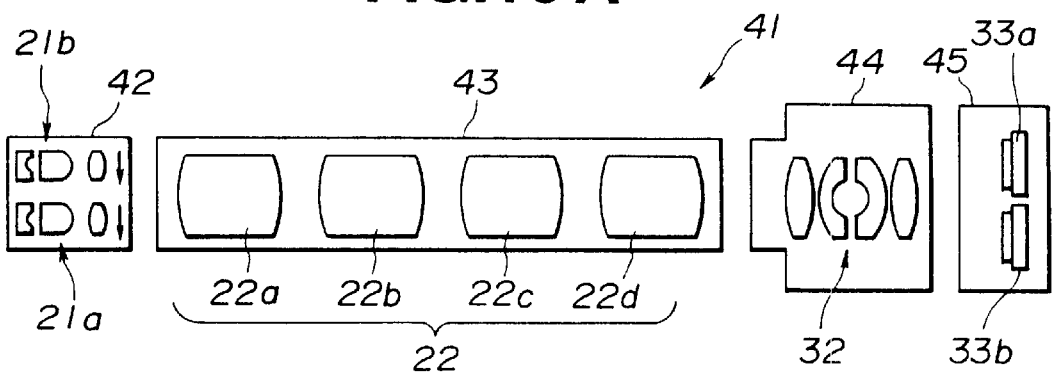
FIGS. 16A and 16B show the ninth embodiment of the present invention, where
FIGS. 16C and 16D show a first modification of the ninth embodiment, where
Figure 16:
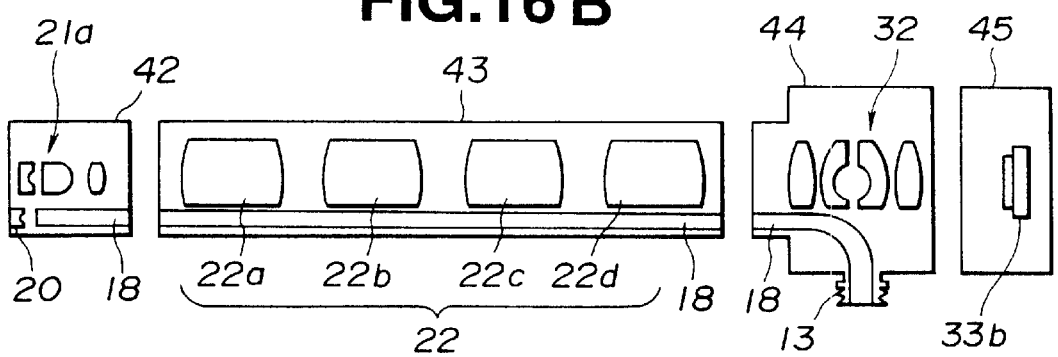
Figure 16:
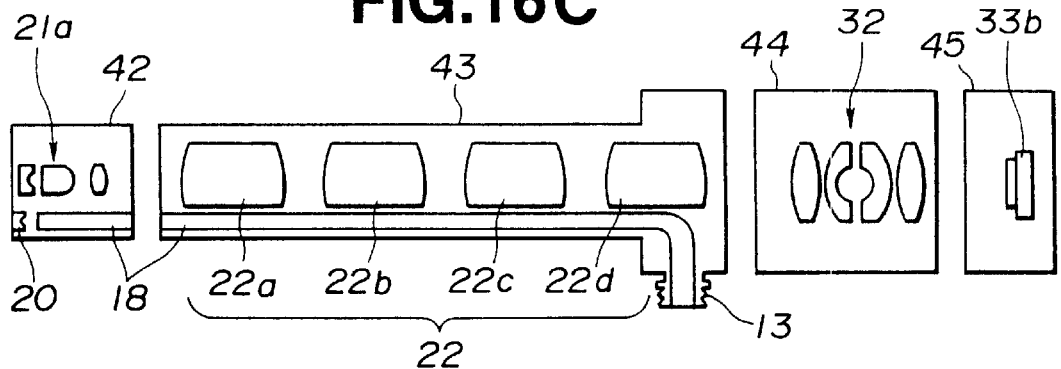
Figure 16:
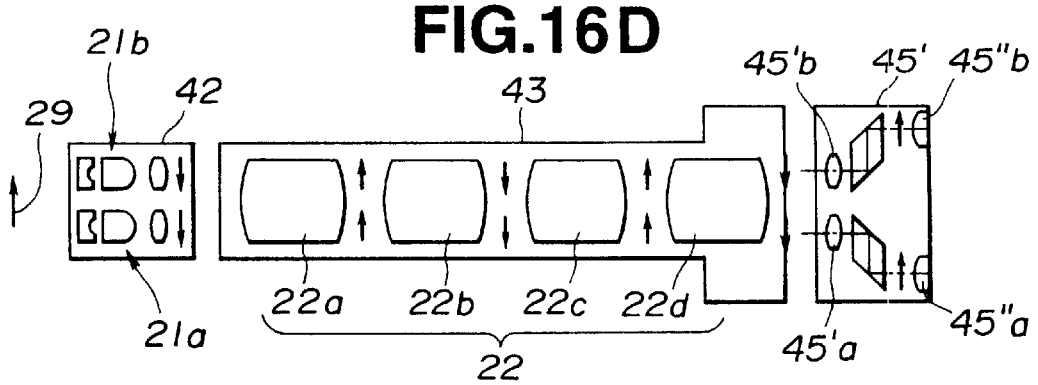

By the way, in the first embodiment, instead of connecting the output section to the input section 25, an ocular adapter 45' shown in the later described FIG. 16D is fitted so that the stereo-inspection may be made with the naked eyes. In this case, it is preferable to set the number of relaying times by the relay optical system 22 at an even number of times so that the left and right images 7a and 7b by the objective optical systems 21a and 21b may be respectively observed with the left and right ocular lenses. (In FIG. 16D, the number of relaying times is four times.) By the way, the lens data of the first embodiment are as in Table 1 shown later in the specification. FIG. 2 and others are collectively shown after FIG. 1. In Tables 1 to 14, r1, r2, . . . , represent radii of curvatures of respective surfaces, d1, d2, . . . , represent surface distances, n1, n2, . . . , represent refractive indices of respective lenses and v1, v2, . . . , represent Abbe numbers of respective lenses.

In the following, the second to ninth embodiments are modifications of the first embodiment and, the same as in the first embodiment, the image having a parallax is formed in a position spatially separated by the objective optical systems 21a and 21b.

Figure 7:
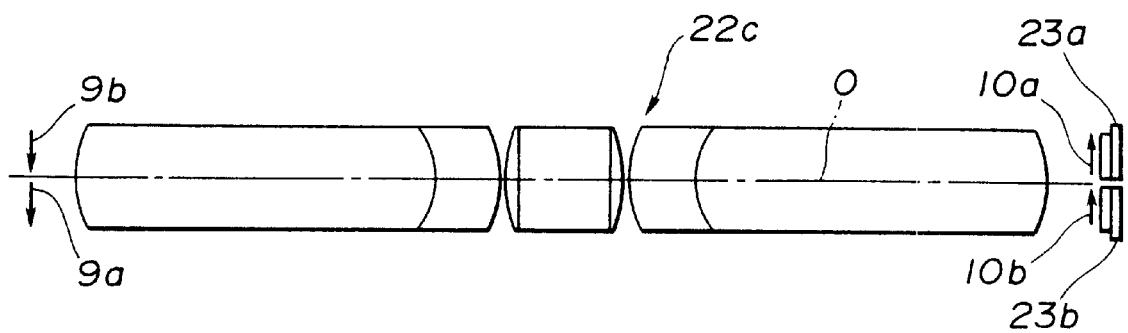
FIG. 7 is a formation view showing an image taking optical system in the second embodiment of the present invention.

FIG. 7 shows a structure near the final images 10a and 10b of the relay lens system 22c of the image taking optical system in the stereoendoscope of the second embodiment of the present invention. The final images 10a and 10b are respectively taken by the two image taking devices 23a and 23b. Signal lines (not illustrated) are connected respectively to the two image taking devices 23a and 23b and are connected to a CCU partly different in the internal formation from the CCU 4 in FIG. 5. The others are of the same formation as of the stereoendoscope 2 of the first embodiment.

By the way, in the CCU processing signals for the two image taking devices 23a and 23b, the same driving signal may be simultaneously applied, for example, to the two image taking devices 23a and 23b, may be simultaneously read out and may be memorized respectively in two frame memories. The same driving signal may be applied alternately respectively to the two image taking devices 23a and 23b and may be read out alternately and the image signal read out may be memorized alternately in the two frame memories.

The image signal simultaneously or alternately memorized in the two frame memories are alternately read out by the scan converter and are alternately displayed in the color monitor. The operator wears shutter spectacles 27 and can observe and stereo-inspect the image displayed in the color monitor 6.

The stereoendoscope apparatus provided with this second embodiment can be realized in substantially the same formation as of the stereoendoscope apparatus 1 in FIG. 5.

This second embodiment has an advantage that the image taking devices 23a and 23b can be focused respectively independently. If they are precisely adjusted, an image higher in the quality than in the case of a common image taking device 23 will be able to be made.

Also, the parallax can be made variable the same as in the first embodiment. However, this embodiment has an advantage that, when the left and right image taking devices 23a and 23b are moved as operatively connected with the movement of the objective optical systems 21a and 21b, the movement will not be restricted to be within the image taking range in the case of the common image taking device 23.

That is to say, in the first embodiment, as the image taking device 23 is common, the moving range of the left and right images 10a and 10b is restricted to be within the image taking range. However, according to the present embodiment, in case the final images 10a and 10b are fixed, when the movement deviates (separates) from the imaging range, the two image taking devices 23a and 23b will be moved horizontally as operatively connected with the movement of the objective optical systems 21a and 21b and the final images 10a and 10b will be able to be maintained within the image taking range of the respective image taking devices 23a and 23b.

Therefore, there is a merit that a stereo-endoscope in which an image having a stereo-feel is obtained can be realized. The others have the same effects as in the first embodiment. By the way, the lens data of the second embodiment are the same as of the first embodiment.

Figure 9:
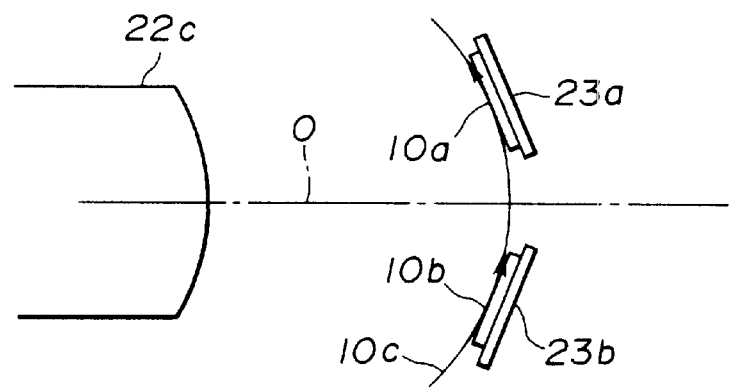
FIG. 9 is an explanatory view showing an arrangement example of an image taking device.
Figure 8:
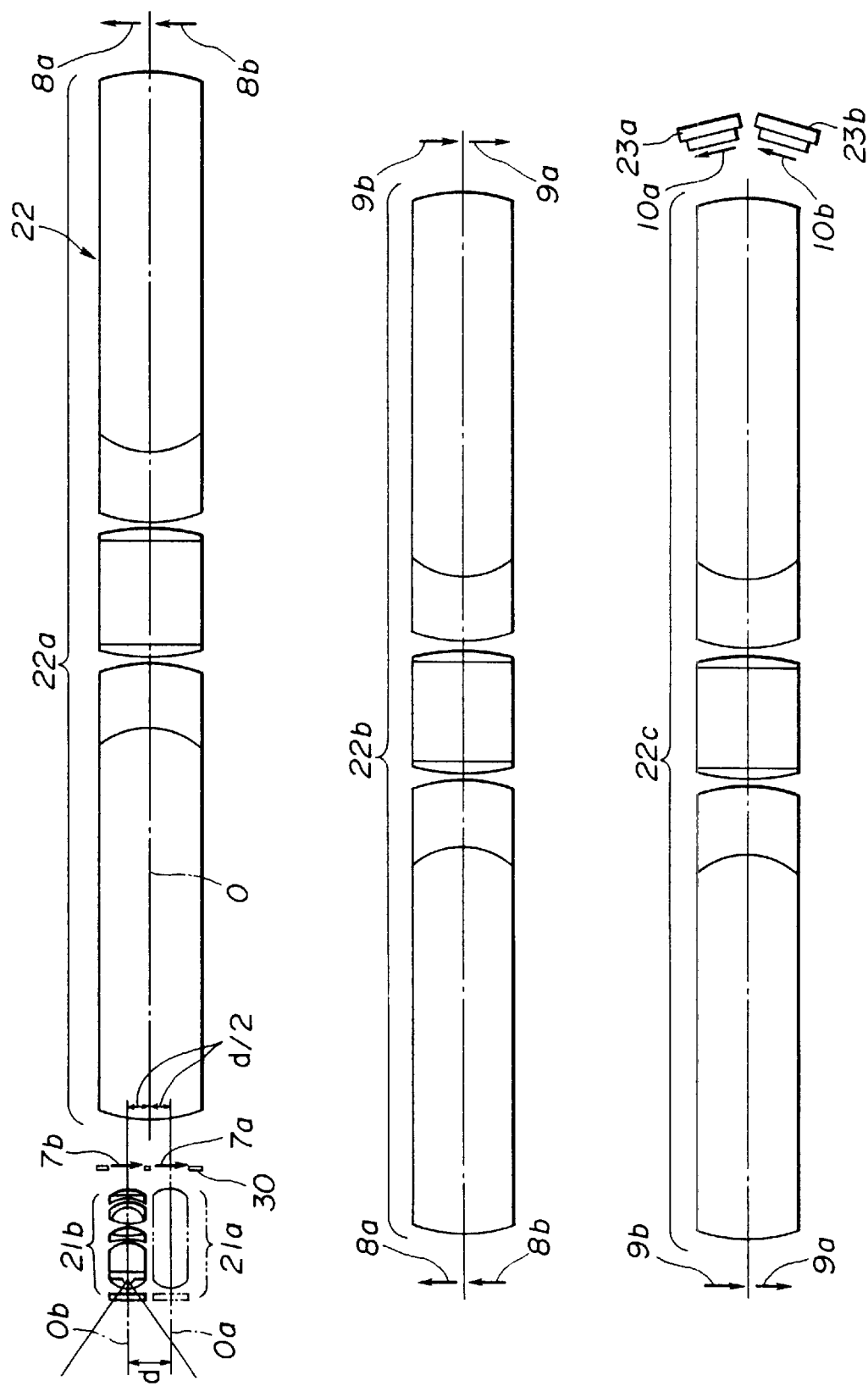
FIG. 8 is a formation view showing an image taking optical system in the third embodiment of the present invention.

FIGS. 8 and 9 relate to the third embodiment of the present invention. FIG. 8 shows an image taking optical system in the third embodiment. FIG. 9 shows as magnified the arrangement of the image taking devices 23a and 23b. In this embodiment, the two image taking devices 23a and 23b are used as in the second embodiment and the light receiving surfaces of the image taking devices 23a and 23b arranged not vertically to the optical axis O of the relay optical system 22 but as inclined from the vertical direction. In other words, in the central part of the light receiving surface of each of the image taking devices 23a and 23b, the optical axis vertical to this light receiving surface is arranged not to be parallel with the optical axis O of the relay optical system 22 but to make an angle greater than O.

That is to say, when the light receiving surface of each of the two image taking devices 23a and 23b is inclined in conformity with the image surface curvature aberration 10c generated by the relay lens systems 22a, 22b and 22c and shown in FIG. 9, the deterioration of the image by the curvature aberration will be reduced.

As the petzval of the relay lens systems 22a, 22b and 22c is positive, even if the image surface by the objective optical systems 21a and 21b is flat, in the case of the transmission by the relay lens systems 22a, 22b and 22c, the image surface will bend on the curved surface with the concave surface directed to the objective side.

Therefore, with the image taking surface or light receiving surface left to be arranged vertically to the optical axis of the relay lens systems 22a, 22b and 22c, a partial fog will likely be produced and it will be difficult to keep the entire image taking surface focused.

Therefore, in the third embodiment, as shown in FIG. 9, the light receiving surface is inclined in conformity with the contact surface of the curved image surface. In FIG. 9, the light receiving surface is inclined by 25.332 degrees to the surface vertical to the optical axis of the relay lens system 22c.

According to this third embodiment, not only the effects of the second embodiment are retained but also a picture image having little curvature aberration is obtained. By the way, the lens data of the third embodiment are as in Table 2.

By the way, because the petzval sum of the relay lens systems 22a, 22b and 22c is a positive value, the petzval sum of the objective optical systems 21a and 21b may be made a negative value to control the image surface curvature aberration of the final images 10a and 10b having passed through the relay lens system 22c.

FIGS. 10A and 10B are of modifications showing this manner.

Figure 10:
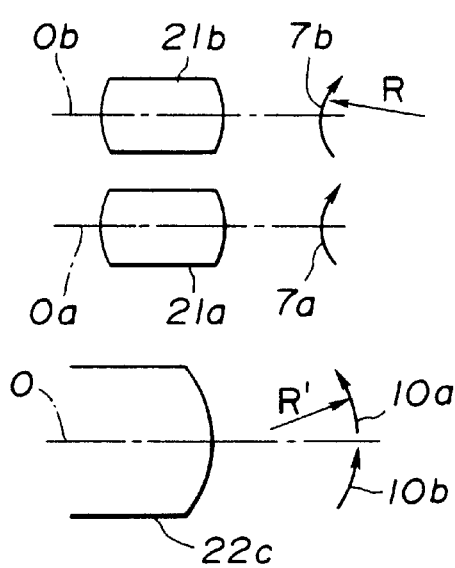
FIGS. 10A and 10B relate to a modification of the third embodiment, where
Figure 10:
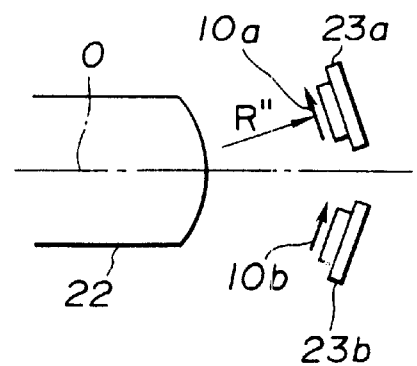

As shown in FIG. 10A, the petzval sum of the objective optical systems 21a and 21b is made a negative value to form images 7a and 7b becoming concave on the rear side (the local radius of curvature of each image surface shall be represented by R). In case the image on the flat image surface is transmitted by the relay lens systems 22a, 22b and 22c, the local radius of curvature of the image surface of the final images 23a and 23b is represented by R' and, as shown in FIG. 10, the light receiving surfaces of the image taking devices 23a and 23b are arranged on the contact surface of the curved surface of a local curvature 1/R"=1/R−1/R", the influence of the image surface curvature aberration will be further controlled by this embodiment than by the third embodiment.

By the way, in this case, 1/R−1/R"=0 or the absolute value of 1/R−1/R" may be made small.

FIG. 11 shows an image taking optical system in the fourth embodiment. The final images 10a and 10b of the relay lens system are relayed once more by adapter lens systems 32a and 32b forming an adapter optical system to connect images 36a and 36b and these images 36a and 36b are taken respectively by image taking devices 33a and 33b.

The adapter lens systems 32a and 32b are formed respectively of mirror parts 34a and 34b and lens parts 35a and 35b, a beam is parallel moved outside by the mirror parts 34a and 34b (in this embodiment, the displacement L is 6 mm) and the lens parts 35a and 35b act to re-form the final images 10a and 10b of the relay lens system at any magnification.

The optical axis of each of the lens parts 35a and 35b is eccentric by d/2 (2 mm) from the optical axis of the relay lens system 22c except the parallel moved part by the mirror parts 34a and 34b.

In this embodiment, when the parallel moving distance in the mirror sections 34a and 34b and the magnification in the lens sections 35a and 35b are properly set, images 36a and 36b optimum to any size image taking devices 33a and 33b will be able to be obtained.

Also, as the image taking devices 33a and 33b larger in the size than in the first and second embodiments can be used, those larger in the number of pixels in response to the size can be used and a favorable stereo-observed image high in the resolving degree can be obtained. The others have the same effects as in the second embodiment. The lens data of this embodiment are as in Table 3.

Figure 12:
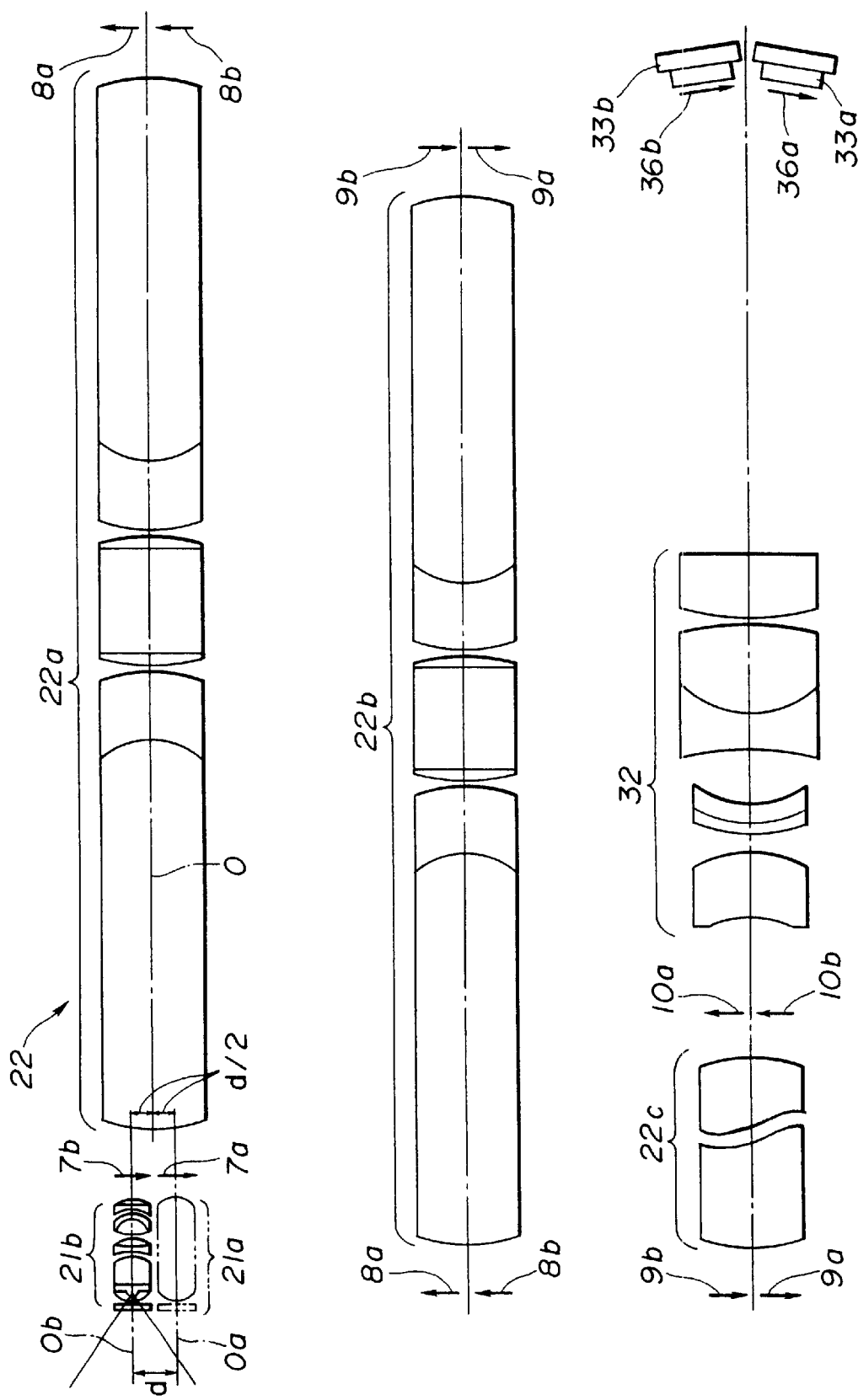
FIG. 12 is a formation view showing an image taking optical system in the fifth embodiment of the present invention.

FIG. 12 shows an image taking optical system in the fifth embodiment. This embodiment is an improvement of the fourth embodiment.

The images 36a and 36b are respectively formed by further relaying once the final images 10a and 10b of the relay lens system with the common adapter optical system 32 formed of one lens system and are taken by the image taking devices 33a and 33b. The adapter optical system 32 is formed of a lens system arranged so as to be of the same optical axis as of the relay lens systems 22a, 22b and 22c, the final images 10a and 10b of the relay lens system are formed again at any magnification and the image taking devices 33a and 33b are arranged in the image forming positions.

In this embodiment, the formation can be made simpler by the part having no mirror section within the adapter optical system 32 and has the operations and effects of the fourth embodiment. That is to say, when the magnification of the adapter optical system 32 is optionally set, the images 36a and 36b optimum to the image taking devices 33a and 33b of any size will be able to be obtained.

Also, in this embodiment, the same as in the third embodiment, the light receiving surface of each of the image taking devices 33a and 33b is inclined in conformity with the image surface curvature aberration generated by the relay lens systems 22a, 22b and 22c and adapter optical system 32 to control the deterioration of the image. In FIG. 12, the light receiving surface is inclined by 11.902 degrees to the surface vertical to the optical axis of the relay lens system 22c. The lens data of this embodiment are shown in Table 4.

Figure 13:
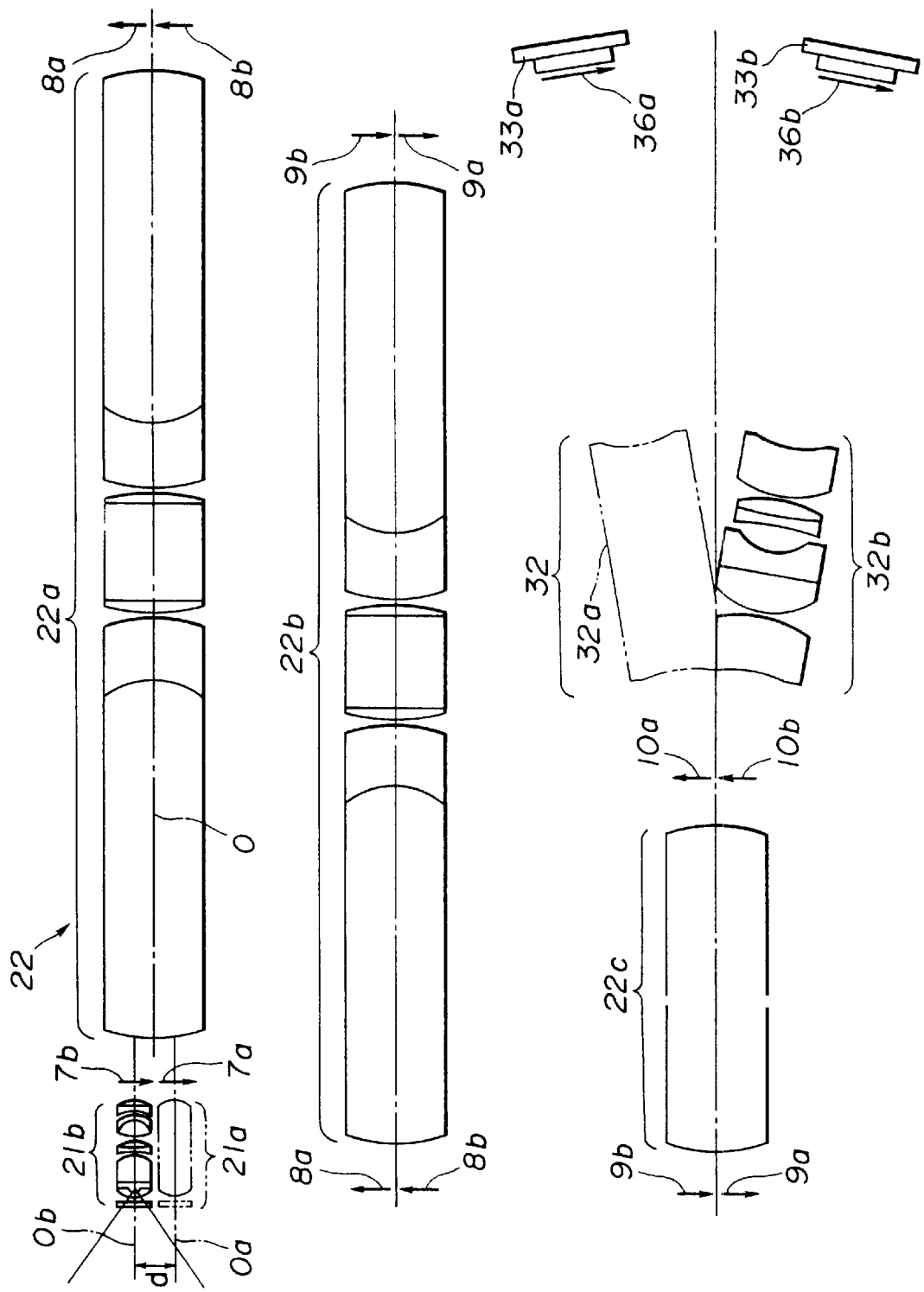
FIG. 13 is a formation view showing an image taking optical system in the sixth embodiment of the present invention.

FIG. 13 shows an image taking optical system in the sixth embodiment.

The final images 10a and 10b of the relay lens system are further once relayed by the adapter lens systems 32a and 32b forming the adapter optical system 32 and are taken by the image taking devices 33a and 33b. The adapter optical system 32 is formed of the two inclined adapter lens systems 32a and 32b of the same formation. One lens system 32b and the image taking device 33b are parallel eccentric by d/2 (=2 mm) from the optical axis of the relay lens system 22c and are then inclined by 10.076 degrees with the point at which the optical axis of the lens system 32b intersects with the final image 10b of the relay lens system 22c as a center. The lens system 32a illustrated by the two-point chain lines is also inclined the same on the opposite side of the optical axis of the relay lens system 22c.

In this embodiment, too, the same as in the fifth embodiment, no mirror section is present and, by freely setting the magnification of the adapter optical system, the images 36a and 36b optimum to the image taking device of any size can be obtained. That is to say, this embodiment has substantially the same effects as in the fifth embodiment. The lens data of this embodiment are as in Table 5.

Figure 14:
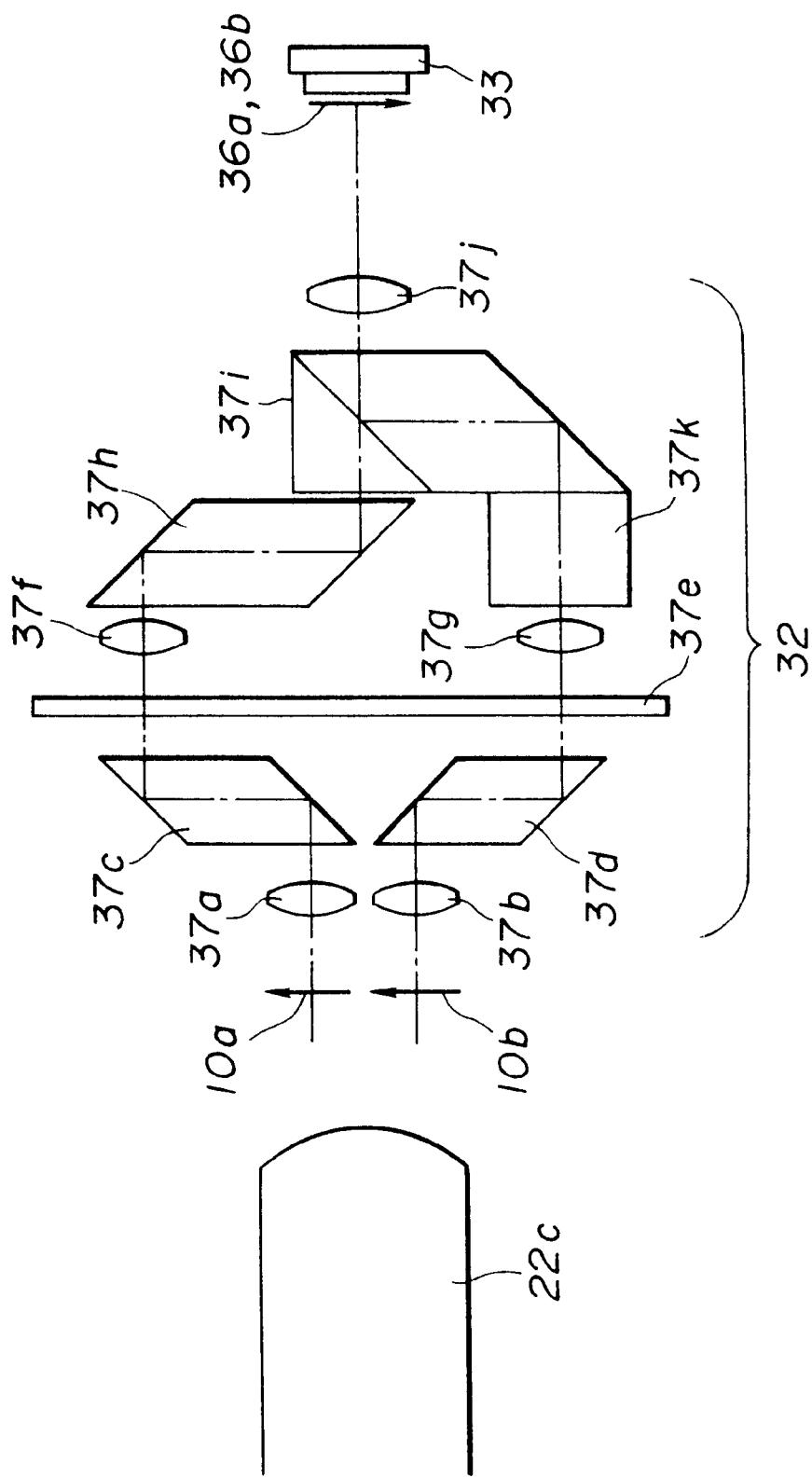
FIG. 14 is a formation view showing a main part of an image taking optical system in the seventh embodiment of the present invention.

FIG. 14 shows a main part of an image taking optical system in the seventh embodiment of the present invention.

The final images 10a and 10b of the relay lens system are further once relayed by the adapter optical system 32 and are formed in the same positions and the common image taking device 33 is arranged in the image forming position in the formation.

In the adapter optical system 32, the final images 10a and 10b of the relay lens system are led to the shutter means 37e side through an optical axis distance extending means comprising respectively lenses 37a and 37b and prisms 37c and 37d and are led to the opposed lens 37f and 37g side so that, when one is shielding light, the other will be passing light. A beam having passed through the lens 37f arranged as opposed to one side of the shutter means 37e passes through the prism 37h, half prism 37i and lens 37j and forms an image 36a in the position in which the image taking device 33 is arranged.

Also, a beam having passed through the lens 37g arranged as opposed to the other side of the shutter means 27e passes through the optical device 37k, half prism 37i and lens 37j and forms an image 36b in the position in which the image taking device 33 is arranged.

In this embodiment, the relayed images 36a and 36b are formed in the same position and are taken by one image taking device 33. The shutter means 37e is arranged on the way of the adapter optical system 32 and alternately shields the beam so that two images may not be simultaneously formed by the image taking device 33.

This embodiment has an advantage that one image taking device 33 will do and the cost can be reduced. The others have the same effects as of the fourth embodiment.

FIGS. 15A and 15B show a formation of an objective optical system in the eighth embodiment of the present invention.

In this embodiment, an objective optical system is formed of perspective objective optical systems 39a and 39b having a perspective front as a visual field.

In this embodiment, a beam incident from the diagonal front side is reflected by using reflecting prisms 40a and 40b as visual field direction changing means and is changed to be in a direction parallel to the optical axis O of the relay optical system 22 (FIGS. 15A and 15B show only a part of the relay lens system 22a). In this embodiment, the visual field direction is 45 degrees with the lengthwise direction (the optical axis direction of the relay optical system 22) of the inserted section. The reflecting prisms 40a and 40b may be two separate bodies or one integral body.

The rear side formation of the relay optical system 22 may be the formation of any of the first to sixth embodiments. This embodiment has the same effects as in the first to seventh embodiments except that the visual field direction is different.

Other than the eighth embodiment, the visual field direction can be varied by varying the angles of the reflecting prisms 40a and 40b. Also, if the objective optical system parts are replaceably formed, various visual field directions, visual field angles and parallaxes will be able to be obtained by replacing only the objective optical system.

FIGS. 16A to 16D show the ninth embodiment of the present invention and a unit formation in its first modification.

The stereoendoscope 41 of the ninth embodiment shown in FIG. 16A comprises an objective optical system unit 42, relay optical system unit 43, adapter optical system unit 44 and image taking device unit 45.

The objective optical system unit 42 has objective optical systems 21a and 21b of uniform optical characteristics built-in. The relay optical system unit 43 has relay lens systems 22a, 22b, 22c and 22d of the same formation built-in. The adapter optical system unit 45 has a common adapter optical system 32 built-in. The image taking device unit 45 has image taking devices 33a and 33b of uniform characteristics built-in.

FIG. 16A as seen from the side is as in FIG. 16B. The objective optical system unit 42 has a distal end side section of a light guide 18 and an illuminating lens 20 built-in. The relay optical system unit 43 has an intermediate section of the light guide 18 built-in. The adapter optical system unit 44 has a rear end side section of the light guide 18 built-in. A light guide mouthpiece 13 is provided.

Also, in this embodiment, the relay lens systems 22a, 22b, 22c and 22d within the relay optical unit 43, for example, (for example, are cut off in the lengthwise direction on the lower side to be in the direction vertical to the horizontal direction in which the objective optical systems 21a and 21b are arranged to secure a space to contain the light guide 18 and) make the inserted section small in diameter. Also, the adapter optical system 32 within the adapter optical system unit 44 is cut off on the light guide mouthpiece 13 side.

In this embodiment, the objective optical system unit 42 is connected to the distal end of the relay optical system unit 43, the distal end of the adapter optical system unit 44 is connected to the proximal end of the relay optical system unit 43 and the image taking device unit 45 is connected to the proximal end of this adapter optical system unit 44 to form a stereoendoscope 41.

Therefore, by combining the respective units different in the optical characteristics and image taking characteristics, stereoendoscopes of different characteristics can be simply realized. Therefore, the stereoendoscopes 41 of different characteristics can be provided.

In this embodiment, the connecting part of the proximal end of the relay optical system unit 43 and the distal end of the adapter optical system unit 44 corresponds to the border of the input section 25 and output section 24 shown in FIG. 5.

By the way, in FIGS. 16A and 16B, the part after the adapter optical system unit 44 is made large in diameter. However, as shown in FIG. 16C, the proximal end side of the relay optical system unit 43 may be made large in the diameter on the proximal end side, the proximal end side part of the light guide 18 may be built-in near this proximal end and the light guide mouth piece 13 may be provided there in the structure.

In this first modification, the light guide 18 need not be built-in in the adapter optical unit 44 and therefore the structure will be simple.

In this modification, the image taking device unit 45 may be fitted directly to the relay optical system unit 43 without using the adapter optical system unit 44 in the structure. In such a case, the formation of the second embodiment will be made. Further, in case one common image taking device is built-in as the image taking device unit 45, the formation of the first embodiment will be made.

This first modification is higher in the freedom of combination than the ninth embodiment and can simply realize stereoendoscopes 41 different in the characteristics. Also, as shown in FIG. 16D, when an ocular adapter 45' is connected to the proximal end of the relay optical system unit 43, a stereoendoscope by which stereo-inspection can be made with the naked eyes will be able to be formed.

The ocular adapter 45' shown in FIG. 16D has a structure whereby the final images by the relay optical system unit 43 can be magnified and observed respectively through prisms and ocular lenses 45"a and 45"b fitted to an ocular window corresponding to the distance between both eyes of the operator so that the left and right images by the objective optical systems 21a and 21b may be respectively stereo-inspected through the left and right ocular lenses 45"a and 45"b.

By the way, in this case, because the final images are inverted images, the ocular adapter 45' is provided with lenses 45'a and 45'b as means for making them upright to form upright images in front of the ocular lenses 45"a and 45"b. Instead of providing the lenses 45'a and 45'b, the two prisms for extending the distance between the optical axes may consist of prisms for inverting images such as Porro prisms.

The ocular adapter for observation with the naked eye may be connectable to the relay optical system unit 43 in FIG. 16A in the structure or may be connectable to the second to fourth modifications of the ninth embodiment shown in FIGS. 17A to 17C explained in the following.

Figure 17A:
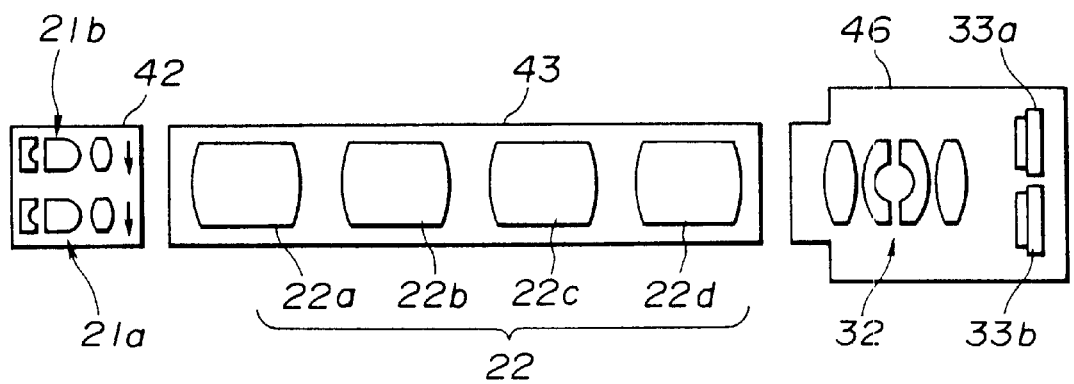
FIGS. 17A to 17C are explanatory views respectively showing unit formations in the second to fourth modifications of the ninth embodiment.

In the second modification shown in FIG. 17A, in FIG. 16A, the adapter optical system 32 and the image taking devices 33a and 33b are formed of an adapter optical system image taking unit 46 as one unit.

Figure 17B:
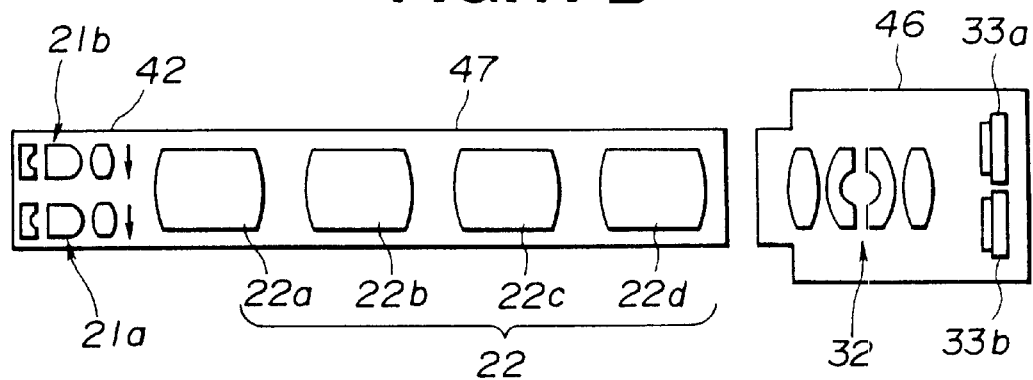
Figure 17C:
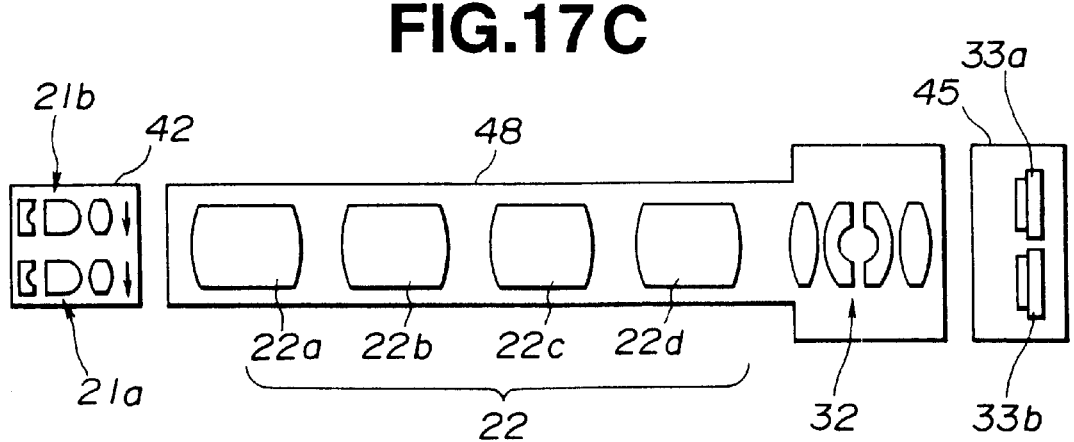

In the third modification shown in FIG. 17B, in FIG. 17A, further, the objective optical systems 21a and 21b and the relay optical system 22 are formed of an objective optical system relay optical system unit 47 as one unit. In the fourth modification shown in FIG. 17C, in FIG. 16A, the relay optical systems 22 and the adapter optical system 32 are formed of a relay optical system adapter optical system unit 48 as one unit.

FIGS. 18A to 18E show more actual formations of various units used in the ninth embodiment and its modifications.

FIG. 18A shows an objective optical system unit 42 of a visual field angle of 70 degrees. FIG. 18B shows an objective optical system unit 42 of a visual field angle of 40 degrees. When they are replaced and are connected to a relay optical system unit 43, any desired visual field angle will be obtained.

A male screw is formed at the proximal end of the jacket tube of the objective optical system unit 42 and can be removably connected by being screwed to a female screw at the distal end of the jacket tube of the relay optical system unit 43. A projection is provided at the proximal end of the jacket tube of the objective optical system unit 43 and can be contacted with a level difference surface made by cutting off the inner peripheral surface on the distal end side of the jacket tube of the relay optical system unit 43 to determine the position in the lengthwise direction. By the way, both jacket tubes have the same outside diameter so that, in case they are connected with each other, no level difference will be made on the inserted section.

Also, a positioning mark and screw hole are provided as peripheral positioning means near the proximal end of the jacket tube of the objective optical system unit 42. When this mark is made to meet a positioning mark at the distal end of the jacket tube of the relay optical system unit 43, both screw holes will be able to be set to communicate with each other and will be able to be fixed with a screw (not illustrated).

By the way, the same connecting means or connecting mechanism as on the proximal end side of the jacket tube of the objective optical system unit 42 is provided on the proximal end side of the jacket tube of the relay optical system unit 43 and can be removably connected to the distal end of the jacket tube of the adapter optical system unit 44.

FIG. 18C shows an objective optical system unit 42 perspective in the visual field direction of 45 degrees. In FIG. 18C, by replacing the reflecting prism 40, the objective optical system unit 42 perspective in any visual field direction can be formed. By the way, FIG. 18D shows FIG. 18C as seen from the rear end side and a pair of objective optical systems 39a and 39b arranged on the left and right.

FIG. 18E shows an objective optical system 42 in which the parallax is reduced and the optical axes of two objective optical systems 21a and 21b are near each other and the distance d' between the optical axes is d'<d. In this formation, the stereo-feeling will be reduced but, as the objective optical systems are arranged on the center axis side, a space for inserting them through other internal organs or the like will be able to be secured, therefore, for example, the cross-sectioned area of the light guide will be able to be made large, the illuminating light amount will be able to be increased and a bright image will be obtained.

By the way, when the image taking device unit or the adapter optical system unit is replaced, as required, in response to the optical axis distance and visual field angle of the objective optical systems 21a and 21b, an optimum stereoendoscope conforming to the equivalent will be able to be provided.

FIG. 19A shows a formation of a relay optical system unit 43. The proximal end of this relay optical system 43 can be removably connected to the distal end of the adapter optical system unit 44. Also, the proximal end of this adapter optical system unit 44 can be removably connected to the image taking unit 45.

As shown, for example, in FIG. 19B, the relay optical system unit may be the relay optical system unit 43 in which the number of relaying times is doubled. Further, a relay optical system unit in which the number of relaying times is different depending on the length inserted into the body cavity or the like can be also used.

FIG. 19C shows a formation of an objective optical system relay optical system unit 47 for integrating an objective optical system and a relay optical system. FIG. 19D is a modification of FIG. 19C and shows a unit in which the number of relaying times of the relay optical system is doubled. Various numbers of relaying times of the relay optical system can be prepared. A different length of the inserted section can be selected as required.

In the following, the tenth to eighteenth embodiments are embodiments of the formation (b) in the above mentioned paragraph of the summary. Images having a parallax with each other are taken into the plurality of front group optical systems of the objective optical systems arranged in the distal end section of the endoscope and a plurality of images in one rear group optical system are formed in substantially coinciding positions. These substantially superimposed images are transmitted by a common rear group optical system and a common image transmitting system coinciding with this rear group optical system in the optical axis.

Figure 20:
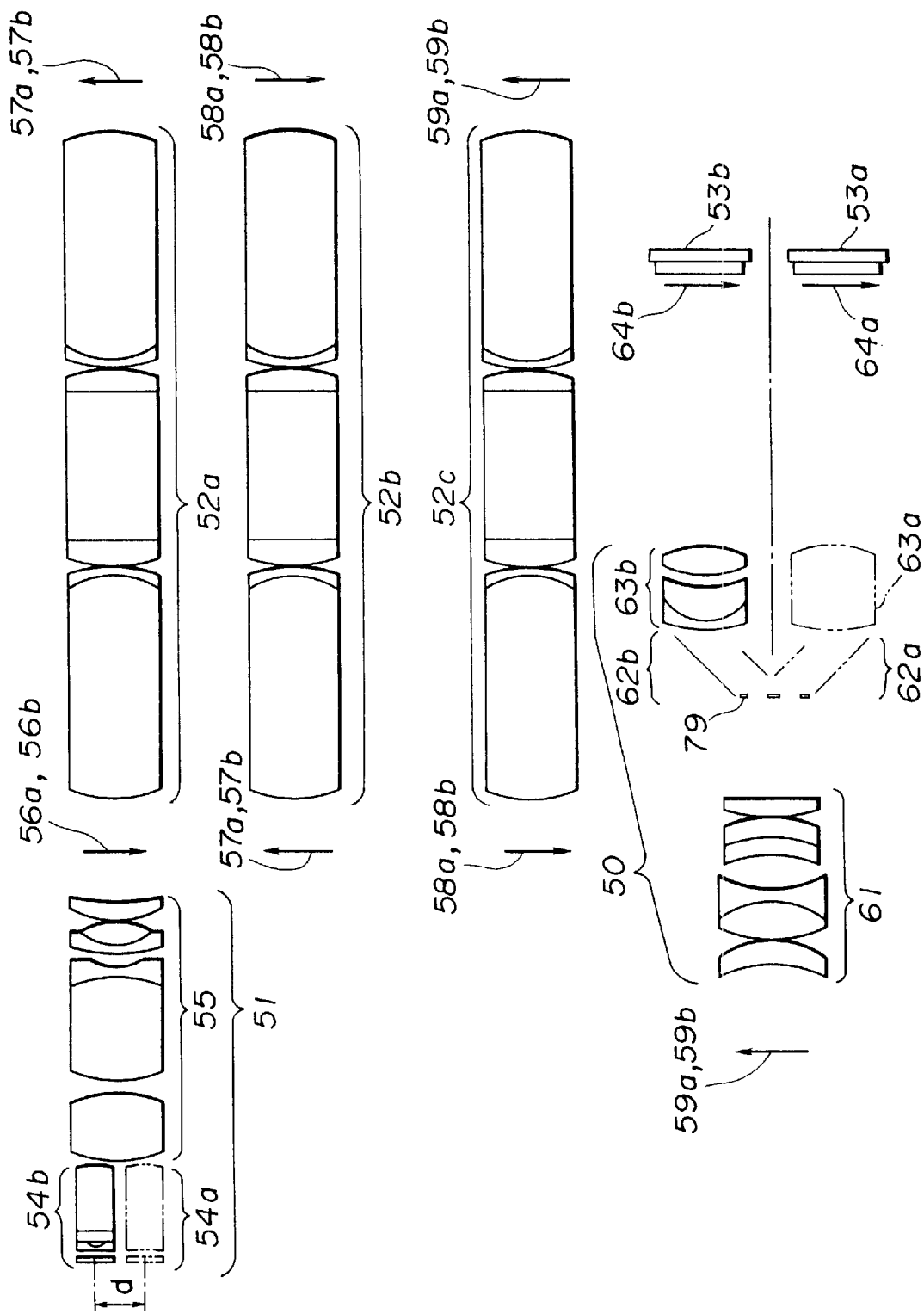
FIG. 20 is a formation view showing an image taking optical system in the tenth embodiment of the present invention.

FIG. 20 shows an image taking optical system in the tenth embodiment.

An objective optical system 51 in which the object side opening part is separated into two parts, relay lens systems 52a, 52b and 52c, an adapter optical system 50 and image taking devices 53a and 53b are arranged in the order mentioned from the object side. The objective optical system 51 is formed of front group optical systems (abbreviated merely as front groups) 54a and 54b of the same formation which are arranged parallel as separated by the distance d (=4 mm) between the optical axes of each other and a rear group optical system (abbreviated merely as a rear group) 55 arranged to be of one same optical axis. Two images 56a and 56b having a parallax are formed in spatially substantially coinciding positions.

The images 56a and 56b form a relay optical system and are equally multiple-relayed by (for example, three) relay lens systems 52a, 52b and 52c of the same formation arranged in series so as to have the same optical axis.

That is to say, by the relay lens system 52a, the images 56a and 56b form images 57a and 57b with equal sizes in substantially the same positions in the rear of this relay lens system 52a. By the relay lens system 52b, these images 57a and 57b form images 58a and 58b with equal sizes in substantially the same positions in the rear of this relay lens system 52b. By the relay lens system 52c, these images 58a and 58b form images 59a and 59b with equal sizes in substantially the same positions in the rear of this relay lens system 52c.

The rear group 55 of the objective optical system 51 and the optical axis of the relay lens systems 52a, 52b and 52c are on the same axis. This optical axis and the optical axis of the front groups 54a and 54b are respectively eccentric on the left and right.

The eccentricity can be selected in conformity with a desired size, that is, the size of the stereo-feel and is respectively d/2 (=2 mm) in this embodiment. An a focal beam may not be between the front groups 54a and 54b and the rear group 55. However, this part may be of an a focal beam. An image formed by the objective optical system should be substantially superimposed.

For the picture angle of the ordinary relay system, the picture angle required by the endoscope is large. Because, as described above, the front groups 54a and 54b must be nearly a focal and because there must be few parts not in common, the front groups 54a and 54b must be formed of a concave group and a convex group from the object side.

When the plurality of images having a parallax and which are transmitted by the relay optical system are substantially superimposed, the relay optical system will be able to be made small in the diameter. Therefore, the projected pupil of the objective optical system 51 may be made substantially infinite. Therefore, the front side focal position of the rear group 55 of the objective optical system 51 will be the pupil position. So that the beam entering the front groups 54a and 54b from the object may be well transmitted to the rear group 55, it is preferable to the projected pupil of the front groups 54a and 54b coincide. It is preferable that the final surfaces of the front groups 54a and 54b are arranged on the image side rather than in the front side focal position of the rear group 55.

In this embodiment, there are three relaying times which can be selected and set to be usually one time to ten or more times depending on such specifications as the length and diameter of the inserted section of the endoscope and the brightness of the optical system.

The magnitude of the parallax, that is, the center distance between the right and left incident pupils, is determined by the optical axis distance d between the front groups 54a and 54b of the objective optical system 51 and is independent of the brightness of the optical system.

According to this embodiment, the same as in the first embodiment, the two images 56a and 56b having a parallax are transmitted by one axially symmetrical relay optical system and therefore little error will be generated in the various optical qualities (the magnification, MTF, image position, chromatic aberration, coloring and the like) of the two images being transmitted.

There are fewer non-common parts on the right and left of the objective optical system 51 than in the first embodiment. Therefore, the adjustment of lenses proves not to be troublesome and a favorable stereo-observed image can be obtained.

Further, in this embodiment, as spatially substantially superimposed images are transmitted by the relay optical system, when each of the front groups 54a and 54b is formed of an elliptic lens system in which, for example, the horizontal direction is a short axis and the vertical direction is a long axis and the pupil is also made elliptic, the objective optical system and relay optical system will be able to be made small in diameter without deteriorating the parallax, brightness and the like. In this case, the inserted section will be able to be made small in diameter from the distal end to the proximal end side and the applied range in which the endoscope can be inserted and used will be able to be expanded. Because the hole through which the inserted section is inserted into the abdominal part can be made small, the patient will experience a reduction in pain. By the way, even in the other embodiments, the objective optical system may be formed of an elliptic lens system.

In this embodiment, the final images 59a and 59b of the relay lens system 52c are in substantially the same position and therefore must be separated from each other by any means which is a pupil dividing image forming means.

Therefor a means for forming an image of a pupil transmitted by the relay optical system and a means for forming an image of a partial beam of this pupil and forming an image by spatially separating plural images having a parallax are required. The adapter optical system 50 formed of the pupil image forming lens system 61, mirror parts 62a and 62b and image forming lens systems 63a and 63b arranged to be on the same optical axis as of the relay lens system 52c perform these functions.

The pupil image forming lens system 61 forms in spatially separated positions images of two pupils of the objective optical system 51 transmitted by the relay lens systems 52a, 52b and 52c. In the mirror parts 62a and 62b, the beams of the two pupils are moved outside (in this embodiment, the movement is 6 mm) in parallel and the image forming lens systems 63a and 63b form images 64a and 64b respectively in the image taking devices 53a and 53b.

The optical axes of the image forming lens systems 63a and 63b are eccentric by d/2 (=2 mm) from the optical axis of the relay lens system 52c, except for the part moved in parallel by the mirror parts 62a and 62b. By the way, the mirror parts 62a and 62b and image forming lens systems 63a and 63b are illustrated respectively only on one side.

Lest the right and left pupils should be finally superimposed, a brightness diaphragm 79 may be provided on the pupil surface (in this embodiment, on the projecting pupil surface of the pupil image forming lens) in any of the pupil position and its conjugate position to limit the beam.

In this embodiment, when the parallel moving distance in the mirror parts 62a and 62b and the magnification of the adapter optical system 50 are properly set, the images 64a and 64b optimum to the image taking devices 53a and 53b of any size will be able to be obtained.

As in FIG. 20, the parallel moving direction of the mirror parts 62a and 62b may be any direction within or vertical to a plane containing the paper surface. When the focal distances of the image forming lens systems 63a and 63b are varied, the magnification will be able to be also varied.

In order to obtain the stereo-feel optimum to the operator's desire or a system, the optical axis distances between each other of the two front groups 54a and 54b may be made variable so that the magnitude of the parallax may be variable. In this case, in order to make the distal end section small, the two front groups 54a and 54b may be made movable in the directions reverse to each other vertically to the optical axis of the relay optical system.

However, in this case, because the projected pupil of the objective optical system is moved by the movement of the front groups 54a and 54b, it will be necessary to make the effective diameter of each lens rather large so that the beam may not be intercepted by the optical systems following the relay lens systems 52a, 52b and 52c.

The other operations and effects are the same as in the first embodiment. The lens data of this embodiment are shown in Table 6.

The following eleventh to seventeenth embodiments are made by modifying the formations of the tenth embodiment.

The images having a parallax between each other are formed in spatially substantially coinciding positions. All these objective optical systems 51 can be formed to be interchangeable with the objective lenses of the pupil dividing type stereoendoscope of the related art.

Figure 21:
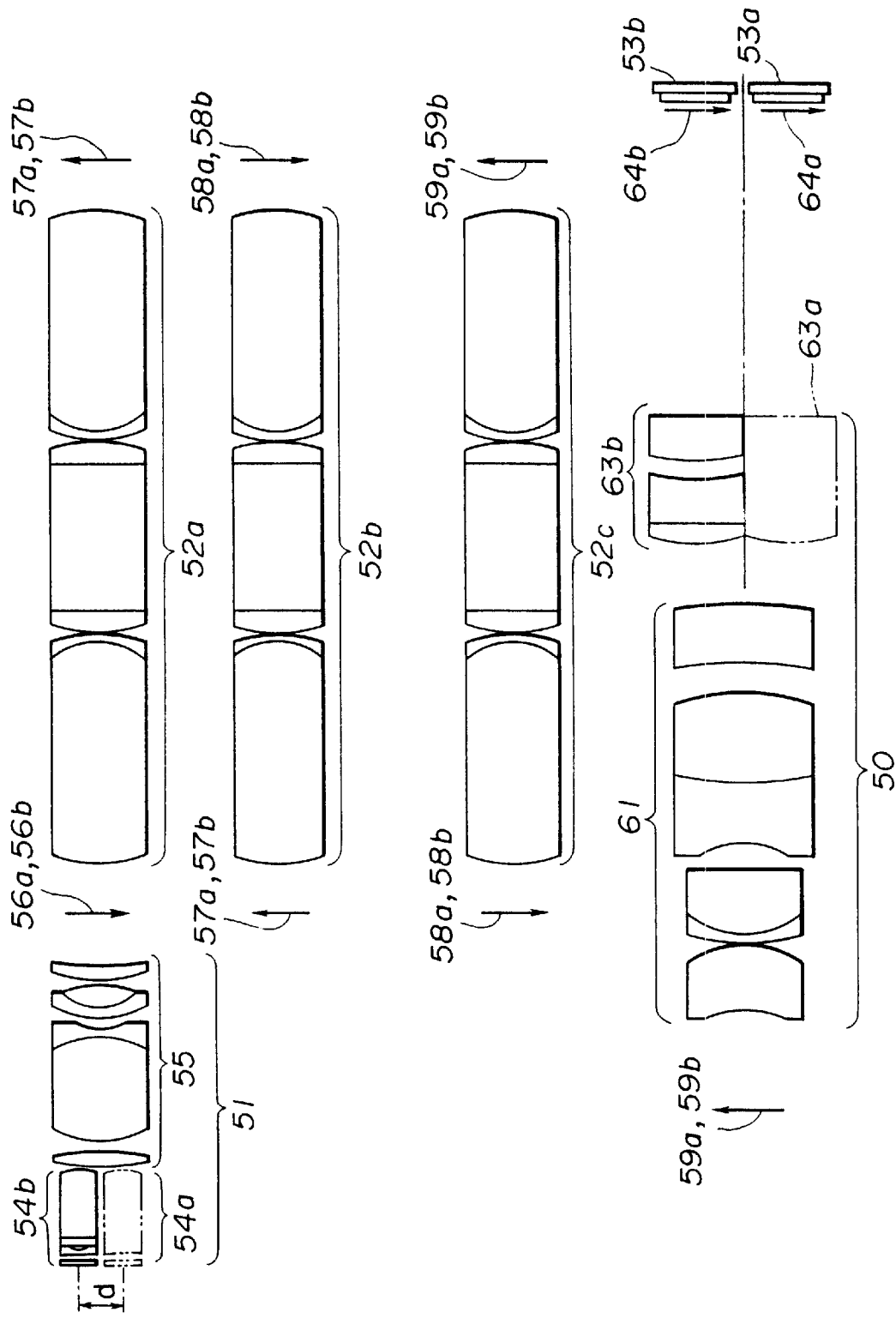
FIG. 21 is a formation view showing an image taking optical system in the eleventh embodiment of the present invention.

FIG. 21 shows an image taking optical system in the eleventh embodiment of the present invention. Images 64a and 64b are formed by further once relaying the final images 59a and 59b of the relay lens system with the adapter optical system 50 and are taken by the image taking devices 53a and 53b.

The adapter optical system 50 is formed of a pupil image forming lens system 61 and image forming lens systems 63a and 63b arranged to be of the same optical axis as of the relay lens system 52c. The optical axes of the image forming lens systems 63a and 63b are eccentric by 1.25d (=5 mm) from the optical axis of the relay lens system 22c.

By the way, the image forming lens system is illustrated only on one side. This embodiment is simpler than the tenth embodiment because there is no mirror part within the adapter optical system 50. As in the tenth embodiment, when the magnification of the adapter optical system 50 is freely set, the images 64a and 64b optimum to any image taking device will be able to be obtained. The distance between the two pupils divided by the pupil image forming lens system 61 can be varied by adjusting the focal distance of this pupil image forming lens system 61. The other operations and effects are the same as in the tenth embodiment.

The lens data of this embodiment are shown in Table 7.

Figure 22:
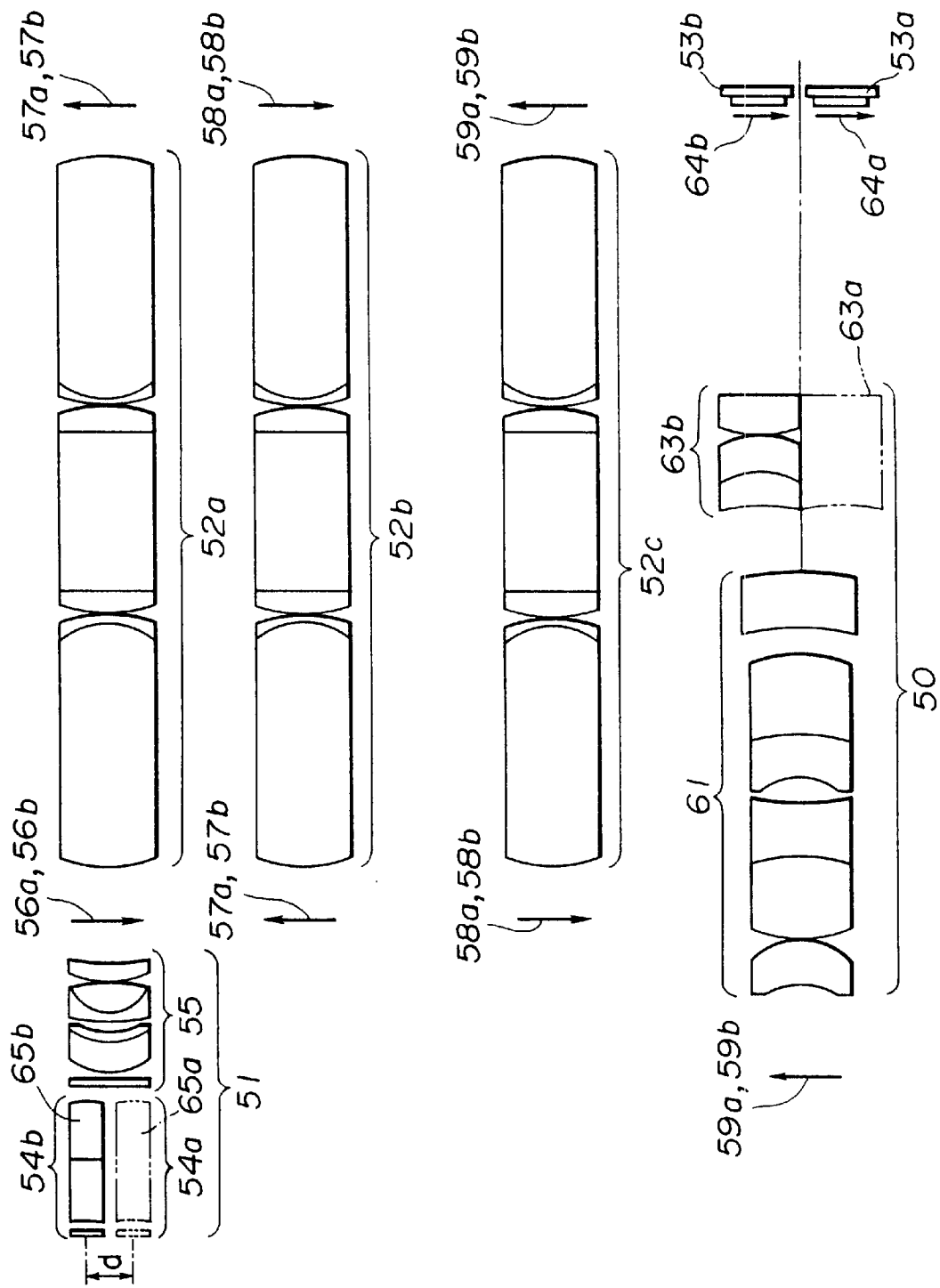
FIG. 22 is a formation view showing an image taking optical system in the twelfth embodiment of the present invention.

FIG. 22 shows an image taking optical system in the twelfth embodiment of the present invention. The front groups 54a and 54b of the objective optical system 51 are formed of meniscus lenses 65a and 65b having a concave surface on the object side. In this embodiment, because there are fewer non-common parts of the right and left light paths than in the eleventh embodiment, the error between the qualities of the two images will be less.

The lens data of this embodiment are shown in Table 8.

Further, when the meniscus lenses 65a and 65b are constructed as an integrally molded lens 65 as shown in FIGS. 23A to 23D, the error on the right and left from the objective optical system 51 to the pupil image forming lens system 61 will be able to be reduced to a level where the error will not be a practical problem and the trouble of adjusting the lenses will be well eliminated. The other operations and effects are the same as in the eleventh embodiment.

Figure 23D:
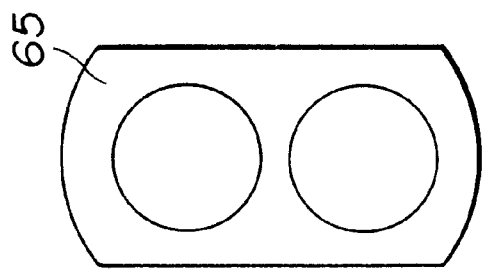
FIGS. 23A to 23D show a meniscus lens in a modification of the twelfth embodiment, where
Figure 23A:
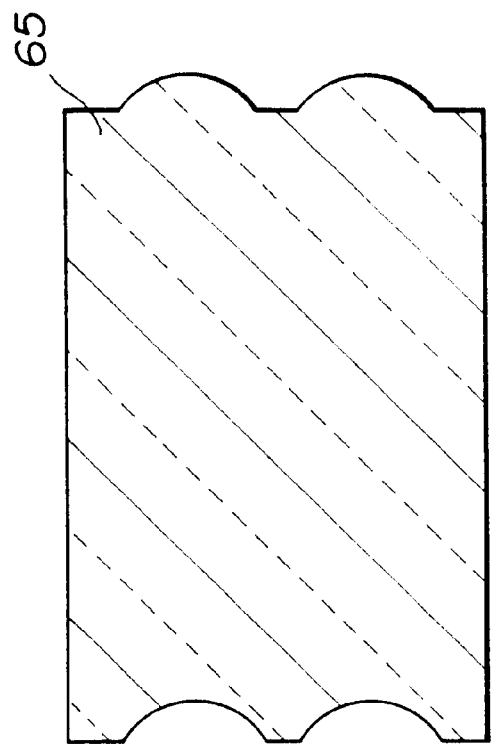
Figure 23B:
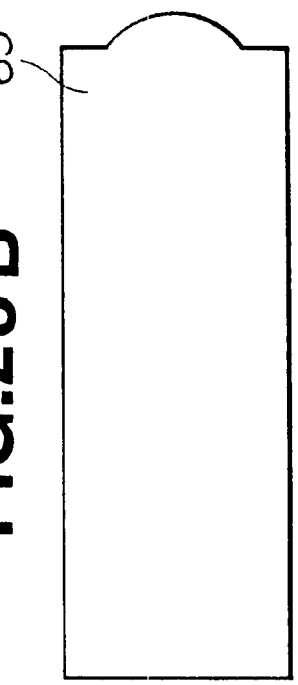
Figure 23C:
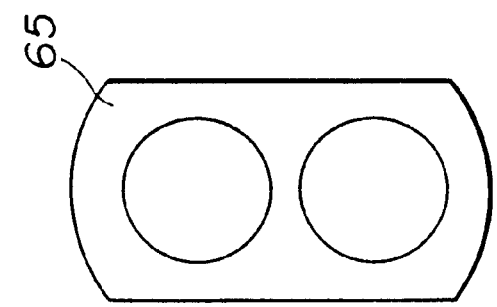

By the way, of FIGS. 23A to 23D, FIG. 23A is a sectioned plan view, FIG. 23B is a side view of FIG. 23A as seen in the side direction and FIGS. 23C and 23D are a front view and back view, respectively, as seem from the front side and back side.

Figure 24:
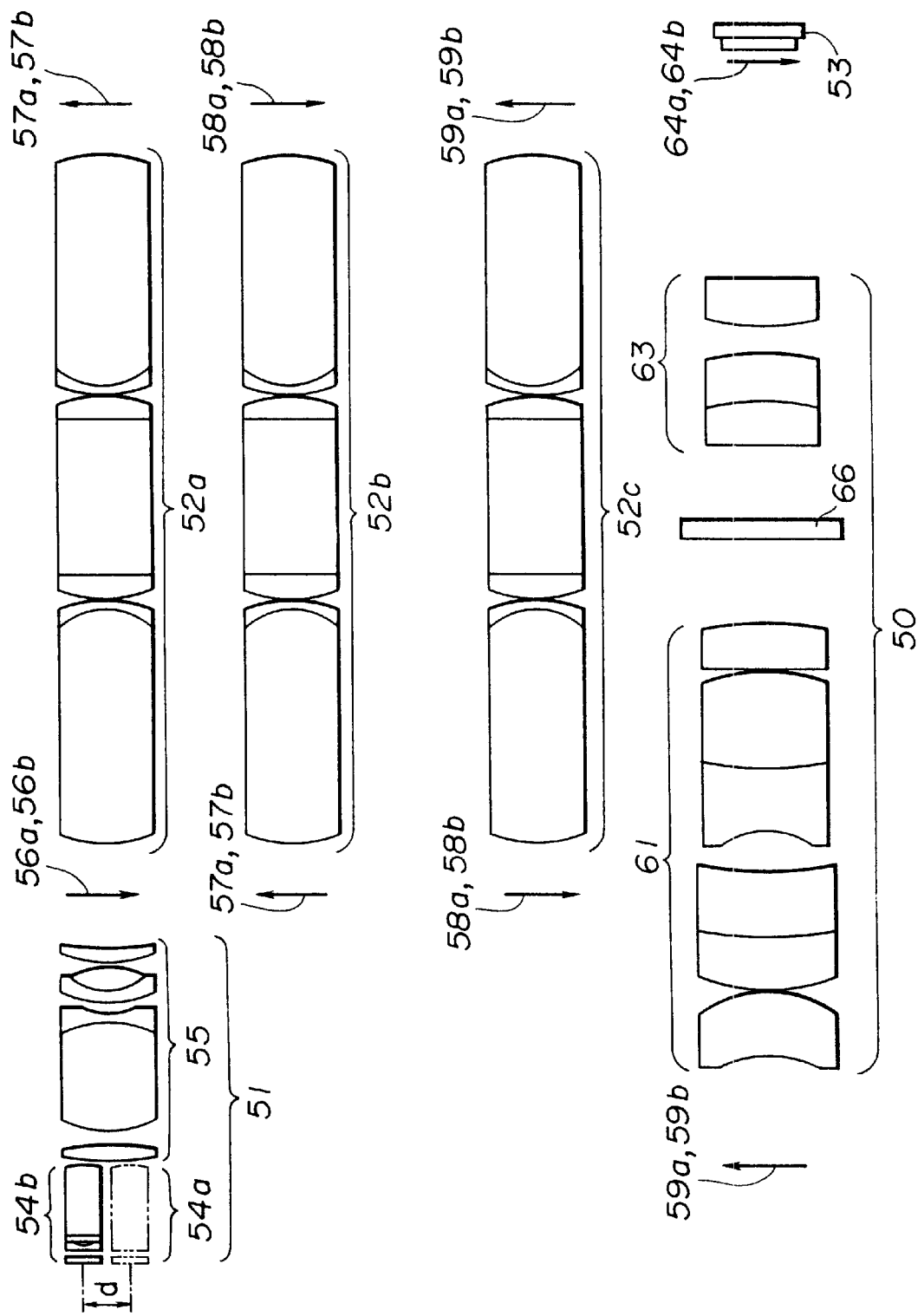
FIG. 24 is a formation view showing an image taking optical system in the thirteenth embodiment of the present invention.

FIG. 24 shows an image taking optical system in the thirteenth embodiment of the present invention. The final images 59a and 59b of the relay lens system are further once relayed by the adapter optical system 50. Because the adapter optical system 50 is of the same optical axis as of the relay lens system 52c, the relayed images 64a and 64b will be formed in substantially the same positions and will be taken by one common image taking device 53.

A shutter 66 is arranged between the pupil image forming lens system 61 and image forming lens system 63 and alternately intercept the beam so that two images may not be simultaneously formed in the image taking device 53.

This embodiment has an advantage in that only one image taking device 53 is required. The other effects are the same as in the twelfth embodiment.

The lens data of this embodiment are shown in Table 9.

Figure 25:
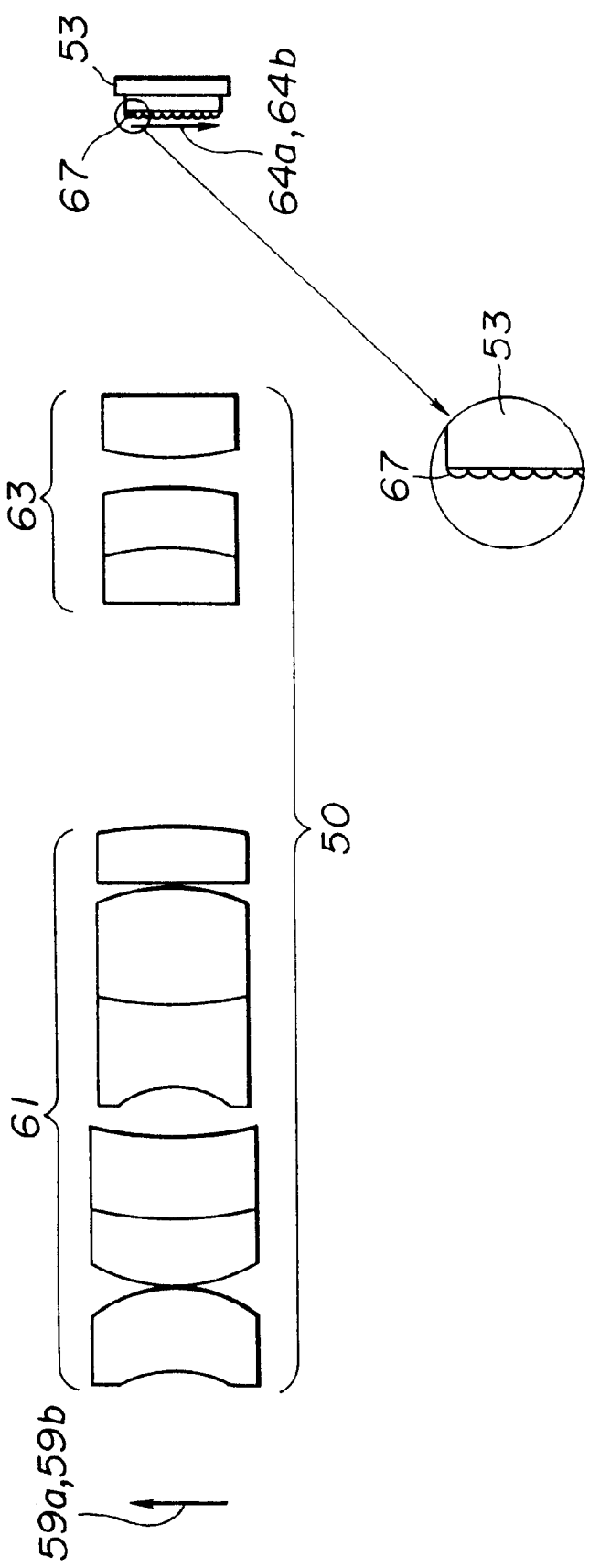
FIG. 25 is a formation view showing a main part of an image taking optical system in the fourteenth embodiment of the present invention.

FIG. 25 shows a main part of an image taking optical system in the fourteenth embodiment of the present invention. As in the thirteenth embodiment, because the adapter optical system 50 has the same optical axis as that of the relay lens system 52c, the relayed images 64a and 64b will be formed in substantially the same positions and will be taken by one image taking device 53.

A lenticular lens 67 is arranged just before the light receiving surface of this image taking device 53 which is commonly used. When the right and left images are formed at intervals of one row or one line by the image taking device 53, the two images will be separately taken. This embodiment has also an advantage in that only one image taking device 53 is required. The other effects are the same as in the thirteenth embodiment. By the way, the lens data of this embodiment are the same as in the thirteenth embodiment.

FIGS. 26A and 26B show an objective optical system in the fifteenth embodiment of the present invention. In this embodiment, the visual field direction is 30 degrees with the lengthwise direction of the endoscope (the optical axis direction of the relay lens). The reflecting prisms 68a, 68b and 69a, 69b forming the front groups 54a and 54b may be respectively two separate bodies or one integral body.

FIG. 27 shows an objective optical system in a modification of the fifteenth embodiment of the present invention. As in the fifteenth embodiment, a perspective objective optical system 70 is formed. In this modification, the visual field direction is 70 degrees with the lengthwise direction of the endoscope (the optical axis direction of the relay lens). The reflecting prisms 68a, 68b and 69a, 69b may be respectively two separate bodies or one integral body.

In the fifteenth embodiment and its modification, the visual field direction can be varied by varying the angles of the reflecting prisms 68a, 68b and 69a, 69b. Therefore, when the front group part is formed to be interchangeable, various visual field directions or visual field angles will be able to be obtained by interchanging only this front group. Needless to say, even when the entire objective optical system is formed to be interchangeable, the same effects will be obtained. The other effects are the same as in the tenth embodiment.

FIG. 28 shows an image taking optical system in the sixteenth embodiment of the present invention. As in the fifteenth embodiment, in this embodiment, the perspective objective optical system 70 is used. In this embodiment, the visual field direction is 45 degrees with the lengthwise direction of the endoscope (the optical axis direction of the relay lens). The reflecting prism 71 is integral on the right and left.

That is to say, in the illustrated tenth to fifteenth embodiments, the optical system divided into two parts of the front groups 54a and 54b is adopted. However, in this embodiment, a common reflecting prism 71 is used to form a front group 54 functioning the same as the two separated front groups 54a and 54b.

Negative lens systems 72a and 72b, such as negative power elements, and positive lens systems 73a and 73b, such as positive power elements forming the front group 54 on the left and right are formed in pairs as arranged eccentrically respectively on the left and right and are rotatable as illustrated. Therefore, the arranging direction of the two incident pupils of the objective optical system, that is, the direction of the parallax (the direction of d in FIG. 28) can be varied and it is very effective in permitting stereo-observing of an object in many directions.

In this embodiment, with the rotation of the negative lens systems 72a and 72b and positive lens systems 73a and 73b, the incident pupil of the pupil image forming lens system 61 will also rotate. In the embodiment shown in FIG. 28, the adapter optical system 50 shows an example in case the same formation as of the eleventh embodiment is adopted. The image forming lens systems 63a and 63b and the image taking devices 53a and 53b will synchronously rotate to prevent the beam from being intercepted.

Even in this embodiment, when the angle of the reflecting prism 71 is varied; the visual field direction will be able to be varied, when the combination of the focal distances of the negative lens and positive lens is varied, the visual field angle will be able to be varied; and when the optical axis distance between the negative lens and positive lens on the left and right is varied, the magnitude of the parallax will be able to be varied.

This embodiment can be applied to another adapter optical system. However, as mentioned above, with the rotation of the negative lens systems 72a and 72b and positive lens systems 73a and 73b, the projected pupil of the pupil image forming lens system 61 will also rotate. Therefore, it is necessary to rotate such parts having left and right separate optical axes as, for example, the mirror parts 62a and 62b, image forming lens systems 63a and 63b, image taking devices 53a and 53b and the like as synchronized in the tenth embodiment in FIG. 20. The other effects are the same as in the tenth embodiment.

FIG. 29 shows the seventeenth embodiment of the present invention wherein the front group 54 including the negative lens systems 72a and 72b and positive lens systems 73a and 73b is arranged on the object side of the reflecting prism 71.

In this embodiment, as the rotating parts in the front group 54 part can be concentrated in one place (in this case, on the object side of the reflecting prism 71) as compared with the sixteenth embodiment, the formation is simple. Also, FIG. 29 shows an example wherein the adapter optical system 50 having the same formation as that of the thirteenth embodiment is used. The opening part of the shutter 66 synchronously rotates so that the beam may not be intercepted. At this time, other parts such as the image forming lens 63 and image taking device 53 may also rotate together with the shutter 66.

FIG. 30 shows unit formations of the eighteenth embodiment of the present invention. In FIG. 30A, the unit formation comprises the front group unit 81 having the front groups 54a and 54b built-in, the rear group—relay lens system—pupil image forming lens system unit 82 having the rear group 55, relay lens systems 52a, 52b and 52c and pupil image forming lens system 61 built-in, the image forming lens system unit 83 having the image forming lens systems 63a and 63b built-in and the image taking device unit 84 having the image taking devices 53a and 53b built-in. By the way, the connecting part of the rear group—relay lens system—pupil image forming system unit 82 and the image forming lens system unit 83 corresponds to the border of the input section 25 and output section 24 shown in FIG. 5.

FIG. 30B shows a formation of the image forming lens system—image taking device unit 85 wherein, in FIG. 30A, the image forming lens systems 63a and 63b and image taking devices 53a and 53b are made as one unit.

FIG. 30C shows a formation in FIG. 30A of the objective optical system unit 86 combining the front groups 54a and 54b in the front group unit 81 and the rear group 55 in the rear group—relay lens system—pupil image forming lens system unit 82, the relay lens system—pupil image forming lens system unit 87 having the relay lens systems 52a, 52b and 52c and pupil image forming lens system 61 built-in and the image forming lens system—image taking device unit 85, the same as in FIG. 30B.

In FIG. 30D, the objective optical system (that is, the front groups 54a and 54b and the rear group 55), relay lens systems 52a, 52b and 52c and pupil image forming lens system 61 are formed of the objective optical system—relay lens system—pupil image forming system unit 88 and the image forming lens system—image taking device unit 85 are made as one unit.

In FIG. 30E, the objective optical system and relay lens systems 52a, 52b and 52c are formed of the objective optical system—relay lens system unit 89 made one unit and the pupil image forming lens system 61, image forming lens systems 63a and 63b and image taking devices 53a and 53b are formed of the pupil image forming lens system—image forming lens system—image taking device unit 90 are made as one unit.

In FIG. 30F, the front group unit 81, rear group 55 and relay lens systems 52a, 52b and 52c are formed of the rear group—relay lens system unit 91 and pupil image forming lens system—image forming lens system—image taking device unit 90 are made as one unit.

In FIG. 30G, the relay lens systems 52a, 52b and 52c are formed of the relay lens system unit 92, objective optical system unit 86 and pupil image forming lens system—image forming lens system—image taking device unit 90 are made as one unit. By the way, in FIGS. 30B to 30G, the lens system within each unit is shown with the reference numeral omitted.

Also, in FIGS. 30A to 30G, the ocular adapter 45' shown in FIG. 16D may be made connectable.

In FIG. 31, the front group unit 81 is explained further. FIG. 31A shows a front group unit 81 using a common front group 54. In case it is fitted, a pupil dividing type stereoendoscope in the related art will be able to be formed.

Figure 31A:
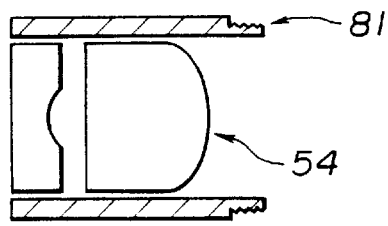
FIGS. 31A to 31F are views respectively showing actual formations of front group units.
Figure 31B:
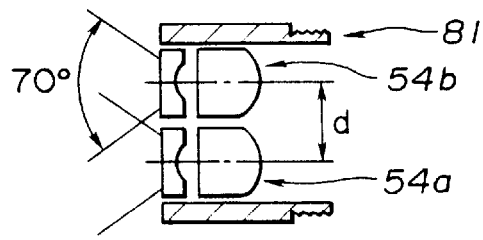
Figure 31C:
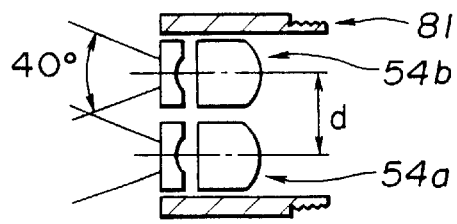

FIG. 31B shows the front group unit 81 of a visual field angle of 70 degrees. FIG. 31C shows the front group unit 81 of a visual field angle of 40 degrees. When they are replaced, any desired visual field angle will be obtained.

Figure 31D:
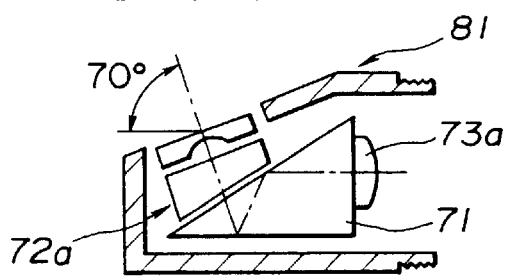
Figure 31E:
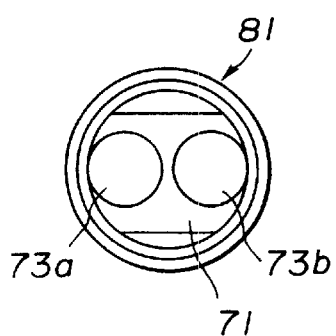

FIGS. 31D and 31E show a front group perspective unit 81 of a visual field direction of 70 degrees. FIG. 31E is a view as seen from the rear of FIG. 31D. When the reflecting prism 71 is replaced, the front group perspective unit 81 of any visual field direction will be able to be formed.

Figure 31F:
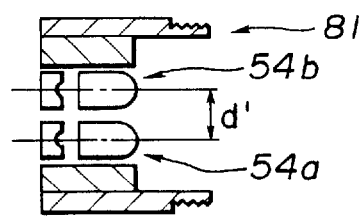

FIG. 31F shows the front group unit 81 in which the parallax is reduced and the optical axes of the front groups 54a and 54b are brought close to each other to make the distance d' smaller than the other optical axis distance d. In FIGS. 31A to 31F, if the beams from the front groups 54a and 54b are made substantially a focal beams, when the unit is displaced, a focus lag and image lag will be able to be controlled.

FIG. 32 shows a formation of the objective optical system unit.

Figure 32A:
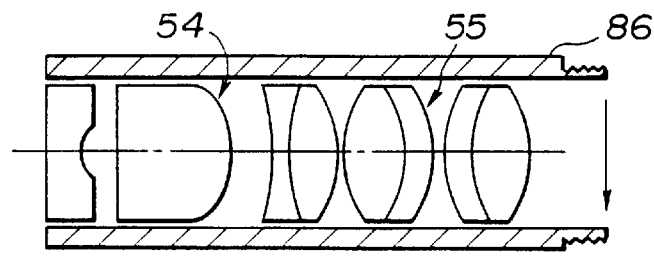
FIGS. 32A to 32F are views respectively showing actual formations of objective optical system units.
Figure 32B:
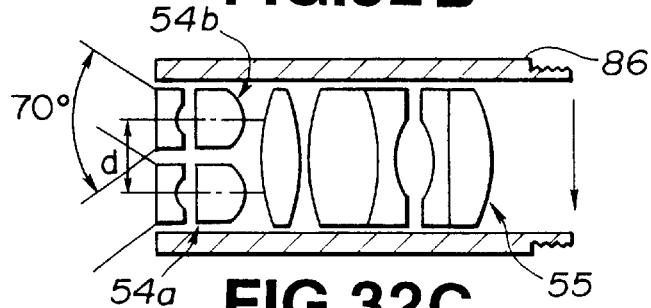
Figure 32C:
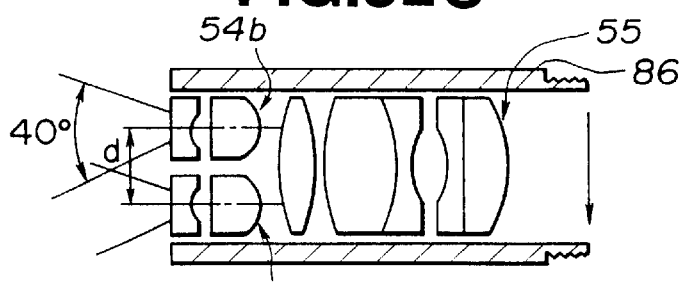

FIG. 32A shows an objective optical system unit 86 comprising the front group 54 and rear group 55 arranged to share the same optical axis. When it is used, the pupil dividing type stereoendoscope in the related art will be able to be formed. FIG. 32B shows an objective optical system unit 86 having the front groups 54a and 54b of a visual field angle of 70 degrees. FIG. 32C is of an objective optical system unit 86 having the front groups 54a and 54b of a visual field angle of 40 degrees. When these are replaced, any desired visual field angle will be obtained.

Figure 32D:
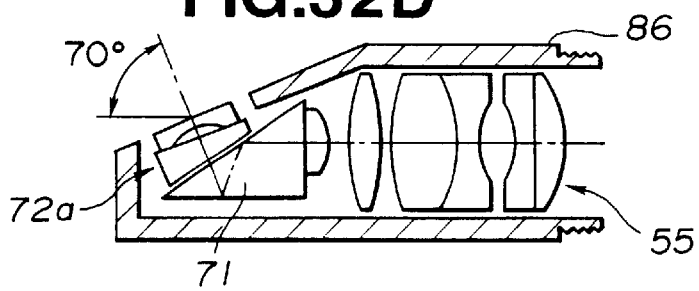
Figure 32E:
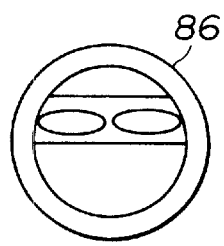

FIG. 32D is of a perspective objective optical system unit 86 of a visual field direction of 70 degrees. FIG. 32E is a front view of FIG. 32D. When the reflecting prism 71 is replaced, a perspective objective optical system unit of any visual field direction will be able to be formed. By the way, in FIG. 32E, the light guide is omitted.

Figure 32F:
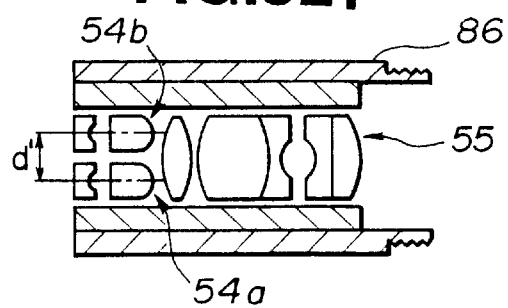

FIG. 32F shows an objective optical system unit in which the parallax is reduced and the optical axes of the two front groups 54a and 54b are brought close to each other so that the optical axis distance d' may be smaller than d, for example, in FIG. 32B and others.

FIG. 33 shows a formation of a unit including the rear group 55, relay lens systems 52a and 52b and pupil image forming lens system 61.

Figures 33A, 33B, 33C, 33D:
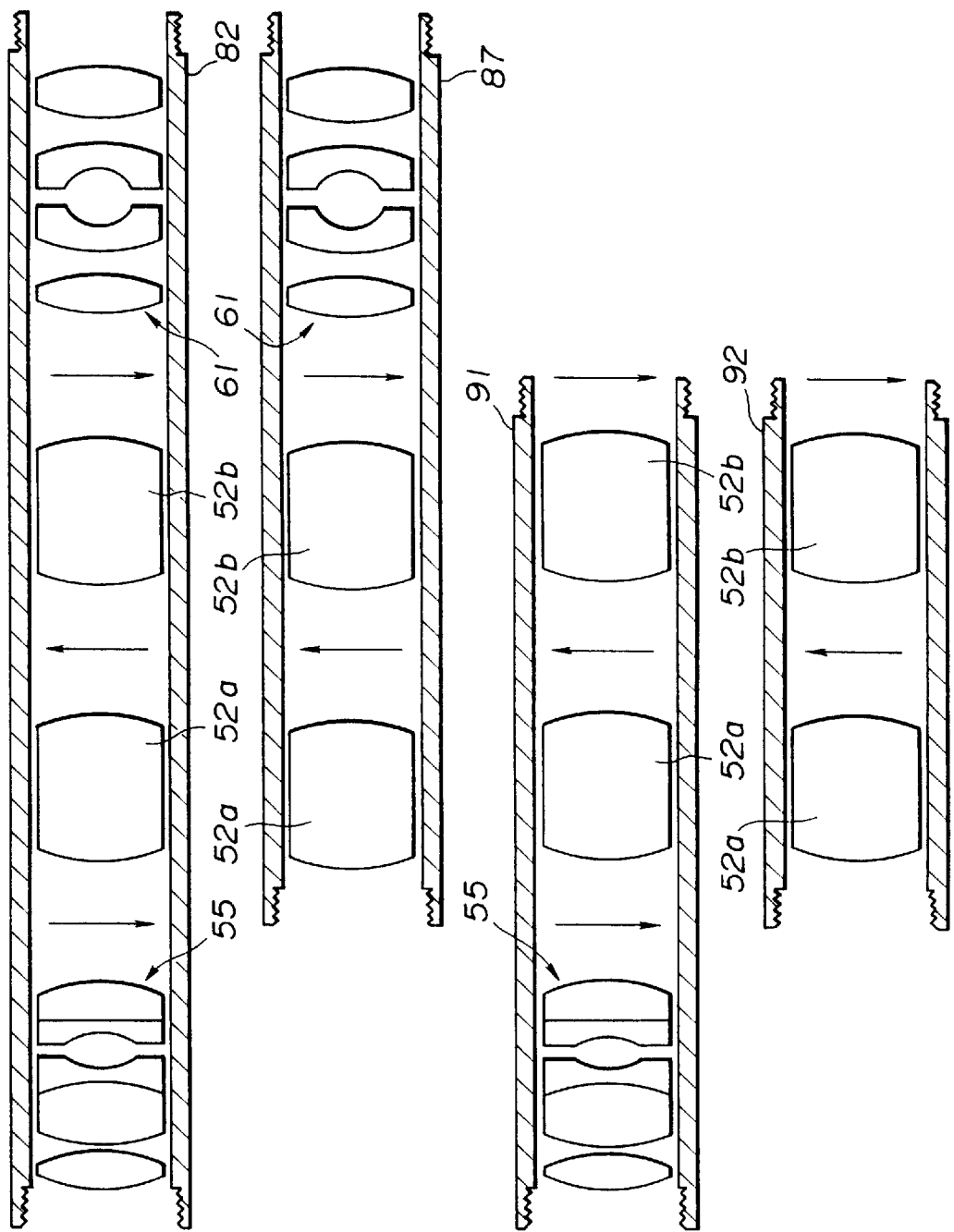

FIG. 33A shows the rear group—relay lens system—pupil image forming lens system unit 82 including the rear group 55, relay lens systems 52a and 52b and pupil image forming lens system 61. FIG. 33B shows the relay lens system—pupil image forming lens system unit 87 including the relay lens systems 52a and 52b and pupil image forming lens system 61. FIG. 33C shows the rear group—relay lens system unit 91 including the rear group 55 and relay lens systems 52a and 52b. FIG. 33 shows the relay lens system unit 92 comprising the relay lens systems 52a and 52b.

Any number of relaying times of the relay lens system can be used. As required, different lengths for the inserted section different can be selected.

The respective units in the eighteenth embodiment can be formed by adopting a part of the optical system of the tenth to seventeenth embodiment.

According to the eighteenth embodiment, the stereoendoscope of the formation adapted to the using object can be selected and used. The other effects are the same as in the tenth to seventeenth embodiments.

The following nineteenth and twentieth embodiments are embodiments wherein formations (a) in the means and operations for solving the above mentioned problems are used. When a plurality of images taken in by an objective optical system and having a parallax between them are transmitted by a common image transmitting optical system, are taken and are selectively displayed by a displaying means, optimum stereo-images will be provided.

FIG. 34A shows a formation of a stereoendoscope apparatus 101 provided with the nineteenth embodiment of the present invention and an operation made by using the stereoendoscope 102 of the nineteenth embodiment. FIG. 34B shows an arrangement of an objective optical system 121 as seen from the distal end surface of the stereoendoscope 102.

This stereoendoscope apparatus 101 comprises a stereoendoscope 102 having an image taking means for taking a plurality of images having a built-in parallax, a CCU 103 processing signals for this imaging means, a distributor 104 connected to this CCU 103 and distributing video signals, a color monitor 105 as plural displaying means displaying the video signals distributed by this distributor 104 and head mounted displays (abbreviated as HMD's) 106 and 107.

In FIG. 34A, a rigid inserted section 111 of the stereoendoscope 102 is inserted toward an affected part 114 from a hole 113 in an abdominal part 112 of a patient. Two operators 115 and 116 respectively fit HMD's to their head parts, observe the affected part 114 with stereo-inspection and treat the affected part 114 by using treating tools 117 and 118. The treating tools 117 and 118 may be inserted through other holes or through channels in the stereoendoscope 102.

Also, another observer 119 (an assistant, nurse or spectator) observes the same affected part with stereo-inspection by observing the color monitor 105 with shutter spectacles 120 fitted.

The stereoendoscope 102 comprises an objective optical system 121, relay optical system 122, adapter optical system 123 and image taking means 124 in the order mentioned from the object side.

At least three images having a parallax between them and formed by the objective optical system 121 are transmitted by one (or plural) relay optical system 122 and are spatially (or timely) separated and formed by respective image taking devices forming the image taking means 124. The electrical signals of the respective images photoelectrically converted by the image taking means 124 are converted to video signals by the CCU 103, are further divided into signals of any two images by the distributor 104 and are displayed by the color monitor 105 and HMD's 106 and 107 which are to be displaying means.

In this embodiment, when the various optical systems shown so far are used as combined with the objective optical system 121 and adapter optical system 123, the stereo-image optimum to the respective operators and observers will be able to be effectively provided.

When a plurality of images are transmitted by one relay optical system built-in in one tubular inserted section 111, only one hole 113 in the abdominal part 112 is required and the burden on the patient will be able to be reduced.

As shown, for example, in FIG. 34B, the objective optical system 121 is formed of six objective lens systems 121a to 121d arranged in the positions separated by a fixed distance from the center axis at an angle of 60 degrees from the center axis of the inserted section. The six images by these objective lens systems 121a to 121f are taken, for example, by six image taking devices forming the image taking means 124 through the common relay optical system 122 and the adapter optical system 123 formed, for example, of three adapter lens systems.

According to this formation, by selecting the image, for example, by the objective lens systems 121a and 121d, a stereo-image having a large parallax can be obtained and, by selecting the image by the objective lens systems 121b and 121e, a stereo-inspection having a large parallax in the direction different by 60 degrees is possible. Further, by selecting the image by the objective lens systems 121c and 121f, a stereo-inspection having a large parallax in the direction different by 120 degrees is possible.

Further, by the combination in the above mentioned case, the parallax will become small. However, by selecting the image, for example, by the objective lens systems 121a and 121c or the objective lens systems 121a and 121e, an image having a stereo-feel in various directions can be obtained.

By the way, a remote display selecting means whereby the operator 115 using the displaying device can remotely select the two images distributed by the distributor 104 to the displaying device side of the HMD 106 or the like by a wireless remote controlling apparatus using infrared rays or ultrasonic waves may be provided.

An observing direction displaying means is provided whereby, in case the image by the objective lens systems (for example, 121b and 121e) in the parallax direction different from the parallax direction of a set of objective lens systems (for example, 121a and 121d) as a reference is selected, the parallax direction changing angle (in this case, 60 degrees) will be displayed when the displaying device so that the direction in which the operator 115 or the like is observing may be simply found.

By the way, in this embodiment, n (at least three or more) (in FIG. 34, n=6) objective images are transmitted by one relay optical system 122 but may be transmitted by n-i relay optical systems (here, i=1 to n−1).

FIG. 35 shows a formation of the stereo-endoscope 131 of the twentieth embodiment of the present invention. FIG. 35A shows a general formation of the stereoendoscope 131. FIG. 35B shows an elevation as seen from the distal end surface in FIG. 35A. FIG. 35C shows an arrangement of image taking devices as seen from the front surface side in FIG. 35A. In this embodiment, too, several sets of stereo-images can be obtained.

Several front groups 133 (133a to 133f) forming an objective optical system 132 arranged on the distal end side of the rigid inserted section 111 take in images having a parallax between them and an image 135 is formed in substantially superimposed positions by one common rear group 134, is relayed several times by one common relay optical system and becomes a final image 137.

This final image 137 is of several superimposed images. These images have their pupils spatially separated by a pupil image forming lens system 138 and, further, respective images 141 (141a to 141f) are formed on CCD's 140 (140a to 140f) by image forming lenses 139.

In this embodiment, six images having a parallax between them can be obtained. When two of the images are selected and displayed, the images having various stereo-feels and parallaxes will be able to be stereo-inspected. Also, several persons can stereo-observe in separate directions.

FIGS. 36A to 36F show distal end side formations of the stereoendoscope of the twenty-first embodiment of the present invention. FIG. 36B is an elevation of FIG. 36A. FIG. 36C shows an optical system as seen from the side of FIG. 36A. FIG. 36D is an elevation of FIG. 36C. FIG. 36E shows FIG. 36C as bent. FIG. 36F is an elevation of FIG. 36E.

In this embodiment, the inserted section 152 can be bent on the distal end side.

A front group optical system 153, a rear group 154a forming a relay optical system 154 and a relay lens system 154b are arranged from the distal end side within the inserted section 152. The distal end section 155 of the inserted section covering the objective optical system 153 is formed of a tubular frame having a curvable hose structure. The proximal side from the relay optical system 154 is formed of a rigid tubular frame.

Mirrors 158 and 159 are arranged between concave lenses 156a and 156b as of a front group and convex lenses 157a and 157b forming the objective optical system 153 and are rotatable respectively around axes 161 and 162.

When the mirrors 158 and 159 are rotated simultaneously with curving from the straight seen state in FIG. 36C, the distal end section 155 will be curved to be bent as in FIGS. 36E and 36F. According to this embodiment, the observation can be made with the distal end section bent. The other effects are the same as in the first embodiment and others.

FIG. 37 shows a formation on the distal end side of the stereoendoscope of the twenty-second embodiment of the present invention. This embodiment is a combination of the twentieth embodiment wherein several sets of stereo-images can be obtained and the twenty-first embodiment having a bendable structure.

Usually, in an endoscope operation, the endoscope does not enter directly into the abdominal part but is inserted instead through a tragacanth 171. The thinner the tragacanth 171, the less the distress of the patient. On the other hand, in case several operators jointly operate, the observation can conveniently be made in the separate respective directions.

However, there is a limit to how much the parallax may be increased and the parallax can not be made greater than the outside diameter of the distal end section. This embodiment can cope with such circumstances and makes it possible to observe in separate directions.

In this embodiment, two bendable distal end sections 155 and 155' are provided forward of the relay optical system 154 and objective optical systems 153 and 153' of the same structure as in the twentieth embodiment in FIG. 36 are contained within the respective distal end sections 155 and 155'. The same members as shown in FIG. 36 within the distal end section 155 shall bear the same reference numerals, the same members as shown in FIG. 36 within the other distal end section 155' shall bear the same reference numerals fitted with ' and their explanation shall be omitted.

According to this embodiment, when the distal end section is inserted within the tragacanth 171, it will be seen as straight as in FIG. 36C. When the distal end section comes out of the tragacanth 171, it will be bent as in FIG. 37A and several observers will be able to observe in separate directions through one thin relay optical system 154.

By the way, for example, in the first embodiment, each of the objective optical systems 21a and 21b may be formed of an anamorphic optical system wherein the image forming magnification in the horizontal direction can be made smaller than the image forming magnification in the vertical direction (intersecting at right angles with this horizontal direction).

In the case of this formation, particularly, in case a common image taking device 23 is adopted, the two right and left images will be able to be prevented from being superimposed and the right and left image taking ranges in the image taking device 23 will be able to be substantially expanded.

In the function of transmitting images by the relay optical system 22, because the right and left images can be intercepted less than in the case of no anamorphic optical system, that much, the objective optical systems 21a and 21b will be able to be arranged as having increased separation from each other (with the optical axis distance d larger) and a picture image having a higher stereo-feel will be able to be obtained.

In this case, in the CCU 4, the signal of extending the picture image in the horizontal direction or compressing the picture image in the vertical direction may be processed.

By the way, the relay optical system 22 may be also formed of an anamorphic optical system Even in the other embodiments, the objective optical system, relay optical system and adapter optical system may be formed of anamorphic optical systems.

By the way, in the lens data of the respective embodiments, in case the same lenses are paired in the objective optical system, adapter optical system and the like, only the lens data of one of the pair will be shown. In the respective embodiments, the relay lens optical system formed of a homogeneous bar-like lens is shown. However, even in case a refractive index distributing type lens is formed of such non-homogeneous rod as of a Shelphock (trade name) and is used for the relay optical system (image transmitting optical system), the present invention will be effective.

By the way, the embodiment wherein a plurality of images having a parallax are formed in spatially separated positions by the objective optical system and the embodiment wherein a plurality of images having a parallax are formed in spatially substantially coinciding positions have been explained above. However, the case of their intermediate functions, that is, the case where a plurality of images having a parallax are formed in spatially at least partly superimposed positions and the case that a plurality of images having a parallax are formed in spatially at least partly separated positions belong to the present invention. Also, the case of applying an image by an objective optical system to the case that the image by the objective optical system is transmitted by such image transmitting optical system as the relay optical system belongs to the present invention.

As explained above, as the stereoendoscope in the fist to twenty-second embodiments is provided with an objective optical system having a plurality of incident pupils formed in different positions and forming a plurality of images having a parallax between them having passed through these plural incident pupils and a common image transmitting optical system transmitting the plural images having a parallax between them, the parallax will be able to be made large by the optical system, a sufficient stereo-feel will be obtained, the parts of the light path transmitting a plurality of images will be able to be made common by making the image transmitting optical system common, the number of the parts will be able to be reduced and the dispersion of plural images by production errors will be able to be extremely prevented.

When a stereoendoscope is formed by providing a plurality of objective optical systems arranged in parallel, separating plural images having a parallax and forming images and a common image transmitting optical system transmitting the plurality of images, the parallax will be able to be made large by the optical system, a sufficient stereo-feel will be obtained, the parts of the light path transmitting the plurality of images will be able to be made common by making the image transmitting optical system common, the number of the parts will be able to be reduced and the dispersion of plural images by production errors will be able to be extremely prevented. Further, as the images transmitted by the image transmitting optical system are spatially separated, the stereo-section will be made possible by the image taking means and ocular optical system without using an image separating means.

Also, when a stereoendoscope is formed by providing several front group optical systems, common rear group optical systems forming objective optical systems forming a plurality of images having a parallax in spatially substantially coinciding positions and a common image transmitting optical system transmitting the plurality of images, the parallax will be able to be made large by the optical system, a sufficient stereo-feel will be obtained, the parts of the light path transmitting the plurality of images will be able to be made common by making the image transmitting optical system common, the number of the parts will be able to be reduced and the dispersion of the plurality of images by production errors will be able to be extremely prevented. When a common rear group optical system is used in the objective optical system part, many parts will be able to be used in common and a plurality of picture images less influenced by production errors and high in quality will be obtained.

Further, there is a stereo-inspectable endoscope in U.S. Pat. No. 5,191,203 shown in FIG. 38A wherein an objective optical system 500 is formed of collimator lenses 501 and a pair of left and right image forming lenses 502a and 502b arranged in the order mentioned from the object side.

In the objective optical system of the stereoendoscope of this related art, there are the following three problems:

(1) When the picture angle is to be made large, the inward angle will not be able to be made large and the stereo-feel will reduce.

Figure 38A:
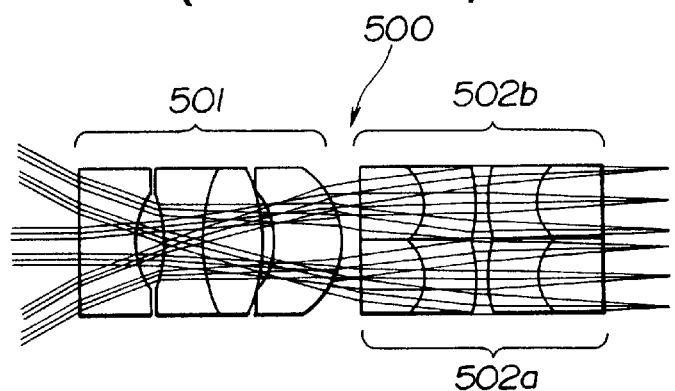
FIGS. 38A and 38B relate to a prior example, where
Figure 38B:
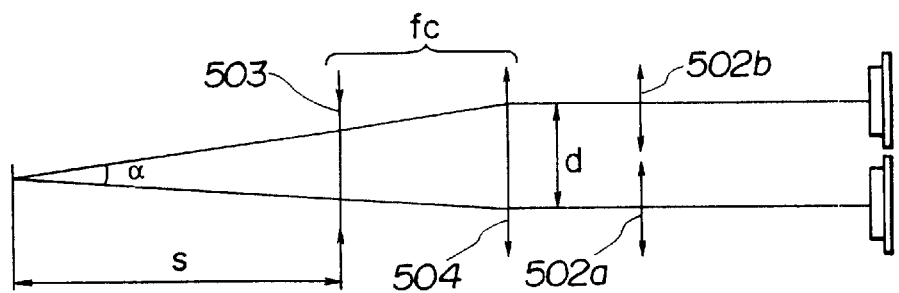

As in FIG. 38B, in case the picture angle is to be made large, it will be necessary that the power arrangement of the collimator lenses 501 will be negative and positive in the order from the object side. When the power of the negative lens 503 on the object side is made large, the picture angle will be able to be made large. However, in this case, the focal distance fc of the collimator lenses 501 will become larger than the object distance s and the inward angle α will become small by the following formula:

$$\alpha = 2 \cdot \arctan (d/2fc)$$

wherein d represents an optical axis distance between the two image forming lenses 502a and 502b.

(2) A relative error between the left and right images is likely to occur.

The relative error between the right and left images is produced mostly in the parts of the left and right separate bodies by a surface shape error, surface distance error, eccentricity error or the like between right and left independent lens systems. In the prior example, the parts of the left and right separate bodies (the parts having left and right separate optical axes) correspond to the image forming lenses 502a and 502b which are so many that an error is likely to occur. When a relative lag (focusing, eccentricity or the like) is produced between the left and right images, the left and right images will become difficult to resolve, resulting in fatigue.

(3) It is difficult to adjust the eccentricity error of the left and right images.

In order to adjust the eccentricity error of the left and right images, the lens or CCD of the left and right separate body parts must be adjusted. However, in the prior example, either the lens or the CCD is in a position through the other part (in this case, the collimator lens 501) from the distal end section of the endoscope and is difficult to adjust.

The twenty-third to twenty-fifth embodiments provide a stereoendoscope wherein the picture angle and stereo-feel (inward angle) can be set to be optimum, the error between the left and right images is small and is easily adjustable, resulting in less fatigue, which shall be explained below.

In the stereoendoscope of these embodiments, there are an elongate inserted section, an objective optical system arranged within the distal end of the inserted section and an image taking means arranged within the inserted section for taking object images formed by the objective optical system. The objective optical system is formed of two negative lenses and one coaxial positive lens arranged in parallel with each other in the order mentioned from the object side. The inward angle is determined by the optical axis distance between the two negative lenses, therefore the picture angle and stereo-feel (inward angle) can be set to be optimum, the error between the left and right images is small and is easy to adjust and the fatigue feel can be reduced. in the stereoendoscope having an elongate inserted section.

In the twenty-third embodiment, the objective optical system is applied to a so-called electronic scope having a CCD in the distal end part of the inserted section of the endoscope.

Figure 39:
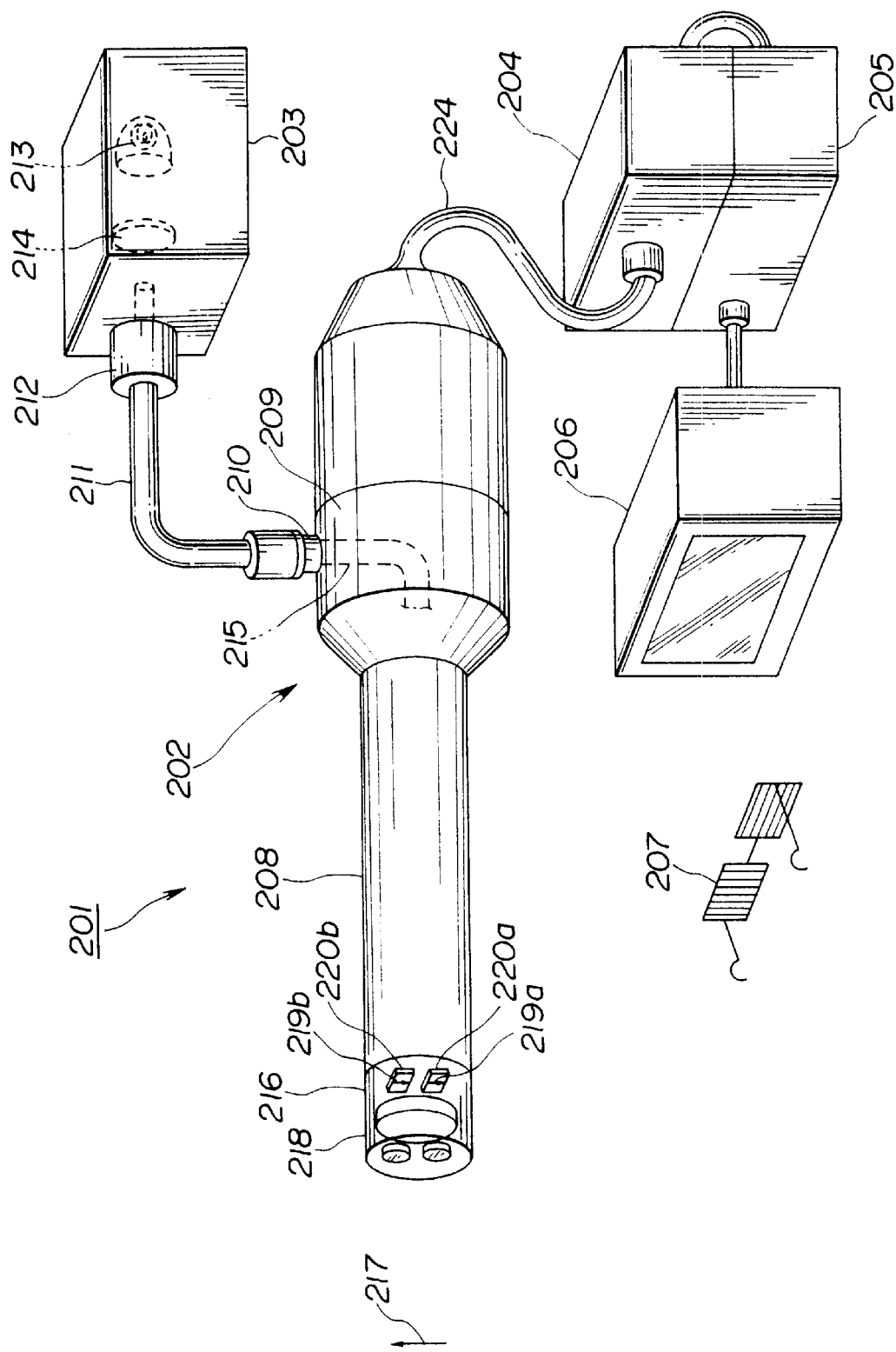
FIGS. 39 to 42 relate to the twenty-third embodiment of the present invention, where

As shown in FIG. 39, a stereoendoscope apparatus 201 comprises a stereoendoscope 202 of the twenty-third embodiment having an image taking optical system for stereo-inspection built-in, a light source apparatus 203 feeding an illuminating light to an illuminating light transmitting means transmitting the illuminating light and provided in this stereoendoscope 202, a camera controlling unit (abbreviated as CCU hereinafter) processing signals for an image taking means built-in in this stereoendoscope 202, a scan converter 205 converting to a video signal the signal put out of this CCU 204, a color monitor 206 displaying the video signal put out of this scan converter 205 and shutter spectacles 207 having a shutter function of stereo-perceiving the picture image displayed by this color monitor 206.

The stereoendoscope 202 has an elongate inserted section 208 to be inserted into a body cavity or the like and a gripped section 209 to be gripped by the operator and formed to be thick at the proximal end of this inserted section. This inserted section 208 is formed of a cylindrical metallic hose high in the flexibility and a soft jacket tube made of a metallic mesh and resin or the like. The distal end section 216 of the inserted section 208 is formed of a cylindrical rigid jacket tube made of such metal as stainless steel. An objective optical system 218 and two image taking devices 220a and 220b (for example, CCD's) are enclosed in the distal end section 216. By the way, the entire inserted section may be formed of a rigid jacket tube, just as in the distal end section.

This stereoendoscope has a light guide 215 as an illuminating light transmitting means transmitting the illuminating light fed from the light source apparatus 203 and an illuminating optical system (not illustrated) for emitting the transmitted illuminating light through an illuminating window just as in the ordinary endoscope. Two observed images having a parallax are obtained so that the object illuminated by this illuminating optical system may be stereo-inspected and has an observing optical system comprising the optical system 218 and two image taking devices 220a and 220b.

By the way, this embodiment includes an example wherein two images having a parallax are formed by the image taking devices 220a and 220b having a photoelectrically converting function as an observing optical system and is therefore also called an image taking optical system.

The gripped section 209 is provided with a light guide mouthpiece 210 to which a light guide cable 211 is removably connected at one end. A light guide connector 212 at the other end of the light guide cable 211 is removably connected to the light source apparatus 203.

A lamp 213 generating a white illuminating light and a lens 214 condensing this white light are arranged within the light source apparatus 203. The illuminating light condensed by this lens 214 is radiated on the end surface of the light guide connector 212, is transmitted by the light guide within the light guide cable 211, is transmitted from the light guide mouthpiece 210 to the light guide 215 side within the stereoendoscope 202 and is fed.

The light guide 215 as an illuminating light transmitting means is bent within the gripped section 209 and is inserted through the inserted section 208. This light guide 215 transmits the fed illuminating light and emits the illuminating light forward from the distal end surface fixed to the distal end section 216 of the inserted section 216.

An object (indicated by the arrow in FIG. 39) 217 illuminated by this illuminating light has optical images (219a and 219b in FIG. 39) having a parallax between them formed in image forming positions by the objective optical system 218 fitted to an observing window arranged adjacently to the illuminating window within the distal end section. These images 219a and 219b are formed on the photoelectric converting surfaces (image taking surfaces) of the image taking devices 220a and 220b arranged the same within the distal end of the inserted section.

Figure 40:
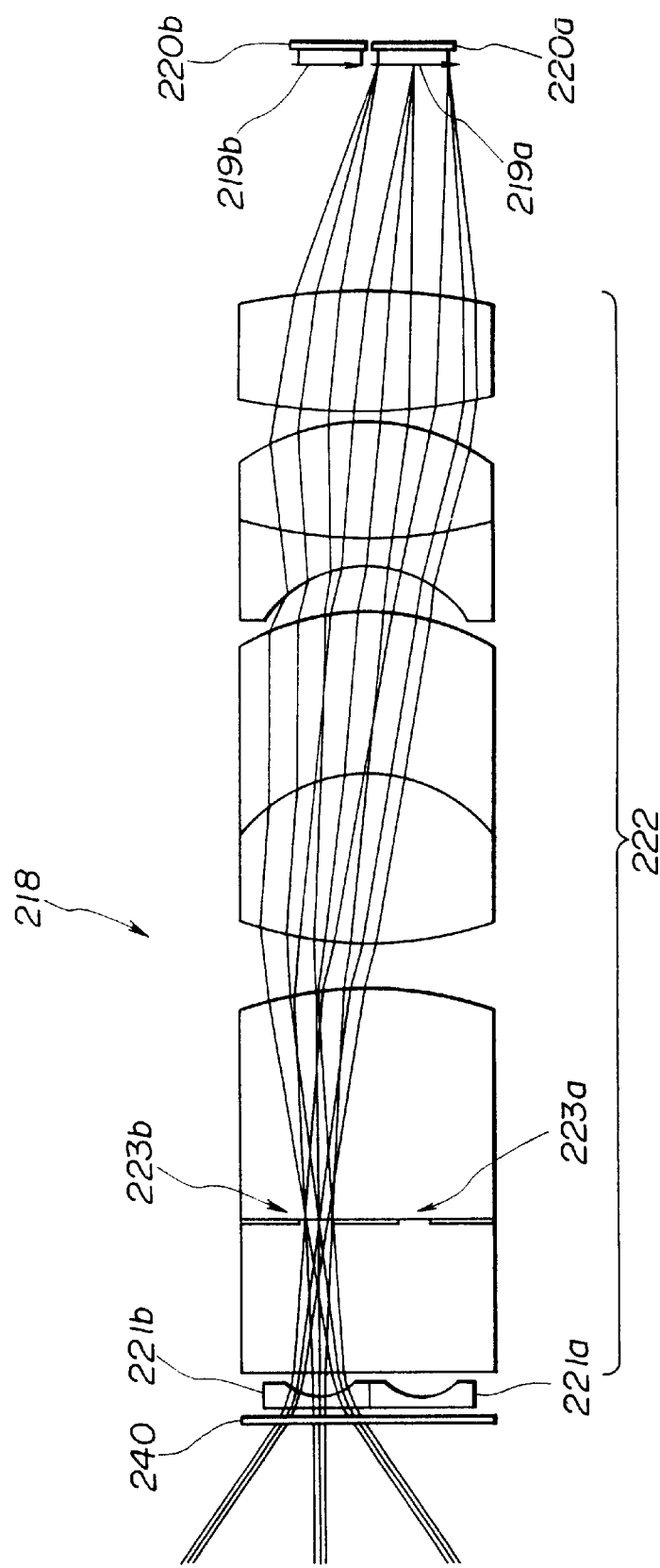

As shown in FIG. 40, the objective optical system 218 is formed of left and right separate negative lenses 221a and 221b and an axially symmetrical positive lens group 222 arranged in parallel with each other in the order mentioned from the object side. The light passing through a diaphragm opening 223b of the light from the object forms an image on the image taking device 220a and the light having passed through a diaphragm opening 223a forms an image on the image taking device 220b. By the way, a cover glass 240 made of parallel plane plates is arranged on the object side of the negative lenses 221a and 221b.

Here, the lens data of the objective optical system 218 of this embodiment are shown in Table 10.

In FIG. 39, the image taking devices 220a and 220b have, for example, square image taking surfaces. The vertical or horizontal direction of this image taking surface coincides with the horizontal direction in which the two diaphragm openings 223a and 223b are separated and arranged.

The image taking devices 220a and 220b are extended out and are connected with the CCU 204 by the signal cable 224. The image taking signal photoelectrically converted by the image taking devices 220a and 220b is processed in the CCU 204. The image signal processed in this CCU 4 is further put into a scan converter 205 and is converted to a video signal. The video signal is put out in a color monitor 206 in which the picture images having a parallax between each other and separately formed through the two diaphragm openings 223a and 223b are alternately displayed and the operator can observe and stereo-inspect the picture images with the shutter spectacles.

Figure 41:
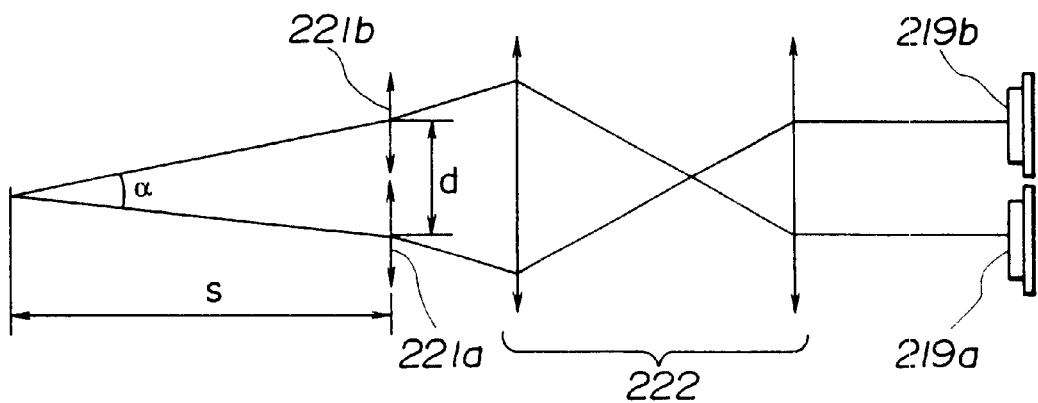

FIG. 41 shows a power arrangement of the objective optical system 218 in this embodiment. The inward angle α determining the magnitude of the stereo-feel is as follows from the optical axis distance d between the two negative lenses 221a and 221b and the object distance s:

$$\tan(\alpha/2) = d/(2s).$$

That is to say, as shown in FIG. 41, the inward angle of the objective optical system in this embodiment is determined by the optical axis distance d between the two negative lenses and does not depend on the picture angle. Further, as the left and right separate parts are only the negative lenses 221a and 221b, no relative error will be likely to be produced. Therefore, there can be obtained the following results:

(1) As the inward angle is determined by the optical axis distance between the two negative lenses and the inward angle and picture angle can be independently set, the picture angle will be able to made large with the inward angle kept large.

(2) As the main cause of the relative error between the left and right images is only the negative lens, the relative error between the left and right images will be little.

(3) As the left and right separate parts for adjusting the error between the left and right images are on the distal end side of the endoscope, they will be easy to adjust.

Figure 42:
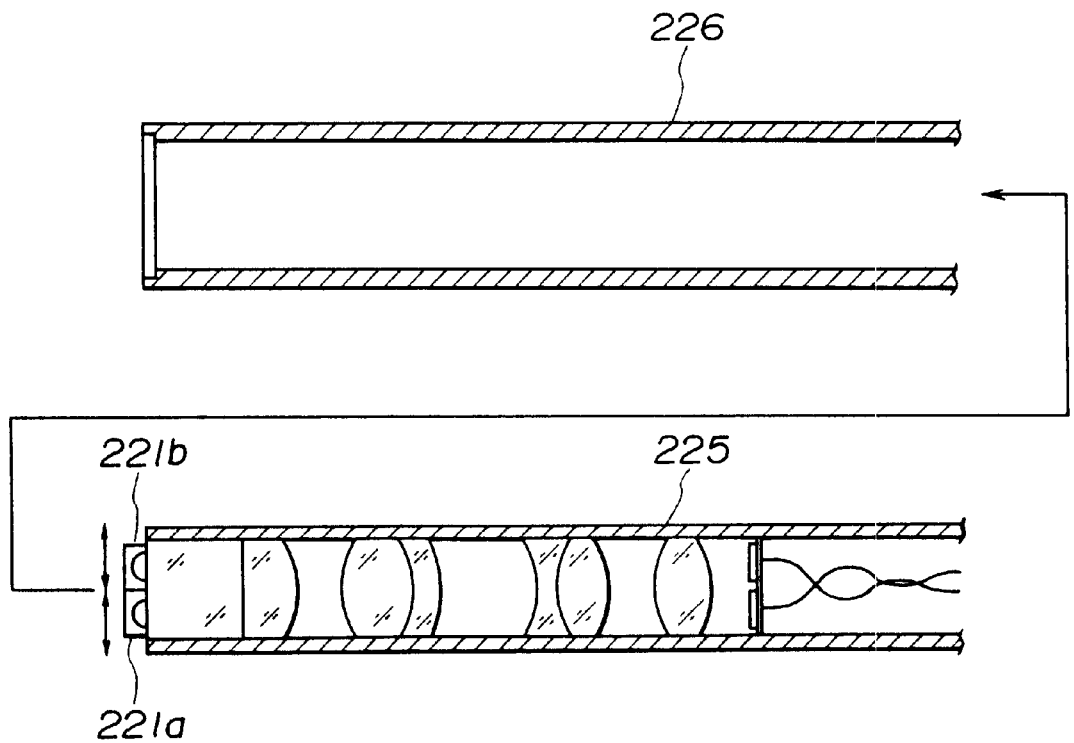

FIG. 42 shows a frame structure of the distal end section 216 of the stereoendoscope 202 in this embodiment. The frame structure comprises an inner tube 225 holding lenses and a CCD and an outer tube 226 enclosing the inner tube 225, an illuminating light guide and forceps channel not illustrated.

In the objective optical system of the prior example in FIG. 38A, as the left and right separate bodies for adjusting the eccentricity of the left and right images are in the positions through the collimator lens from the distal end within the inner tube, when they are to be adjusted, adjusting grooves, screws and adjusting spaces will have to be prepared in the inner tube and the inner tube will not be able to be made the inner tube 25 of such simple structure as in FIG. 42 and will be large in the outside diameter.

On the other hand, in this embodiment, as the two negative lenses 221a and 221b which are the left and right separate parts to be adjusted are outside the distal end of the inner tube 225, the positions of the negative lenses 221a and 221b will be able to be simply adjusted without requiring a special structure for the inner tube 225. The negative lenses 221a and 221b are adjusted in the position and are then bonded and fixed and the inner tube 225 is inserted into the outer tube 226 to complete the stereoendoscope.

The twenty-fourth embodiment shall be explained in the following with reference to FIG. 43. As the twenty-fourth embodiment is substantially the same as the twenty-third embodiment, only the different formations shall be explained.

In the twenty-fourth embodiment, the objective optical system of the stereoendoscope according to the present invention is applied to a so-called rigid endoscope wherein an image is transmitted to the proximal side by an objective optical system 218 and a transmitting optical system 227 arranged in an inserted section consisting of a cylindrical rigid jacket tube and is taken.

Figure 43:
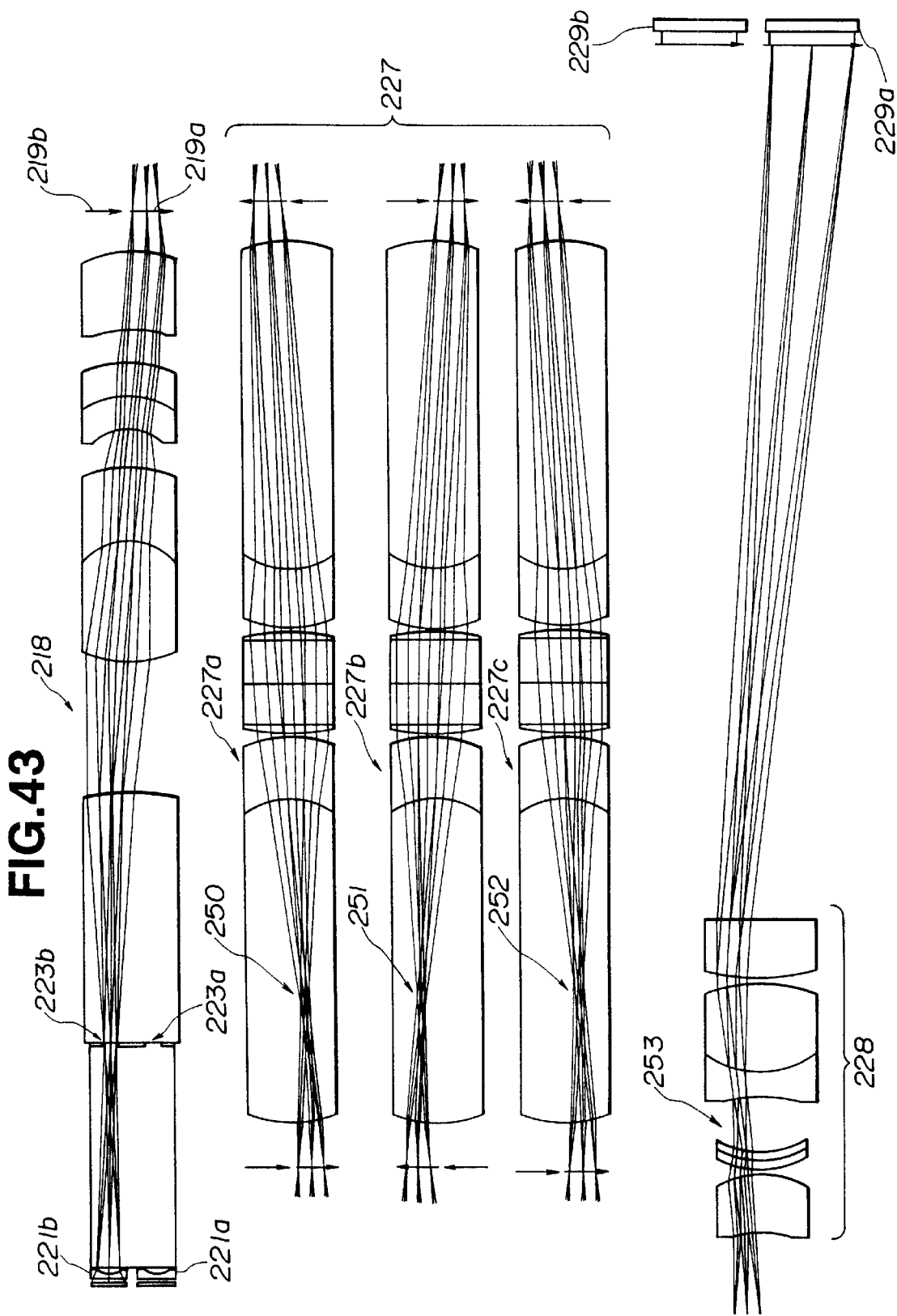
FIG. 43 is a formation view of the objective optical system and image transmitting optical system relating to the twenty-fourth embodiment of the present invention.

As shown in FIG. 43, images 219a and 219b formed by the objective optical system 218 are relayed by relay lenses 227a, 227b and 227c which are of a transmitting optical system 227 and are then formed on CCD's 229a and 229b by an image taking lens 228. All the lenses other than the negative lenses 221a and 221b at the distal end are coaxial. The images, that is, pupils of the diaphragm openings 223a and 223b are transmitted respectively to positions 250, 251, 252 and 253. The other formations, operations and effects are the same as in the twenty-third embodiment.

Here, the lens data of the objective optical system 218 and transmitting optical system 227 in this embodiment are shown in Table 11.

The image taking lens 228 in this embodiment is one coaxial lens system but the two pupils are separated in the position 253. Therefore, as the image forming lens of the image taking lens shown in the following, image forming lenses arranged in parallel with each other may be used after the pupil 253 to form images.

The twenty-fifth embodiment shall be explained in the following with reference to FIGS. 44 and 45. As this embodiment is substantially the same as the twenty-fourth embodiment, only the different formations shall be explained.

The twenty-fifth embodiment is an embodiment as applied to a rigid endoscope just as in the twenty-fourth embodiment.

Figure 44:
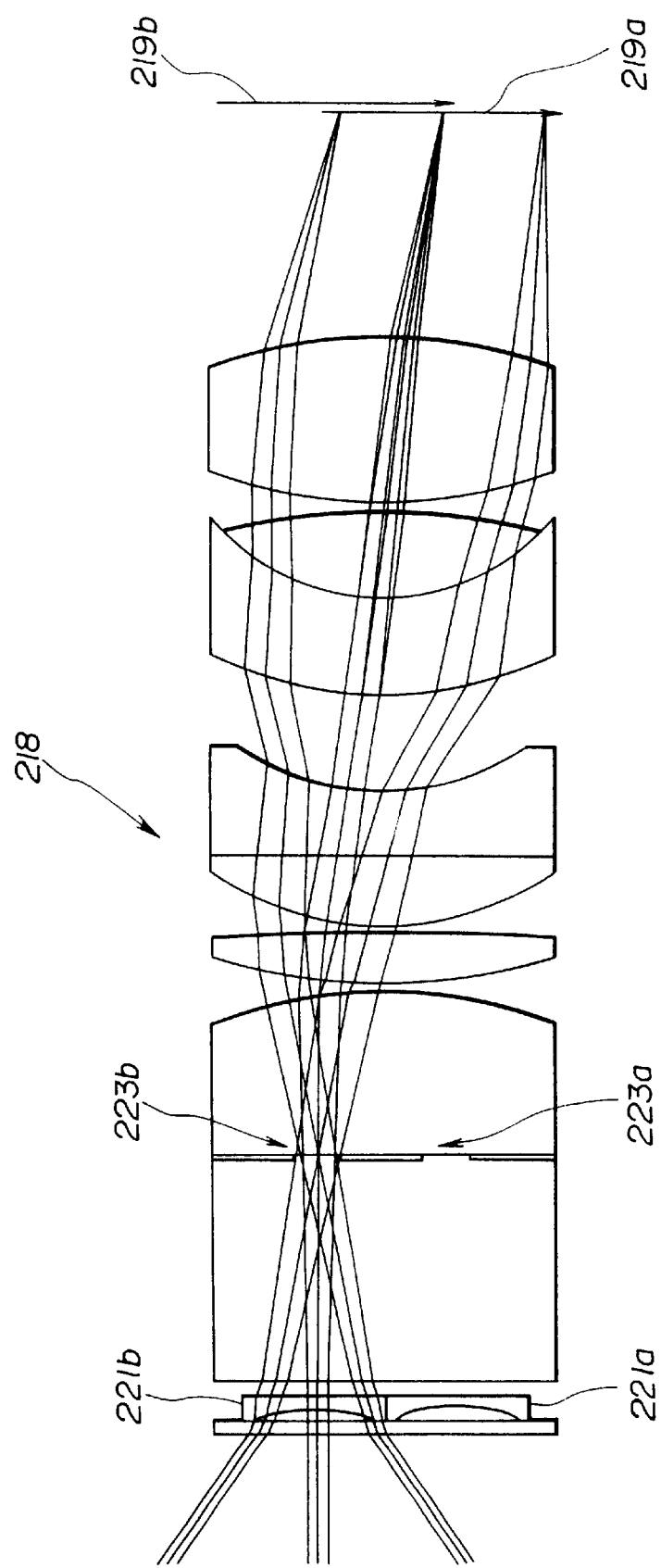
FIG. 44 is a formation view of the objective optical system in the twenty-fifth embodiment of the present invention.

In this embodiment, as shown in FIG. 44, the basic formation of the objective optical system 218 is the same as in the twenty-fourth embodiment. However, the image 219a formed of the light passing through the diaphragm opening 223b of the light from the object and the image 219b formed of the light passing through the diaphragm opening 223a are partially superimposed.

Figure 45:
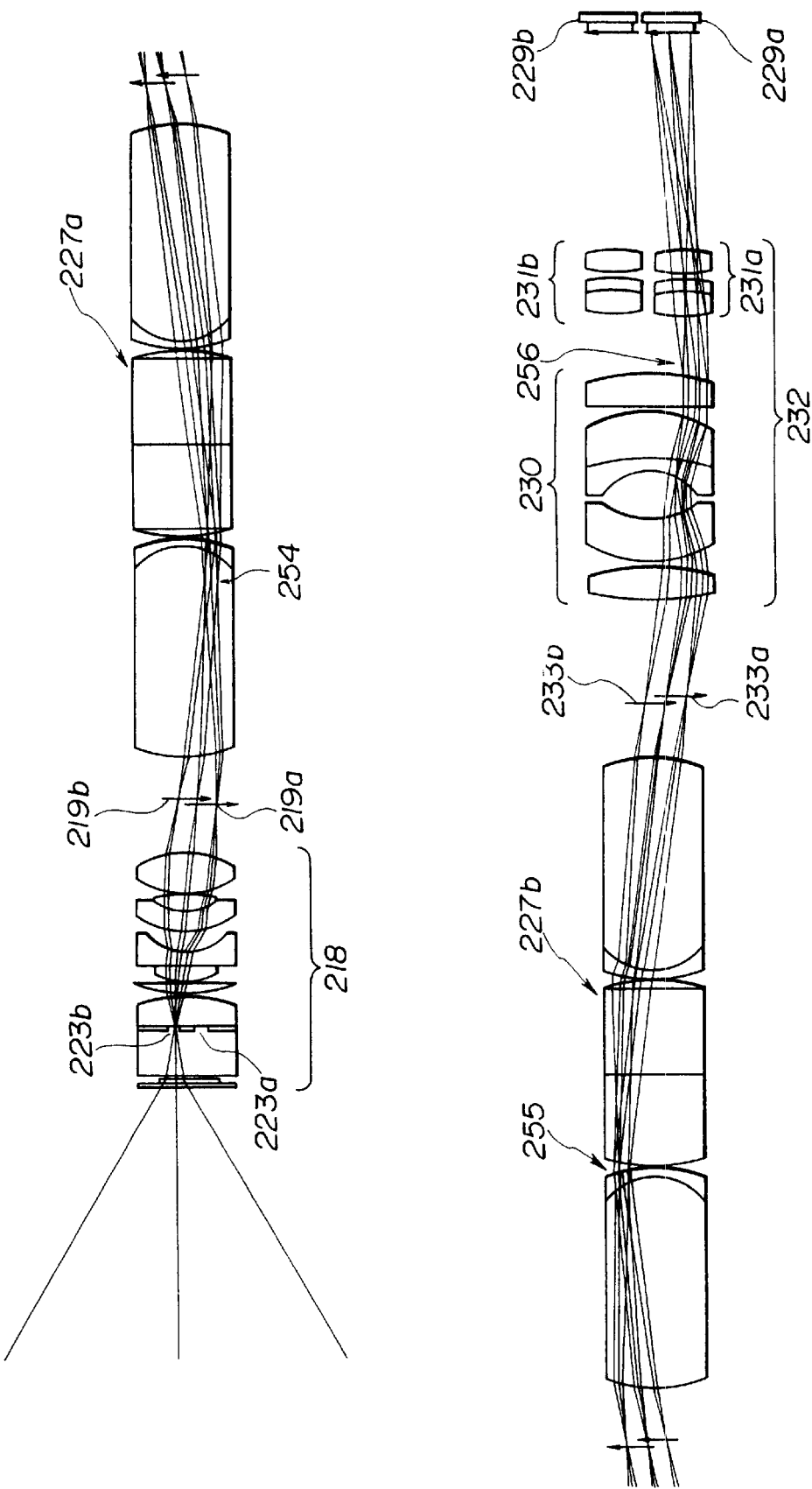
FIG. 45 is a formation view of the image transmitting optical system including the objective optical system in FIG. 44.

The images 219a and 219b formed by the objective optical system 218 are relayed by the relay lenses 227a and 227b as shown in FIG. 45. The images are then formed to be infinite by the pupil image forming lens 230 and are formed respectively on the CCD's 229a and 229b by a pair of left and right image forming lenses 231a and 231b. The images (pupils) of the diaphragm openings 223a and 223b are transmitted respectively to the positions 254, 255 and 256. As the two pupils have been separated in the position 256, the two partially superimposed images 233a and 233b relayed by the relay lenses 227a and 227b are formed separately by the image forming lenses 231a and 231b. The other formations, operations and effects are the same as in the twenty-fourth embodiment.

Here, the lens data of the objective optical system 218 and transmitting optical system 227 of this embodiment are shown in Table 12.

In the 25th embodiment, the left and right separate parts are present not only in the distal end section (the negative lenses 221a and 221b) but also within the image taking lens 232 (the image forming lenses 231a and 231b). Therefore, when the negative lenses are not adjusted but the image forming lenses are adjusted, the eccentricity error between the left and right images will be able to be adjusted.

However, in case the stereoendoscope 202 is made removable between the input section (until the transmitting optical system 227 or until the pupil image forming lens) and the output section (after the pupil image forming lens 230 or after the image forming lenses 231a and 231b), it will be necessary for the input section and output section to be independently adjusted. Therefore, even during such adjustment of the input section, the objective optical system of the present invention is very effective.

A plural visual field direction type endoscope after the 26th embodiment shall be explained in the following.

Figure 46:
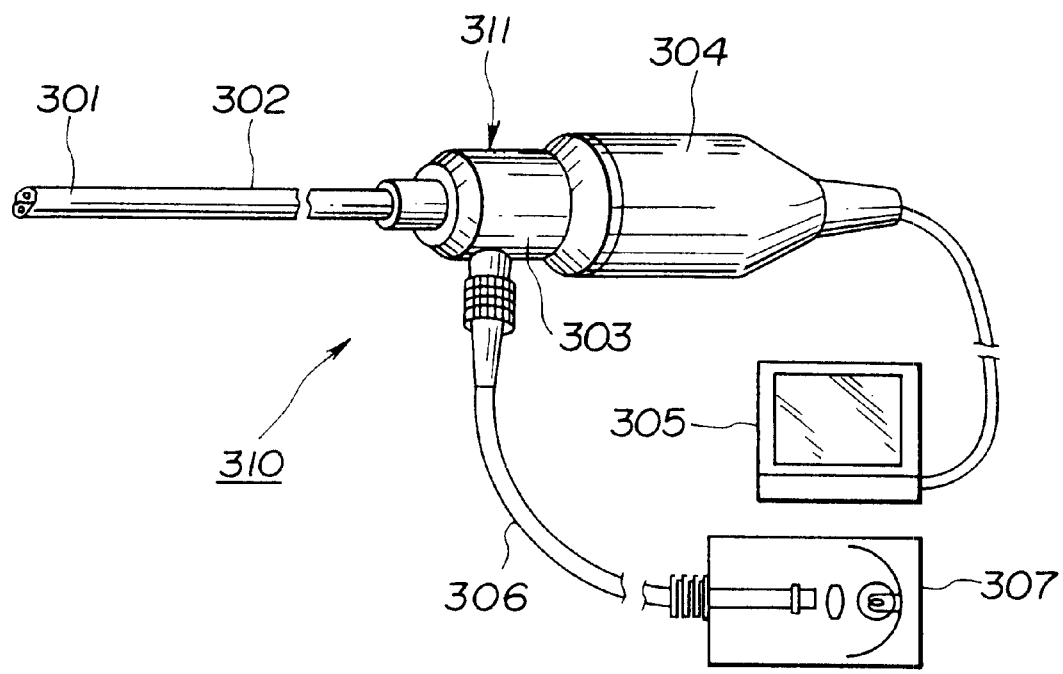

The endoscope apparatus 310 shown in FIG. 46 has an inserted section 302, an endoscope 311 in which the visual field direction is changeable in the 26th embodiment, a camera 304, monitor 305 and light source apparatus 307.

An objective optical system having a plurality of visual field directions and a light guide illuminating the respective visual field directions are incorporated in the distal end section 301 of the inserted section 302 of the endoscope 311. The inserted section 302 is provided with a relay lens system which is an image and pupil transmitting optical system following the objective optical system. An ocular optical system is arranged in the proximal section 303 of the endoscope 311. The camera 304 can be fitted in the rear of the ocular optical system. Here, the proximal section 303 of the endoscope 311 and the camera 304 are formed to be integral or removable. The object having had the image taken by the camera 304 is displayed to be observable by the observer as an endoscope picture image finally in the monitor 305. The illuminating light from the light source apparatus 307 passes through the light guide cable 306 and illuminates the respective visual field directions through the proximal section 303, inserted section 302 and distal end section 301.

The details of the optical system of the endoscope 311 shall be explained as follows:

On the optical systems of the endoscope of the 26th embodiment, a pupil division is utilized in the objective optical system and an ocular optical system is formed.

The pupil dividing system is fundamentally formed of an optical system having one optical axis but, in order to make a plural visual field direction type, a lens group corresponding to a plurality of visual field directions is arranged in front of the optical system. The plural visual field direction type optical system having adopted this pupil dividing system is formed of a front side lens group formed the same in a plurality of visual field directions and arranged in the respective plurality of visual field directions, a prism for forming images in the plurality of visual field directions in the rear step of the front side lens group corresponding to the plurality of visual field directions, a brightness diaphragm having a plurality of openings arranged near pupils, thereby forming a plurality of pupils and a rear side lens group forming one image of superimposed beams in the plurality of visual field directions in the order mentioned from the object side.

Figure 37B:
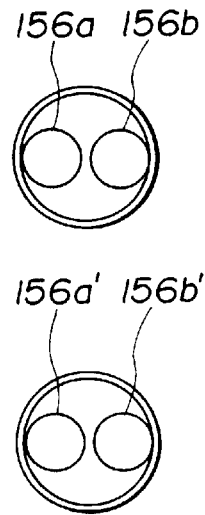
FIGS. 37A and 37B show the formation on the distal end side of the twenty-second embodiment of the present invention, where
Figure 37A:
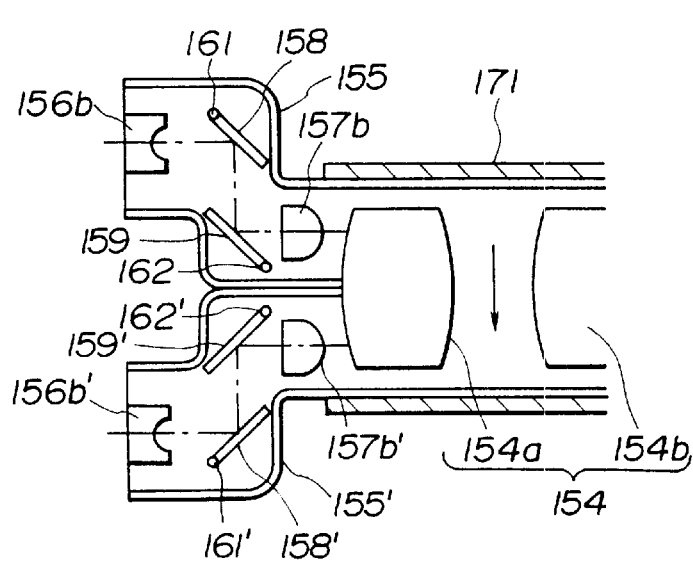

The inherent one beam of the optical system is divided near the pupil by the brightness diaphragm 321 having two openings and is shown in FIG. 37B. The beam passing through one opening of the brightness diaphragm 321 is seen straight-on as it is and the beam passing through the other opening of the brightness diaphragm 321 is perspectively seen in the visual field direction by the prism. Here, the two images in the visual field direction are formed to be superimposed on the image surface.

The formation of the optical system relating to this embodiment shall be explained concretely with reference to FIG. 47A. The optical system shown in FIG. 47A comprises an objective optical system 322, a set of relay lens system 323 as a transmitting optical system and an ocular optical system 324.

The objective optical system 322 has a front side lens group 329$a$ comprising two objective lenses 325 and 326 arranged in the positions nearest to the object and directed respectively in the straight seen direction and side seen direction, a first prism 327 making the beam from the two objective lenses 325 and 326 incident on different surfaces, a second prism 328 making the beam from the first prism 327 incident on the same surface and a brightness diaphragm 321 for dividing the pupil into a plurality of pupils in response to the visual field direction and has a rear side lens group 329$b$ for converging the beam from the pupils and forming the object image arranged in the rear of this front side lens group 329$a$. In the drawing, the one-point chain lines represent the optical axes of the respective visual field directions.

The image in the direction as seen straight-on in this optical system is formed as follows. The rays having passed through the straight-on seeing objective lens 326 pass through the surface 331 of the first prism 327 to the joint surface 332. The joint surface 332 on the first prism side 327 is black-painted so as to pass no others than the rays effective to prevent detrimental flares and is made a flare diaphragm. Because the first and second prisms 327 and 328 are made of the same glass material their refractive indices are equal and the rays pass through the surface 332 without being refracted. Then an image I1 having the lower side of the brightness diaphragm 321 as a pupil surface and having the optical axis of this rear side lens group 329$b$ as a center axis by the rear side lens group 329$b$ is formed.

On the other hand, the image in the perspectively seen direction is formed as follows. The rays passing through the perspectively seeing objective lens 325 pass through the surface 333 of the first prism 327 to the joint surface 332. At this time, the rays forming the image in the perspectively seen direction proceed straight through the joint surface without being refracted the same as the straight-on seen rays.

The joint surface 332 on the first prism side 327 is made a flare diaphragm passing no others than the rays effective to prevent detrimental flares. As the optical axis in the straight-on seen direction and the optical axis in the perspectively seen direction intersect with each other on the joint surface, the same flare diaphragm will effectively function on the rays in both directions. The straight proceeding rays in the perspectively seen direction are reflected by the mirror-processed surface 334 and go again to the surface 332 on the second prism 328 side.

The surface 332 on the second prism 328 side is mirror-processed in the range of not intercepting the straight-on seen rays and perspectively seen rays separated by the pupil division and in the range of covering the reflected perspectively seen rays reflected by the surface 334. Therefore, the rays in the perspectively seen direction reflected by the surface 334 without being perceived pass on the upper side of the brightness diaphragm 321 and are made the image I1 having the optical axis of the rear side lens group 329$b$ as a center axis by this rear side lens group 329, just as the straight-on seen rays and the image is formed.

The images I1 in the plurality of visual field directions made by the objective optical system 322 and the pupil P1 are transmitted in the ocular optical system direction by the relay lens system 323. In the drawing, the reference numeral P2 represents a plurality of pupils corresponding to the respective visual field directions transmitted by the relay lens. An image I2 is formed between the relay lens system 323 and ocular optical system 324. A plurality of pupils P3 corresponding to the respective visual field directions are obtained through the ocular optical system 324.

When the observer moves the position of his pupil to the position of the pupil transmitted in the visual field direction he wants to observe, he will be able to select the visual field direction.

In this embodiment, the objective optical system is originally designed as a coaxial optical system but not as an eccentric optical system and is formed to be bent with a prism for a pupil in a different visual field direction. That is to say, the optical axis of the objective lens 326 is on the extended line of the optical axis of the rear side lens group 329$b$ through the joint surface 332 and the optical axis of the objective lens 325 is on the extended line of the optical axis of the rear side lens group 329$b$ reflected on the joint surface 332 and further reflected on the reflecting surface 334. Therefore, between the optical system comprising two negative lenses and a prism and the optical system in the rear of it, even if the beam is not afocal, two images superposed before the relay system will be able to be formed.

In this embodiment, as the pupil division is utilized and originally one optical system is used, with a formation of few lenses, a high picture quality will be obtained, if the means for determining plural pupils is in a position conjugate with the pupil position of the objective optical system, it may be the position of the pupil P2 of the relay system 323 or any other part and, as the objective system and transmitting optical system have no visual field direction switching apparatus, the structure will be simple and the ease of assembly will be high.

An example of designing an actual objective optical system is shown in FIG. 48 and its numerical value data are mentioned in Table 13. By the way, in the formation shown in FIG. 48, the part shown as the rear side lens group 329$b$ in FIG. 47A is formed of a lens 329" jointed to a prism and three jointed lenses 329'.

In this embodiment, because the formed image is one, the following effects will be able to be obtained.

That is to say, as the objective optical system of the plural visual field direction type endoscope has a plurality of visual field directions, a plurality of pupils corresponding at 1 to 1 to the visual field directions and one image, the one image is a superimposition of images in a plurality of visual field directions, the optical axis of the plurality of visual field directions coincides with the optical axis of the transmitting system in the position of the image and, on the way of the transmission in the transmitting optical system after the image, one image and a plurality of pupils will be transmitted without being intercepted.

Therefore, in this embodiment, after the transmitting optical system, the visual field direction can be selected and no movable part is required in the objective optical system and transmitting optical system for selecting the visual field direction. Further, in this embodiment, because the objective optical system and the like have no visual field direction switching apparatus, the structure will be simple and the ease of assembly will be high. Also, because no polarization is used, there will be no deterioration of the image in the peripheral part by the rotation in the polarizing direction.

These effects will be the same even in case the pupil dividing means is in the transmitting optical system or image forming optical system The 27th embodiment shall be explained in the following with reference to FIGS. 49 to 54.

In the endoscope of this embodiment, an eccentric optical system is utilized for the objective optical system, an image forming optical system and solid state image taking device are used instead of the ocular optical system in the 26th embodiment and no optical visual field direction selecting means is provided.

FIG. 49A shows a formation of an optical system arranged within the endoscope of this embodiment.

The optical system of this embodiment comprises in the order mentioned from the distal end side an objective optical system 341, relay lens system 342, pupil image forming lens 343, such reflecting members 344a and 344b as a pupil separating optical member 344c and mirror and two solid state image taking devices 346a and 346b as an image taking means. By the way, though only one relay lens system is shown, it is natural that a plurality of relay lens systems may be used as required. The image forming lenses 345a and 345b form the image forming optical system.

In the objective optical system 341, a front optical system 347 comprising substantially afocal lens groups 347a and 347b independent of each other and having two straight-on seen and perspectively seen visual field directions and pupils P11 corresponding to these visual field directions is arranged in the front group and a rear side lens system 348 having a size capable of transmitting the beams from the plurality of pupils P11 to the image without being intercepted and forming one superimposed image of the beams in the plurality of visual field directions is arranged in the rear group.

The relay lens system 342 forms the images of the pupils P11 as pupils P12, forms the image I11 as an image I12 and transmits them to a pupil image forming lens 343. The pupil image forming lens 343 transmits the pupils transmitted from the relay lens system 342 to the side of a pupil separating optical member 344c having a plurality of reflecting surfaces. This pupil separating optical member 344c receives a plurality of pupils P13 and separates and delivers them in respectively different directions, that is, to the reflecting members 344a and 344b.

The reflecting members 344a and 344b reflect the beams passing through the separated respective pupils, that is, in the illustration, the two pupils corresponding to the optical system in the straight-on seen direction and the optical system in the perspectively seen direction respectively toward the lens systems 345a and 345b. The lens systems 345a and 345b form images corresponding to the respective pupils in the solid state image taking devices 346a and 346b.

In this formation, first the rays in the respective visual field directions pass through two substantially afocal lens groups 347a and 347b forming the front optical system 347, then the optical axes in the respective visual field directions are bent by the rear side lens system 348 and the image I11 is formed on the optical axis of the rear side lens system 348.

In this embodiment, substantially the same basic formation which realizes the perspective view made by the prisms 327 and 328 in the 26th embodiment is used. Here, the perspective view prism may be a 30° prism shown in the publications of Japanese Patent Applications Laid Open Nos. 140313/1985, 91333/1975 and 108013/1990 or a 70° prism or 110° prism shown in the publication of Japanese Patent Application Laid Open No. 87403/1984.

Figure 50:
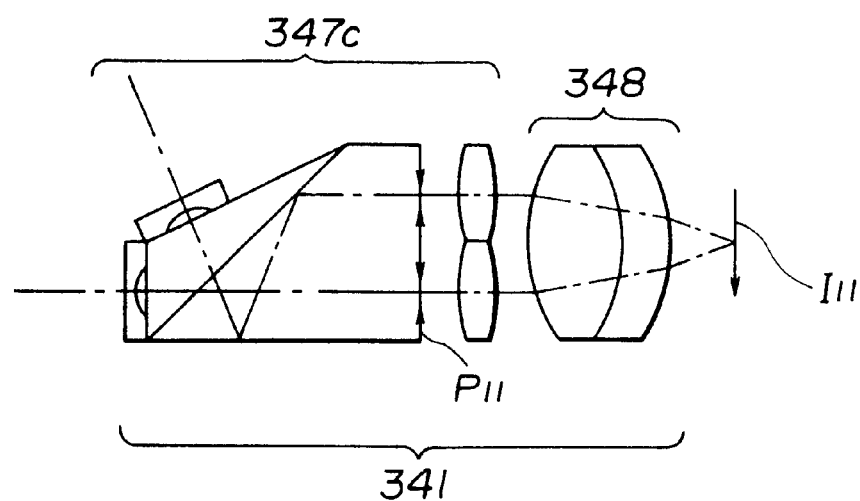
Figure 51:
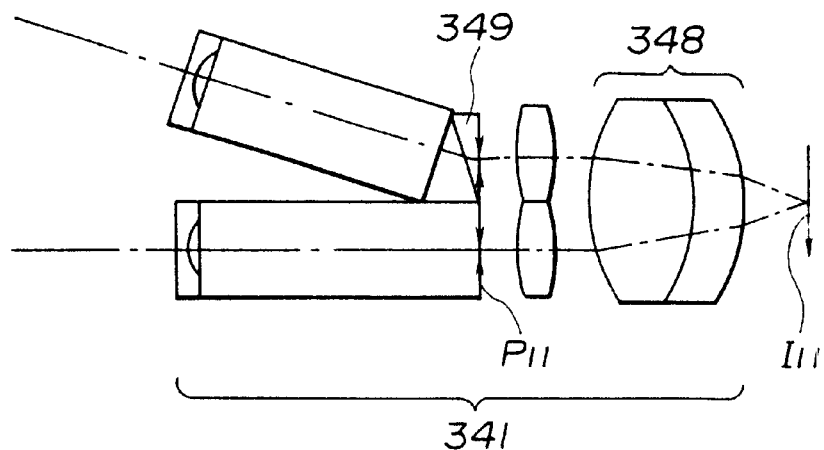

Also, the objective optical system 341 may be the front optical system 347c including the same prisms as the prisms 327 and 328 of the above mentioned embodiment as in FIG. 50, that is, may be a straight-on seeing and perspectively seeing optical system in common. Or the objective optical system 341 may realize a perspective view by utilizing refraction with a wedge prism 349 placed near the pupil P11 as in FIG. 51. In this formation, the lens group to be used respectively in the straight seen direction and the perspectively seen direction may be substantially the same lens group differing only in length, and the perspectively seeing lens group may be inclined to the straight-on seeing lens group and the wedge prism 349 may be arranged in the rear of it.

Figure 54:
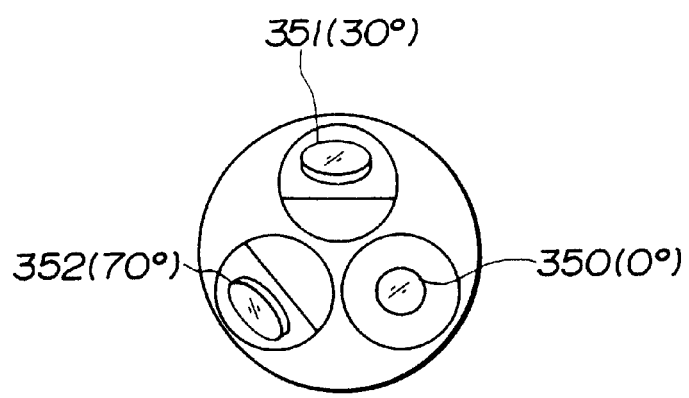

Otherwise, as shown in FIG. 54, the objective optical system 341 may have three or more visual field directions if in a range that the image and pupil are not intercepted by the relay lens system arranged in the rear. In the illustrated example are shown the most distal end side lenses 350, 351 and 352 forming respective lens groups respectively of 0 degrees (straight-on seen), 30 degrees (perspectively seen) and 70 degrees (perspectively seen).

As shown in FIG. 49A, the beam from the objective optical system 341 forms an image I12 in the rear of the relay lens system just as in the 26th embodiment by the relay lens system 342. Of the rays in the respective visual field directions forming the image I12 made in the rear of the relay lens system 342, the beams of the two pupils differing in the visual field direction are respectively separated by the pupil separating optical member 344c arranged in the rear of the pupil image forming lens 343.

This pupil separating optical member 344c is, for example, a prism arranged near the pupil P13 transmitted by the relay lens system 342 and formed as an image by the pupil image forming lens 343. The separated beams in the respective visual field directions are reflected respectively by the reflecting members 344a and 344b and are formed as images respectively on the image taking devices 346a and 346b through the lens systems 345a and 345b.

In this embodiment, by the pupil image forming lens 343 forming images of pupils, the optical axes in the respective visual field directions are made substantially parallel with the optical axis of the relay lens system 342 and the object point is formed as an image to infinity. By the way, the image may be formed so as not to be superimposed on one solid state image taking device.

According to this embodiment, images differing in the visual field direction can be independently taken by a plurality of solid state image taking devices and the number of visual fields and the visual field direction can be easily selected by the objective optical system. Without an optical visual field direction switching means, images in all the visual field directions are taken in. As in the illustrated example, in the formation using a plurality of solid state image taking devices, the outputs of the respective image taking devices are selected by switching the switch and the signals are processed as determined and can be displayed.

In the formation utilizing one solid state image taking device, the respective images different in the visual field direction may be selected by a signal processing means connected to the later step. The picture image in only one visual field direction can be displayed in a monitor.

That is to say, in this embodiment, without moving the optical system or without optically switching the visual field direction, the visual field direction can be changed. Also, depending on the way of processing the signal, a plurality of images in the visual field direction can be simultaneously displayed in one or a plurality of monitors.

Figure 52:
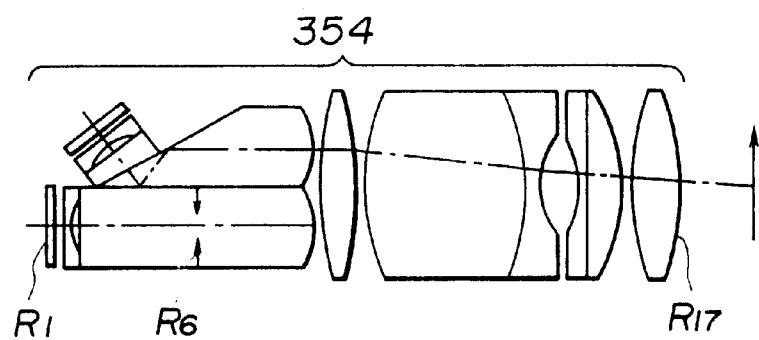
Figure 53:
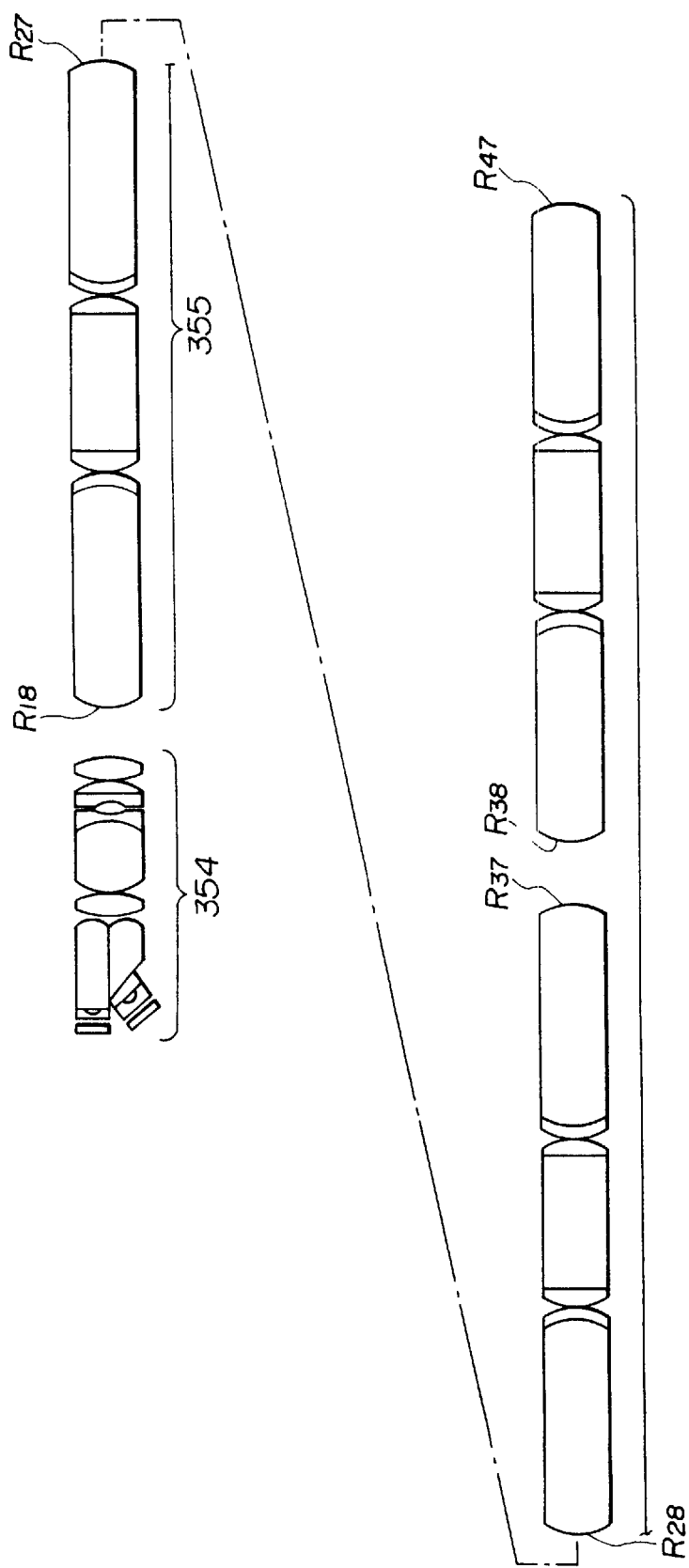

An example of designing an objective optical system is shown in FIG. 52. Also, an example of designing an objective optical system and relay lens system as combined is shown in FIG. 53. In the drawings, the reference numeral 354 represents an objective optical system and the reference numeral 355 represents a relay lens system. The lens data are mentioned in Table 14.

By the way, just as in the 26th embodiment, the diaphragm determining the pupil may be in the objective optical system, may be in the pupil position in the conjugate relay lens system or may be in the pupil position near the pupil dividing optical member.

In FIG. 49B is shown a modification of the 27th embodiment. In this modification, a pupil image P13 is formed of dispersed beams or converged beams by the pupil image forming lens 356 provided instead of the pupil image forming lens 343. Afocal beams are then formed by the lens 357 making the beams parallel and the beams are further formed as images by the image taking devices 346a and 346b through the image forming lenses 345a and 345b. In this modification, a reflexing prism as a pupil dividing optical member is unnecessary. The diaphragm may be arranged above the pupil position P13 in the drawing, in the relay lens system or in the pupil position in the objective optical system. The other same formations and operations as in the 27th embodiment shall bear the same reference numerals and shall not be explained here.

The 28th embodiment of the present invention shall be explained in the following with reference to FIGS. 55 to 58B.

In the formation of the 28th embodiment, an image forming optical system and a solid state image taking device are provided the same as in the 27th embodiment and further an optical visual field direction switching means is arranged.

The objective optical system in this embodiment may be the pupil dividing system in the 26th embodiment or may be formed of the substantially afocal plurality of optical systems and rear optical systems in the 27th embodiment. This embodiment is different from the above mentioned respective embodiments in the formation of the optical system and the like arranged in the rear of the relay lens system arranged in the rear of the objective optical system.

Figure 55:
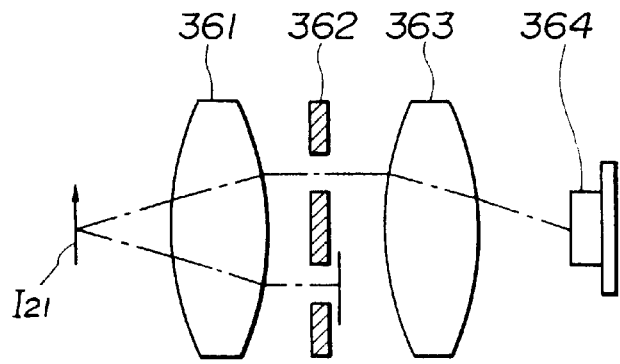

As shown in FIG. 55, the optical system in this embodiment comprises a lens system 361 for making the light which was once formed as an image by a relay lens system in the rear of the relay lens system (not illustrated) and then became dispersed beams in the respective visual field directions parallel with the optical axis of the relay lens, a pupil switching apparatus 362 as a selecting means switching the beams in the respective visual field directions made parallel in response to the respective pupils and arranged near the pupils to be formed as images through the lens system 361 and an image forming lens system 363 forming images of the rays selected by the pupil switching device 362 on the solid-state image taking device 364.

The rays in the respective visual field directions forming the image I21 formed in the rear of the relay lens system are made parallel with the optical axis of the relay lens system by the lens system 361. By the switching apparatus 362 near the pupil position, the rays passing through the other images than in the visual field direction the observer wants to observe are intercepted. The intercepting means as a selecting means may be a mechanically moved shielding plate or may be a liquid crystal shutter switch to be on/off.

Figure 56A:
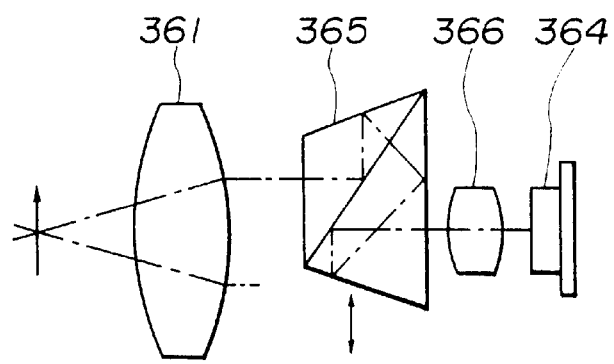
FIGS. 56A and 56B are formation views of a plural visual field direction type endoscope in which the visual field direction can be switched by an image rotator.
Figure 56B:
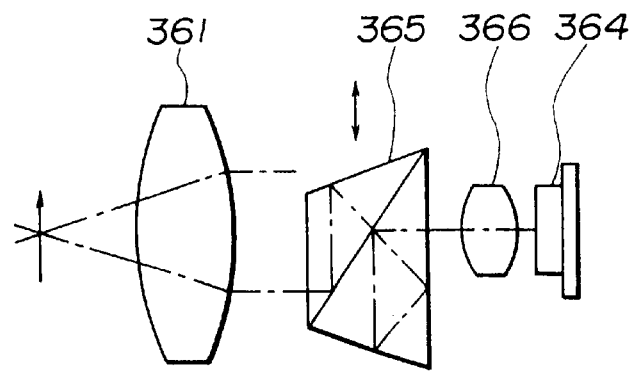

The selecting means may be such image rotator 365 as in FIGS. 56A and 56B to be moved to switch the visual field direction. The reference numeral 366 represents an image forming lens system forming an image of the rays obtained by the image rotator 365 on the solid state image taking device. By the way, FIGS. 56A and 56B show that the visual field direction is switched by moving the image rotator 365.

Figure 57:
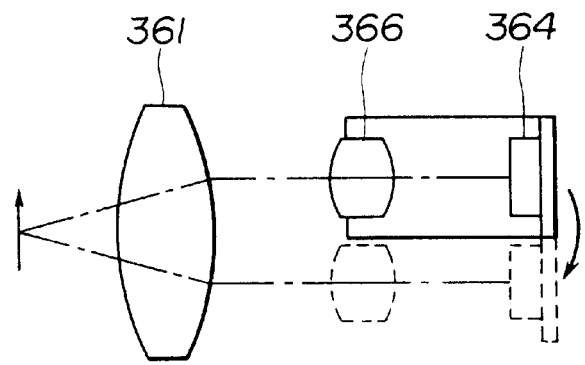
Figure 58:
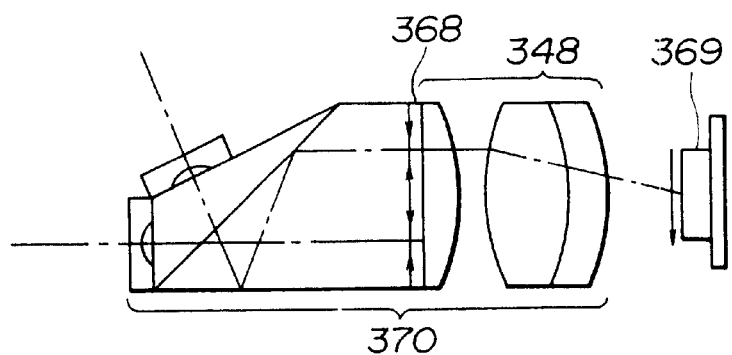
Figure 58:
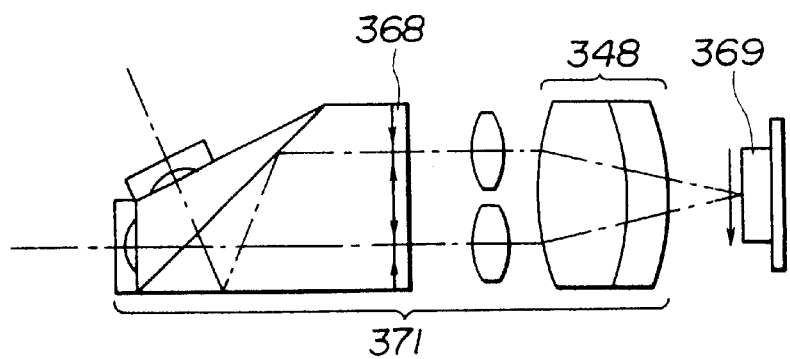

Also, as shown in FIG. 57, the selecting means may be moved to the position of the visual field direction desired to be observed integrally with the image forming lens system 365 and solid state image taking device 364 to switch the visual field direction. Only the image in the selected visual field direction is formed on the solid state image forming device 364.

The effect of this embodiment is that the visual field direction can be changed in a small space.

By the way, in case the pupil and image made by the objective optical system are transmitted by the relay lens system and the pupil dividing means is arranged after the relay lens system, the brightness diaphragm 321 can be omitted.

The formations of the 27th and 28th embodiments have an image taking means and may be applied to an outside fitted camera connectable to the ocular optical system of the 26th embodiment. In this formation, the lens system 343 or 361 is replaced with the ocular optical system 324.

The optical system after the transmitting optical system combining utilizing the pupil division in the objective optical system and utilizing the eccentric optical system can be selected either to have the ocular optical system and optical visual field direction switching means or to have none.

In the case of either utilizing the pupil division in the objective optical system of the present invention or utilizing the eccentric optical system, when the means of intercepting the rays other than in the required visual field direction are provided near the pupils in the respective visual field directions, even if the transmitting optical system is replaced with the solid state image taking device or image guide, the visual field direction variable endoscope will be able to be realized.

In the formation shown in FIG. 58A, a pupil switching apparatus 368 is provided near the pupil formed in the light path of the objective optical system 370 consisting of the front side lens group which is the same as the front side lens group 329a of the 26th embodiment and the rear side lens system 348 and a solid state image taking device 369 is arranged. The pupil switching apparatus 368 may be a liquid crystal shutter or the like.

Also, in the formation shown in FIG. 58B, an eccentric optical system 371 including the same optical system as the front optical system 347c shown in FIG. 50 is utilized.

FIG. 59A is a formation view of an optical system in the plural visual field direction type endoscope in the 29th embodiment. FIG. 59B is a formation view of an objective optical system made partially in common.

The objective optical system in the 29th embodiment is formed of a plurality of lens groups provided for respective visual fields instead of the objective optical system 322 so that a plurality of images may be formed by these lens groups. The other formations and operations which are the same as in the 26th embodiment shall bear the same reference numerals and shall not be explained here.

The objective optical system 373 shown in FIG. 59A is formed of a plurality of (two in the illustrated example) independent lens groups. The relay lens system 323 and ocular optical system 324 are arranged in the rear of the objective optical system 373. By the way, the relay lens system 323 and ocular optical system may be replaced with an image forming optical system and solid state image taking device.

The objective optical system 373 may be formed of an independent optical system as in FIG. 59A and may have a part, that is, the prism on the distal end side made in common as in the objective optical system 373' shown in FIG. 59B.

The plurality of images I31 and I32 formed by the objective optical system are transmitted rearward by the relay lens system 323 as a transmitting optical system. In the formation having the ocular optical system 324, as in FIG. 59A, the observer can simultaneously see the respective visual field directions with the eye placed in the pupil position 374.

On the other hand, in the formation of the image forming optical system and solid state image taking device, the plurality of images made in the rear of the relay lens system 323 are formed on one solid state image taking device by the image forming lens. The effect by this formation can be technically comparatively easily realized by any optical system after the objective optical system and transmitting optical system.

By the way, in this embodiment, images may be formed on a plurality of solid state image taking devices with the image forming magnification made large and the solid state image taking devices placed in the positions corresponding to the plurality of images.

The 30th embodiment shall be explained with reference to FIG. 60A. As shown in FIG. 60A, in the optical system of this embodiment, an image is formed on the solid state image taking device 370 through the lens system 343 which is arranged in the rear of the relay lens system 342 and whereby the light once formed as an image by the relay lens system 342 and then made dispersed beams in the respective visual field directions is made parallel with the optical axes of the relay lens system 342 and optical systems arranged along two optical axes in the rear of this lens system 343.

Multiple relay systems by the lens systems 371 and 372 are arranged along one optical axis of the two optical axes and an image is formed on the solid state image taking device 370 by the lens system 372.

Also, multiple relay systems are arranged on the other optical axis. That is to say, the prism 373 for bending the optical axis is arranged near the pupil formed through the lens system 374 and on the rear side of this prism 373 are arranged the lens system 374, prism 375, lens system 376, prism 377, lens system 378 and mirror 379. The beam is reflected by this mirror 379 arranged at the point P of intersection of this optical system and the other optical axis and forms an image on the solid state image taking device 370 through the lens system 372.

This mirror 379 is rotatable as illustrated. The visual field direction can be selected by switching to either of the state A indicated by the solid line and the state B indicated by the dotted line. The other formations are the same components as are explained in FIG. 49A.

In the inserted section of the rigid endoscope to which this embodiment is applied, the distance between the two optical axes cannot help being so small as to be several millimeters due to the restriction of the outside diameter. As the image is formed on one solid state image taking device 370 after the lens system 343, in case one optical system is used the same as in the relay lens system 342, the beam will diagonally project into the solid state image taking device 370 and a color shading will be generated. In order to prevent this phenomenon, in this embodiment, one of the two optical axes is bent by the prisms 373, 375 and 377 on the rear side of the lens system 343 as in FIG. 60A so that the beams having passed respectively through the two optical axes may project vertically onto the image taking surface of the solid state image taking device 370 and the generation of the color shading may be controlled.

FIG. 60B shows a formation of a modification of FIG. 60A. The optical system in FIG. 60A is formed of expanded lens systems 374', 376' and 378' expanding respectively the lens systems 374, 376 and 378 so that the image may be observed in a larger picture surface size with one of the optical systems having two visual field directions. When the formation is separated into the inserted section 380 and the camera adapter section 381 rotatably fitted to this inserted section 380 and the camera adapter section 381 is rotatably formed, the picture sizes in the respective visual field directions will be able to be selectively made large.

FIG. 61A shows the 31st embodiment. In this embodiment, objective optical systems 391 and 391' to be a pair on the respective optical axes separated by a distance D are provided on the distal end side of the inserted section 390 and the respective images by the optical objective systems 391 and 391' are transmitted to the rear side respectively by the relay optical systems 392 and 392'.

The image transmitted by the relay optical system 392 is formed on the solid state image taking device 370 by the multiple relay optical systems comprising the lens systems 371 and 372 the same as in FIG. 60A.

Also, the image transmitted by the relay optical system 392' is formed on the solid state image taking device 370 through the same relay systems as in FIG. 60A, that is, the multiple relay systems by the prism 373, lens system 374, prism 375, lens system 376, prism 377, lens system 378, mirror 379 and lens system 372.

The same as in the embodiment in FIG. 60A, as a means of switching the two optical systems, a mirror 379 is provided at the point P at which the two optical axes intersect with each other. The visual field direction can be selected by this mirror 379.

In the modification shown in FIG. 61B, the lens systems 374, 376 and 378 forming the relay systems in FIG. 61A are formed respectively of the expanded lens systems 374', 376' and 378' so that one optical system, that is, the objective optical system 391' and relay optical system 392' of the two optical systems arranged within the inserted section 390 may be made thinner, the outside diameter of the inserted section may be made smaller and the insertability may be improved.

Also, when the formation is separated into the inserted section 390 and the camera adapter section 393 rotatably fitted to the rear end of this inserted section and the camera adapter section 393 is rotatably formed, the picture size will be able to be selectively varied.

By the way, the present invention is not limited to these embodiments and modifications and any embodiment or modification formed by combining parts of them belongs to the present invention.

TABLE 1

| Lens data of the first embodiment | | | | | | | |
|---|---|---|---|---|---|---|---|
| r1 = | ∞ | d1 = | 0.400 | n1 = 1.7682 | v1 = 71.8 |
| r2 = | ∞ | d2 = | 0.300 | | |
| r3 = | 2.4658 | d3 = | 0.563 | n2 = 1.883 | v2 = 40.8 |
| r4 = | 0.7855 | d4 = | 0.453 | | |
| r5 = | ∞ | d5 = | 0.400 | n3 = 1.8061 | v3 = 40.9 |
| r6 = | ∞ (pupil) | d6 = | 3.340 | n4 = 1.8061 | v4 = 40.9 |
| r7 = | −2.7844 | d7 = | 0.300 | | |
| r8 = | −4.5712 | d8 = | 0.400 | n5 = 1.62004 | v5 = 36.3 |

TABLE 1-continued

Lens data of the first embodiment

| | | | | | | | |
|---|---|---|---|---|---|---|---|
| r9 = | 13.1850 | d9 = | 0.730 | n6 = | 1.788 | ν6 = | 47.4 |
| r10 = | −3.7741 | d10 = | 0.300 | | | | |
| r11 = | 6.2003 | d11 = | 1.949 | n7 = | 1.60311 | ν7 = | 60.7 |
| r12 = | −1.6595 | d12 = | 0.409 | n8 = | 1.84666 | ν8 = | 23.8 |
| r13 = | −2.4812 | d13 = | 0.306 | | | | |
| r14 = | −2.3688 | d14 = | 0.400 | n9 = | 1.78472 | ν9 = | 25.7 |
| r15 = | −82.9824 | d15 = | 0.400 | n10 = | 1.6968 | ν10 = | 55.5 |
| r16 = | −7.6931 | d16 = | 7.500 | | | | |
| r17 = | 17.7721 | d17 = | 38.862 | n11 = | 1.51633 | ν11 = | 64.1 |
| r18 = | −8.3001 | d18 = | 6.881 | n12 = | 1.85026 | ν12 = | 32.3 |
| r19 = | −24.9616 | d19 = | 0.941 | | | | |
| r20 = | 36.2005 | d20 = | 1.000 | n13 = | 1.8061 | ν13 = | 40.9 |
| r21 = | ∞ | d21 = | 10.265 | n14 = | 1.51633 | ν14 = | 64.1 |
| r22 = | ∞ | d22 = | 1.000 | n15 = | 1.8061 | ν15 = | 40.9 |
| r23 = | −36.2005 | d23 = | 0.914 | | | | |
| r24 = | 24.9616 | d24 = | 6.881 | n16 = | 1.85026 | ν16 = | 32.3 |
| r25 = | 8.3001 | d25 = | 38.862 | n17 = | 1.51633 | ν17 = | 64.1 |
| r26 = | −17.7721 | d26 = | 10.000 | | | | |
| r27 = | 17.7721 | d27 = | 38.862 | n18 = | 1.51633 | ν18 = | 64.1 |
| r28 = | −8.3001 | d28 = | 6.881 | n19 = | 1.85026 | ν19 = | 32.3 |
| r29 = | −24.9616 | d29 = | 0.914 | | | | |
| r30 = | 36.2005 | d30 = | 1.000 | n20 = | 1.8061 | ν20 = | 40.9 |
| r31 = | ∞ | d31 = | 10.265 | n21 = | 1.51633 | ν21 = | 64.1 |
| r32 = | ∞ | d32 = | 1.000 | n22 = | 1.8061 | ν22 = | 40.9 |
| r33 = | −36.2005 | d33 = | 0.914 | | | | |
| r34 = | 24.9616 | d34 = | 6.881 | n23 = | 1.85026 | ν23 = | 32.3 |
| r35 = | 8.3001 | d35 = | 38.862 | n24 = | 1.51633 | ν24 = | 64.1 |
| r36 = | −17.7721 | d36 = | 10.000 | | | | |
| r37 = | 17.7721 | d37 = | 38.862 | n25 = | 1.51633 | ν25 = | 64.1 |
| r38 = | −8.3001 | d38 = | 6.881 | n26 = | 1.85026 | ν26 = | 32.3 |
| r39 = | −24.9616 | d39 = | 0.914 | | | | |
| r40 = | 36.2005 | d40 = | 1.000 | n27 = | 1.8061 | ν27 = | 40.9 |
| r41 = | ∞ | d41 = | 10.265 | n28 = | 1.51633 | ν28 = | 64.1 |
| r42 = | ∞ | d42 = | 1.000 | n29 = | 1.8061 | ν29 = | 40.9 |
| r43 = | −36.2005 | d43 = | 0.914 | | | | |
| r44 = | 24.9616 | d44 = | 6.881 | n30 = | 1.85026 | ν30 = | 32.3 |
| r45 = | 8.3001 | d45 = | 38.862 | n31 = | 1.51633 | ν31 = | 64.1 |
| r46 = | −17.7721 | d46 = | 5.000 | | | | |
| r47 = ∞ (image position) | | | | | | | |

TABLE 2

Lens data of the third embodiment

| | | | | | | | |
|---|---|---|---|---|---|---|---|
| r1 = | ∞ | d1 = | 0.400 | n1 = | 1.7682 | ν1 = | 71.8 |
| r2 = | ∞ | d2 = | 0.300 | | | | |
| r3 = | 3.8772 | d3 = | 1.527 | n2 = | 1.883 | ν2 = | 40.8 |
| r4 = | 0.7999 | d4 = | 0.449 | | | | |
| r5 = | ∞ | d5 = | 0.400 | n3 = | 1.8061 | ν3 = | 40.9 |
| r6 = | ∞ (pupil) | d6 = | 2.774 | n4 = | 1.8061 | ν4 = | 40.9 |
| r7 = | −2.6393 | d7 = | 0.300 | | | | |
| r8 = | −4.4440 | d8 = | 0.400 | n5 = | 1.62004 | ν5 = | 36.3 |
| r9 = | 13.0243 | d9 = | 0.643 | n6 = | 1.788 | ν6 = | 47.4 |
| r10 = | −3.4953 | d10 = | 0.300 | | | | |
| r11 = | 6.6459 | d11 = | 1.858 | n7 = | 1.60311 | ν7 = | 60.7 |
| r12 = | −1.6646 | d12 = | 0.416 | n8 = | 1.84666 | ν8 = | 23.8 |
| r13 = | −2.4857 | d13 = | 0.300 | | | | |
| r14 = | −2.4171 | d14 = | 0.400 | n9 = | 1.78472 | ν9 = | 25.7 |
| r15 = | −5.1842 | d15 = | 0.400 | n10 = | 1.6968 | ν10 = | 55.5 |
| r16 = | −5.8028 | d16 = | 7.500 | | | | |
| r17 = | 17.0269 | d17 = | 39.876 | n11 = | 1.51633 | ν11 = | 64.1 |
| r18 = | −9.1442 | d18 = | 6.480 | n12 = | 1.85026 | ν12 = | 32.3 |
| r19 = | −25.2664 | d19 = | 0.300 | | | | |
| r20 = | 38.6357 | d20 = | 1.000 | n13 = | 1.8061 | ν13 = | 40.9 |
| r21 = | ∞ | d21 = | 10.000 | n14 = | 1.51633 | ν14 = | 64.1 |
| r22 = | ∞ | d22 = | 1.000 | n15 = | 1.8061 | ν15 = | 40.9 |
| r23 = | −38.6357 | d23 = | 0.300 | | | | |
| r24 = | 25.2664 | d24 = | 6.480 | n16 = | 1.85026 | ν16 = | 32.3 |
| r25 = | 9.1442 | d25 = | 39.876 | n17 = | 1.51633 | ν17 = | 64.1 |
| r26 = | −17.0269 | d26 = | 10.000 | | | | |
| r27 = | 17.0269 | d27 = | 39.876 | n18 = | 1.51633 | ν18 = | 64.1 |
| r28 = | −9.1442 | d28 = | 6.480 | n19 = | 1.85026 | ν19 = | 32.3 |
| r29 = | −25.2664 | d29 = | 0.300 | | | | |
| r30 = | 38.6357 | d30 = | 1.000 | n20 = | 1.8061 | ν20 = | 40.9 |

TABLE 2-continued

Lens data of the third embodiment

| | | | | | | | |
|---|---|---|---|---|---|---|---|
| r31 = | ∞ | d31 = | 10.000 | n21 = | 1.51633 | ν21 = | 64.1 |
| r32 = | ∞ | d32 = | 1.000 | n22 = | 1.8061 | ν22 = | 40.9 |
| r33 = | −38.6357 | d33 = | 0.300 | | | | |
| r34 = | 25.2664 | d34 = | 6.480 | n23 = | 1.85026 | ν23 = | 32.3 |
| r35 = | 9.1442 | d35 = | 39.876 | n24 = | 1.51633 | ν24 = | 64.1 |
| r36 = | −17.0269 | d36 = | 10.000 | | | | |
| r37 = | 17.0269 | d37 = | 39.876 | n25 = | 1.51633 | ν25 = | 64.1 |
| r38 = | −9.1442 | d38 = | 6.480 | n26 = | 1.85026 | ν26 = | 32.3 |
| r39 = | −25.2664 | d39 = | 0.300 | | | | |
| r40 = | 38.6357 | d40 = | 1.000 | n27 = | 1.8061 | ν27 = | 40.9 |
| r41 = | ∞ | d41 = | 10.000 | n28 = | 1.51633 | ν28 = | 64.1 |
| r42 = | ∞ | d42 = | 1.000 | n29 = | 1.8061 | ν29 = | 40.9 |
| r43 = | −38.6357 | d43 = | 0.300 | | | | |
| r44 = | 25.2664 | d44 = | 6.480 | n30 = | 1.85026 | ν30 = | 32.3 |
| r45 = | 9.1442 | d45 = | 39.876 | n31 = | 1.51633 | ν31 = | 64.1 |
| r46 = | −17.0269 | d46 = | 5.001 | | | | |
| r47 = ∞ (image position) | | | | | | | |

TABLE 3

Lens data of the forth embodiment

| | | | | | | | |
|---|---|---|---|---|---|---|---|
| r1 = | ∞ | d1 = | 0.400 | n1 = | 1.7682 | ν1 = | 71.8 |
| r2 = | ∞ | d2 = | 0.300 | | | | |
| r3 = | 2.6660 | d3 = | 1.000 | n2 = | 1.883 | ν2 = | 40.8 |
| r4 = | 0.6568 | d4 = | 0.465 | | | | |
| r5 = | ∞ | d5 = | 0.400 | n3 = | 1.883 | ν3 = | 40.8 |
| r6 = | ∞ (pupil) | d6 = | 2.938 | n4 = | 1.883 | ν4 = | 40.8 |
| r7 = | −2.9259 | d7 = | 0.300 | | | | |
| r8 = | −10.3818 | d8 = | 0.400 | n5 = | 1.62004 | ν5 = | 36.3 |
| r9 = | 15.1216 | d9 = | 0.562 | n6 = | 1.788 | ν6 = | 47.4 |
| r10 = | −4.9186 | d10 = | 0.300 | | | | |
| r11 = | 6.1372 | d11 = | 1.797 | n7 = | 1.60311 | ν7 = | 63.4 |
| r12 = | −1.8144 | d12 = | 1.075 | n8 = | 1.84666 | ν8 = | 23.8 |
| r13 = | −2.6860 | d13 = | 0.300 | | | | |
| r14 = | −2.2723 | d14 = | 0.615 | n9 = | 1.78472 | ν9 = | 25.7 |
| r15 = | −14.0716 | d15 = | 0.437 | n10 = | 1.6968 | ν10 = | 55.5 |
| r16 = | −4.9749 | d16 = | 7.500 | | | | |
| r17 = | 18.4320 | d17 = | 37.230 | n11 = | 1.51633 | ν11 = | 64.1 |
| r18 = | −8.3411 | d18 = | 6.671 | n12 = | 1.85026 | ν12 = | 32.3 |
| r19 = | −24.0584 | d19 = | 0.300 | | | | |
| r20 = | 36.1875 | d20 = | 1.000 | n13 = | 1.8061 | ν13 = | 40.9 |
| r21 = | ∞ | d21 = | 10.000 | n14 = | 1.51633 | ν14 = | 64.1 |
| r22 = | ∞ | d22 = | 1.000 | n15 = | 1.8061 | ν15 = | 40.9 |
| r23 = | −36.1875 | d23 = | 0.300 | | | | |
| r24 = | 24.0584 | d24 = | 6.671 | n16 = | 1.85026 | ν16 = | 32.3 |
| r25 = | 8.3411 | d25 = | 37.230 | n17 = | 1.51633 | ν17 = | 64.1 |
| r26 = | −18.4320 | d26 = | 10.000 | | | | |
| r27 = | 18.4320 | d27 = | 37.230 | n18 = | 1.51633 | ν18 = | 64.1 |
| r28 = | −8.3411 | d28 = | 6.671 | n19 = | 1.85026 | ν19 = | 32.3 |
| r29 = | −24.0584 | d29 = | 0.300 | | | | |
| r30 = | 36.1875 | d30 = | 1.000 | n20 = | 1.8061 | ν20 = | 40.9 |
| r31 = | ∞ | d31 = | 10.000 | n21 = | 1.51633 | ν21 = | 64.1 |
| r32 = | ∞ | d32 = | 1.000 | n22 = | 1.8061 | ν22 = | 40.9 |
| r33 = | −36.1875 | d33 = | 0.300 | | | | |
| r34 = | 24.0584 | d34 = | 6.671 | n23 = | 1.85026 | ν23 = | 32.3 |
| r35 = | 8.3411 | d35 = | 37.230 | n24 = | 1.51633 | ν24 = | 64.1 |
| r36 = | −18.4320 | d36 = | 10.000 | | | | |
| r37 = | 18.4320 | d37 = | 37.230 | n25 = | 1.51633 | ν25 = | 64.1 |
| r38 = | −8.3411 | d38 = | 6.671 | n26 = | 1.85026 | ν26 = | 32.3 |
| r39 = | −24.0584 | d39 = | 0.300 | | | | |
| r40 = | 36.1875 | d40 = | 1.000 | n27 = | 1.8061 | ν27 = | 40.9 |
| r41 = | ∞ | d41 = | 10.000 | n28 = | 1.51633 | ν28 = | 64.1 |
| r42 = | ∞ | d42 = | 1.000 | n29 = | 1.8061 | ν29 = | 40.9 |
| r43 = | −36.1875 | d43 = | 0.300 | | | | |
| r44 = | 24.0584 | d44 = | 6.671 | n30 = | 1.85026 | ν30 = | 32.3 |
| r45 = | 8.3411 | d45 = | 37.230 | n31 = | 1.51633 | ν31 = | 64.1 |
| r46 = | −18.4320 | d46 = | 5.000 | | | | |
| r47 = | ∞ | d47 = | 6.000 (reflection plane) | | | | |
| r48 = | ∞ | d47 = | 9.000 (reflection plane) | | | | |
| r49 = | −15.7631 | d49 = | 4.949 | n32 = | 1.816 | ν32 = | 46.6 |
| r50 = | −8.9021 | d50 = | 2.525 | | | | |
| r51 = | 9.9691 | d51 = | 4.480 | n33 = | 1.72916 | ν33 = | 54.7 |
| r52 = | −16.7003 | d52 = | 2.578 | n34 = | 1.7552 | ν34 = | 27.5 |

TABLE 3-continued

Lens data of the forth embodiment

| | | | | | | | |
|---|---|---|---|---|---|---|---|
| r53 = | 4.2972 | d53 = | 3.722 | | | | |
| r54 = | 52.6411 | d54 = | 1.000 | n35 = 1.5927 | v35 = 35.3 |
| r55 = | 117.6536 | d55 = | 7.067 | n36 = 1.618 | v36 = 63.4 |
| r56 = | −77.9950 | d56 = | 1.037 | | |
| r57 = | 8.7799 | d57 = | 7.000 | n37 = 1.72916 | v37 = 54.7 |
| r58 = | 13.9542 | d58 = | 49.995 | | |
| r59 = ∞ (image position) | | | | | |

TABLE 4

Lens data of the fifth embodiment

| | | | | | |
|---|---|---|---|---|---|
| r1 = | ∞ | d1 = | 0.400 | n1 = 1.7682 | v1 = 71.8 |
| r2 = | ∞ | d2 = | 0.300 | | |
| r3 = | 2.8586 | d3 = | 1.000 | n2 = 1.883 | v2 = 40.8 |
| r4 = | 0.7279 | d4 = | 0.466 | | |
| r5 = | ∞ | d5 = | 0.400 | n3 = 1.883 | v3 = 40.8 |
| r6 = | ∞ (pupil) | d6 = | 2.216 | n4 = 1.883 | v4 = 40.8 |
| r7 = | −2.9043 | d7 = | 0.300 | | |
| r8 = | −5.6042 | d8 = | 0.400 | n5 = 1.62004 | v5 = 36.3 |
| r9 = | 5.6154 | d9 = | 0.888 | n6 = 1.788 | v6 = 47.4 |
| r10 = | −3.6606 | d10 = | 0.300 | | |
| r11 = | 7.1344 | d11 = | 1.764 | n7 = 1.618 | v7 = 63.4 |
| r12 = | −1.7751 | d12 = | 0.597 | n8 = 1.84666 | v8 = 23.8 |
| r13 = | −2.5646 | d13 = | 0.302 | | |
| r14 = | −2.1629 | d14 = | 0.400 | n9 = 1.78472 | v9 = 25.7 |
| r15 = | −4.7832 | d15 = | 0.400 | n10 = 1.6968 | v10 = 55.5 |
| r16 = | −3.9862 | d16 = | 7.500 | | |
| r17 = | 18.1763 | d17 = | 37.730 | n11 = 1.51633 | v11 = 64.1 |
| r18 = | −8.5520 | d18 = | 6.670 | n12 = 1.85026 | v12 = 32.2 |
| r19 = | −23.4978 | d19 = | 0.300 | | |
| r20 = | 39.1240 | d20 = | 1.000 | n13 = 1.8061 | v13 = 40.9 |
| r21 = | ∞ | d21 = | 10.000 | n14 = 1.51633 | v14 = 64.1 |
| r22 = | ∞ | d22 = | 1.000 | n15 = 1.8061 | v15 = 40.9 |
| r23 = | −39.1240 | d23 = | 0.300 | | |
| r24 = | 23.4978 | d24 = | 6.670 | n16 = 1.85026 | v16 = 32.2 |
| r25 = | 8.5520 | d25 = | 37.730 | n17 = 1.51633 | v17 = 64.1 |
| r26 = | −18.1763 | d26 = | 10.000 | | |
| r27 = | 18.1763 | d27 = | 37.730 | n18 = 1.51633 | v18 = 64.1 |
| r28 = | −8.5520 | d28 = | 6.670 | n19 = 1.85026 | v19 = 32.2 |
| r29 = | −23.4978 | d29 = | 0.300 | | |
| r30 = | 39.1240 | d30 = | 1.000 | n20 = 1.8061 | v20 = 40.9 |
| r31 = | ∞ | d31 = | 10.000 | n21 = 1.51633 | v21 = 64.1 |
| r32 = | ∞ | d32 = | 1.000 | n22 = 1.8061 | v22 = 40.9 |
| r33 = | −39.1240 | d33 = | 0.300 | | |
| r34 = | 23.4978 | d34 = | 6.670 | n23 = 1.85026 | v23 = 32.2 |
| r35 = | 8.5520 | d35 = | 37.730 | n24 = 1.51633 | v24 = 64.1 |
| r36 = | −18.1763 | d36 = | 10.000 | | |
| r37 = | 18.1763 | d37 = | 37.730 | n25 = 1.51633 | v25 = 64.1 |
| r38 = | −8.5520 | d38 = | 6.670 | n26 = 1.85026 | v26 = 32.2 |
| r39 = | −23.4978 | d39 = | 0.300 | | |
| r40 = | 39.1240 | d40 = | 1.000 | n27 = 1.8061 | v27 = 40.9 |
| r41 = | ∞ | d41 = | 10.000 | n28 = 1.51633 | v28 = 64.1 |
| r42 = | ∞ | d42 = | 1.000 | n29 = 1.8061 | v29 = 40.9 |
| r43 = | −39.1240 | d43 = | 0.300 | | |
| r44 = | 23.4978 | d44 = | 6.670 | n30 = 1.85026 | v30 = 32.2 |
| r45 = | 8.5520 | d45 = | 37.730 | n31 = 1.51633 | v31 = 64.1 |
| r46 = | −18.1763 | d46 = | 15.000 | | |
| r47 = | −15.9408 | d47 = | 7.000 | n32 = 1.816 | v32 = 46.6 |
| r48 = | −10.5614 | d48 = | 1.898 | | |
| r49 = | 20.0434 | d49 = | 1.000 | n33 = 1.72916 | v33 = 54.7 |
| r50 = | 11.2226 | d50 = | 1.852 | n34 = 1.7552 | v34 = 27.5 |
| r51 = | 8.3607 | d51 = | 6.099 | | |
| r52 = | −24.1926 | d52 = | 3.535 | n35 = 1.5927 | v36 = 35.3 |
| r53 = | 9.6335 | d53 = | 9.958 | n36 = 1.618 | v36 = 63.4 |
| r54 = | −27.0337 | d54 = | 0.300 | | |
| r55 = | 22.5105 | d55 = | 7.000 | n37 = 1.72916 | v37 = 54.7 |
| r56 = | 317.0029 | d56 = | 102.172 | | |
| r57 = ∞ (image position) | | | | | |

TABLE 5

Lens data of the sixth embodiment

| | | | | | |
|---|---|---|---|---|---|
| r1 = | ∞ | d1 = | 0.400 | n1 = 1.7682 | v1 = 71.8 |
| r2 = | ∞ | d2 = | 0.300 | | |
| r3 = | 2.5311 | d3 = | 1.000 | n2 = 1.883 | v2 = 40.8 |
| r4 = | 0.6002 | d4 = | 0.483 | | |
| r5 = | ∞ | d5 = | 0.492 | n3 = 1.883 | v3 = 40.8 |
| r6 = | ∞ (pupil) | d6 = | 2.925 | n4 = 1.883 | v4 = 40.8 |
| r7 = | −2.9244 | d7 = | 0.300 | | |
| r8 = | −20.1110 | d8 = | 0.500 | n5 = 1.62004 | v5 = 36.3 |
| r9 = | 10.9637 | d9 = | 0.607 | n6 = 1.788 | v6 = 47.4 |
| r10 = | −6.2777 | d10 = | 0.300 | | |
| r11 = | 6.1192 | d11 = | 1.860 | n7 = 1.618 | v7 = 63.4 |
| r12 = | −1.8981 | d12 = | 0.810 | n8 = 1.84666 | v8 = 23.8 |
| r13 = | −2.7109 | d13 = | 0.302 | | |
| r14 = | −2.2811 | d14 = | 0.400 | n9 = 1.78472 | v9 = 25.7 |
| r15 = | −13.8892 | d15 = | 1.289 | n10 = 1.6968 | v10 = 55.5 |
| r16 = | −5.4300 | d16 = | 7.500 | | |
| r17 = | 18.4228 | d17 = | 37.662 | n11 = 1.51633 | v11 = 64.1 |
| r18 = | −8.3677 | d18 = | 6.665 | n12 = 1.85026 | v12 = 32.3 |
| r19 = | −24.4094 | d19 = | 0.300 | | |
| r20 = | 35.7941 | d20 = | 1.000 | n13 = 1.8061 | v13 = 40.9 |
| r21 = | ∞ | d21 = | 10.000 | n14 = 1.51633 | v14 = 64.1 |
| r22 = | ∞ | d22 = | 1.000 | n15 = 1.8061 | v15 = 40.9 |
| r23 = | −35.7941 | d23 = | 0.300 | | |
| r24 = | 24.4094 | d24 = | 6.665 | n16 = 1.85026 | v16 = 32.3 |
| r25 = | 8.3677 | d25 = | 37.662 | n17 = 1.51633 | v17 = 64.1 |
| r26 = | −18.4228 | d26 = | 10.000 | | |
| r27 = | 18.4228 | d27 = | 37.662 | n18 = 1.51633 | v18 = 64.1 |
| r28 = | −8.3677 | d28 = | 6.665 | n19 = 1.85026 | v19 = 32.3 |
| r29 = | −24.4094 | d29 = | 0.300 | | |
| r30 = | 35.7941 | d30 = | 1.000 | n20 = 1.8061 | v20 = 40.9 |
| r31 = | ∞ | d31 = | 10.000 | n21 = 1.51633 | v21 = 64.1 |
| r32 = | ∞ | d32 = | 1.000 | n22 = 1.8061 | v22 = 40.9 |
| r33 = | −35.7941 | d33 = | 0.300 | | |
| r34 = | 24.4094 | d34 = | 6.665 | n23 = 1.85026 | v23 = 32.3 |
| r35 = | 8.3677 | d35 = | 37.662 | n24 = 1.51633 | v24 = 64.1 |
| r36 = | −18.4228 | d36 = | 10.000 | | |
| r37 = | 18.4228 | d37 = | 37.662 | n25 = 1.51633 | v25 = 64.1 |
| r38 = | −8.3677 | d38 = | 6.665 | n26 = 1.85026 | v26 = 32.3 |
| r39 = | −24.4094 | d39 = | 0.300 | | |
| r40 = | 35.7941 | d40 = | 1.000 | n27 = 1.8061 | v27 = 40.9 |
| r41 = | ∞ | d41 = | 10.000 | n28 = 1.51633 | v28 = 64.1 |
| r42 = | ∞ | d42 = | 1.000 | n29 = 1.8061 | v29 = 40.9 |
| r43 = | −35.7941 | d43 = | 0.300 | | |
| r44 = | 24.4094 | d44 = | 6.665 | n30 = 1.85026 | v30 = 32.3 |
| r45 = | 8.3677 | d45 = | 37.662 | n31 = 1.51633 | v31 = 64.1 |
| r46 = | −18.4228 | d46 = | 5.000 | | |
| r47 = | ∞ | d47 = | 11.000 | | |
| r48 = | −10.3813 | d48 = | 5.655 | n32 = 1.816 | v32 = 46.6 |
| r49 = | −8.8890 | d49 = | 0.483 | | |
| r50 = | 7.4696 | d50 = | 3.769 | n33 = 1.72916 | v33 = 54.7 |
| r51 = | 181.6429 | d51 = | 2.093 | n34 = 1.7552 | v34 = 27.5 |
| r52 = | 4.4460 | d52 = | 3.047 | | |
| r53 = | −30.7603 | d53 = | 1.001 | n35 = 1.5927 | v35 = 35.3 |
| r54 = | 41.5845 | d54 = | 1.706 | n36 = 1.618 | v36 = 63.4 |
| r55 = | −17.8259 | d55 = | 0.342 | | |
| r56 = | 7.9775 | d56 = | 5.749 | n37 = 1.72916 | v37 = 54.7 |
| r57 = | 12.6259 | d57 = | 39.986 | | |
| r58 = ∞ (image position) | | | | | |

TABLE 6

Lens data of the tenth embodiment

| | | | | | |
|---|---|---|---|---|---|
| r1 = | ∞ | d1 = | 0.400 | n1 = 1.7682 | v1 = 71.8 |
| r2 = | ∞ | d2 = | 0.500 | | |
| r3 = | −15.1509 | d3 = | 0.500 | n2 = 1.883 | v2 = 40.8 |
| r4 = | 1.8541 | d4 = | 0.400 | | |
| r5 = | ∞ | d5 = | 1.471 | n3 = 1.8061 | v3 = 40.9 |
| r6 = | ∞ (pupil) | d6 = | 8.000 | n4 = 1.8061 | v4 = 40.9 |
| r7 = | −6.3400 | d7 = | 0.300 | | |
| r8 = | 29.8778 | d8 = | 6.980 | n5 = 1.60311 | v5 = 60.7 |
| r9 = | −76.5455 | d9 = | 2.000 | | |
| r10 = | 11.8863 | d10 = | 12.000 | n6 = 1.60311 | v6 = 60.7 |
| r11 = | −14.2286 | d11 = | 1.000 | n7 = 1.84666 | v7 = 23.8 |

TABLE 6-continued

Lens data of the tenth embodiment

| | | | | | | |
|---|---|---|---|---|---|---|
| r12 = | 6.6719 | d12 = | 1.327 | | | |
| r13 = | 16.2399 | d13 = | 1.000 | n8 = 1.84666 | v8 = 23.8 | |
| r14 = | 6.8781 | d14 = | 2.641 | n9 = 1.60311 | v9 = 60.7 | |
| r15 = | −16.3999 | d15 = | 0.300 | | | |
| r16 = | 9.6243 | d16 = | 2.045 | n10 = 1.72916 | v10 = 54.7 | |
| r17 = | 42.1473 | d17 = | 12.000 | | | |
| r18 = | 20.3224 | d18 = | 28.648 | n11 = 1.51633 | v11 = 64.1 | |
| r19 = | −9.1270 | d19 = | 1.000 | n12 = 1.85026 | v12 = 32.3 | |
| r20 = | −17.5105 | d20 = | 0.300 | | | |
| r21 = | 37.3211 | d21 = | 2.038 | n13 = 1.8061 | v13 = 40.9 | |
| r22 = | ∞ | d22 = | 25.393 | n14 = 1.51633 | v14 = 64.1 | |
| r23 = | ∞ | d23 = | 2.038 | n15 = 1.8061 | v15 = 40.9 | |
| r24 = | −37.3211 | d24 = | 0.300 | | | |
| r25 = | 17.5105 | d25 = | 1.000 | n16 = 1.85026 | v16 = 32.3 | |
| r26 = | 9.1270 | d26 = | 28.648 | n17 = 1.51633 | v17 = 64.1 | |
| r27 = | −20.3224 | d27 = | 14.000 | | | |
| r28 = | 20.3224 | d28 = | 28.648 | n18 = 1.51633 | v18 = 64.1 | |
| r29 = | −9.1270 | d29 = | 1.000 | n19 = 1.85026 | v19 = 32.3 | |
| r30 = | −17.5015 | d30 = | 0.300 | | | |
| r31 = | 37.3211 | d31 = | 2.038 | n20 = 1.8061 | v20 = 40.9 | |
| r32 = | ∞ | d32 = | 25.393 | n21 = 1.51633 | v21 = 64.1 | |
| r33 = | ∞ | d33 = | 2.038 | n22 = 1.8061 | v22 = 40.9 | |
| r34 = | −37.3211 | d34 = | 0.300 | | | |
| r35 = | 17.5105 | d35 = | 1.000 | n23 = 1.85026 | v23 = 32.3 | |
| r36 = | 9.1270 | d36 = | 28.648 | n24 = 1.51633 | v24 = 64.1 | |
| r37 = | −20.3224 | d37 = | 14.000 | | | |
| r38 = | 20.3224 | d38 = | 28.648 | n25 = 1.51633 | v25 = 64.1 | |
| r39 = | −9.1270 | d39 = | 1.000 | n26 = 1.85026 | v26 = 32.3 | |
| r40 = | −17.5105 | d40 = | 0.300 | | | |
| r41 = | 37.3211 | d41 = | 2.038 | n27 = 1.8061 | v27 = 40.9 | |
| r42 = | ∞ | d42 = | 25.393 | n28 = 1.51633 | v28 = 64.1 | |
| r43 = | ∞ | d43 = | 2.038 | n29 = 1.8061 | v29 = 40.9 | |
| r44 = | −37.3211 | d44 = | 0.300 | | | |
| r45 = | 17.5105 | d45 = | 1.000 | n30 = 1.85026 | v30 = 32.3 | |
| r46 = | 9.1270 | d46 = | 28.648 | n31 = 1.51633 | v31 = 64.1 | |
| r47 = | −20.3224 | d47 = | 17.000 | | | |
| r48 = | −14.8821 | d48 = | 2.846 | n32 = 1.72916 | v32 = 54.7 | |
| r49 = | −8.8016 | d49 = | 0.300 | | | |
| r50 = | 15.1352 | d50 = | 4.084 | n33 = 1.618 | v33 = 63.4 | |
| r51 = | −7.3338 | d51 = | 1.000 | n34 = 1.5927 | v34 = 35.3 | |
| r52 = | 9.5056 | d52 = | 4.000 | | | |
| r53 = | −16.8952 | d53 = | 2.000 | n35 = 1.7552 | v35 = 27.5 | |
| r54 = | −13.2379 | d54 = | 2.000 | n36 = 1.72916 | v36 = 54.7 | |
| r55 = | −23.2387 | d55 = | 0.300 | | | |
| r56 = | 22.9913 | d56 = | 2.000 | n37 = 1.816 | v37 = 46.6 | |
| r57 = | 89.7162 | d57 = | 15.000 | | | |
| r58 = | ∞ | d58 = | 6.000 (reflection plane) | | | |
| r59 = | ∞ | d59 = | 4.000 (reflection plane) | | | |
| r60 = | 22.5828 | d60 = | 1.000 | n38 = 1.78472 | v38 = 25.7 | |
| r61 = | 6.1627 | d61 = | 3.276 | n39 = 1.55963 | v39 = 61.2 | |
| r62 = | 9.4965 | d62 = | 1.747 | | | |
| r63 = | 13.6433 | d63 = | 3.041 | n40 = 1.60311 | v40 = 60.7 | |
| r64 = | −11.6980 | d64 = | 29.780 | | | |
| r65 = ∞ (image position) | | | | | | |

TABLE 7

Lens data of the eleventh embodiment

| | | | | | |
|---|---|---|---|---|---|
| r1 = | ∞ | d1 = | 0.400 | n1 = 1.7682 | v1 = 71.8 |
| r2 = | ∞ | d2 = | 0.500 | | |
| r3 = | −27.1944 | d3 = | 0.500 | n2 = 1.883 | v2 = 40.8 |
| r4 = | 1.6149 | d4 = | 0.400 | | |
| r5 = | ∞ | d5 = | 0.648 | n3 = 1.8061 | v3 = 40.9 |
| r6 = | ∞ (pupil) | d6 = | 8.000 | n4 = 1.8061 | v4 = 40.9 |
| r7 = | −5.9410 | d7 = | 0.300 | | |
| r8 = | 34.5218 | d8 = | 1.405 | n5 = 1.60311 | v5 = 60.7 |
| r9 = | −44.4283 | d9 = | 1.636 | | |
| r10 = | 10.5798 | d10 = | 11.910 | n6 = 1.60311 | v6 = 60.7 |
| r11 = | −9.6402 | d11 = | 1.000 | n7 = 1.84666 | v7 = 23.8 |
| r12 = | 5.5533 | d12 = | 1.354 | | |
| r13 = | 16.9402 | d13 = | 1.000 | n8 = 1.84666 | v8 = 23.8 |
| r14 = | 5.6237 | d14 = | 2.054 | n9 = 1.60311 | v9 = 60.7 |
| r15 = | −11.8857 | d15 = | 0.300 | | |

TABLE 7-continued

Lens data of the eleventh embodiment

| | | | | | |
|---|---|---|---|---|---|
| r16 = | 9.6717 | d16 = | 2.054 | n10 = 1.72916 | v10 = 54.7 |
| r17 = | 67.8305 | d17 = | 12.000 | | |
| r18 = | 19.4101 | d18 = | 30.497 | n11 = 1.51633 | v11 = 64.1 |
| r19 = | −9.3708 | d19 = | 1.000 | n12 = 1.85026 | v12 = 32.3 |
| r20 = | −18.4223 | d20 = | 0.300 | | |
| r21 = | 37.3503 | d21 = | 1.000 | n13 = 1.8061 | v13 = 40.9 |
| r22 = | ∞ | d22 = | 29.679 | n14 = 1.51633 | v14 = 64.1 |
| r23 = | ∞ | d23 = | 1.000 | n15 = 1.8061 | v15 = 40.9 |
| r24 = | −37.3503 | d24 = | 0.300 | | |
| r25 = | 18.4223 | d25 = | 1.000 | n16 = 1.85026 | v16 = 32.3 |
| r26 = | 9.3708 | d26 = | 30.497 | n17 = 1.51633 | v17 = 64.1 |
| r27 = | −19.4101 | d27 = | 14.000 | | |
| r28 = | 19.4101 | d28 = | 30.497 | n18 = 1.51633 | v18 = 64.1 |
| r29 = | −9.3708 | d29 = | 1.000 | n19 = 1.85026 | v19 = 32.3 |
| r30 = | −18.4223 | d30 = | 0.300 | | |
| r31 = | 37.3503 | d31 = | 1.000 | n20 = 1.8061 | v20 = 40.9 |
| r32 = | ∞ | d32 = | 29.679 | n21 = 1.51633 | v21 = 64.1 |
| r33 = | ∞ | d33 = | 1.000 | n22 = 1.8061 | v22 = 40.9 |
| r34 = | −37.3503 | d34 = | 0.300 | | |
| r35 = | 18.4223 | d35 = | 1.000 | n23 = 1.85026 | v23 = 32.3 |
| r36 = | 9.3708 | d36 = | 30.497 | n24 = 1.51633 | v24 = 64.1 |
| r37 = | −19.4101 | d37 = | 14.000 | | |
| r38 = | 19.4101 | d38 = | 30.497 | n25 = 1.51633 | v25 = 64.1 |
| r39 = | −9.3708 | d39 = | 1.000 | n26 = 1.85026 | v26 = 32.3 |
| r40 = | −18.4223 | d40 = | 0.300 | | |
| r41 = | 37.3503 | d41 = | 1.000 | n27 = 1.8061 | v27 = 40.9 |
| r42 = | ∞ | d42 = | 29.679 | n28 = 1.51633 | v28 = 64.1 |
| r43 = | ∞ | d43 = | 1.000 | n29 = 1.8061 | v29 = 40.9 |
| r44 = | −37.3503 | d44 = | 0.300 | | |
| r45 = | 18.4223 | d45 = | 1.000 | n30 = 1.85026 | v30 = 32.3 |
| r46 = | 9.3708 | d46 = | 30.497 | n31 = 1.51633 | v31 = 64.1 |
| r47 = | −19.4101 | d47 = | 19.000 | | |
| r48 = | −14.3213 | d48 = | 7.000 | n32 = 1.72916 | v32 = 54.7 |
| r49 = | −11.0960 | d49 = | 0.300 | | |
| r50 = | 33.1140 | d50 = | 1.047 | n33 = 1.618 | v33 = 63.4 |
| r51 = | 9.1082 | d51 = | 7.000 | n34 = 1.5927 | v34 = 35.3 |
| r52 = | 67.5887 | d52 = | 3.277 | | |
| r53 = | −9.9528 | d53 = | 7.000 | n35 = 1.7552 | v35 = 27.5 |
| r54 = | 41.3894 | d54 = | 10.000 | n36 = 1.72916 | v36 = 54.7 |
| r55 = | −19.8178 | d55 = | 3.000 | | |
| r56 = | −63.2683 | d56 = | 7.000 | n37 = 1.816 | v37 = 46.6 |
| r57 = | −41.6536 | d57 = | 6.621 | | |
| r58 = | 20.1426 | d58 = | 2.426 | n38 = 1.51633 | v38 = 64.1 |
| r59 = | −122.3553 | d59 = | 5.000 | n39 = 1.78472 | v39 = 25.7 |
| r60 = | 32.7733 | d60 = | 2.000 | | |
| r61 = | 21.5258 | d61 = | 5.000 | n40 = 1.5725 | v40 = 57.8 |
| r62 = | 563.4090 | d62 = | 36.001 | | |
| r63 = ∞ (image position) | | | | | |

TABLE 8

Lens data of the twelfth embodiment

| | | | | | |
|---|---|---|---|---|---|
| r1 = | ∞ | d1 = | 0.400 | n1 = 1.7682 | v1 = 71.8 |
| r2 = | ∞ | d2 = | 0.500 | | |
| r3 = | −5.6176 | d3 = | 8.000 | n2 = 1.883 | v2 = 40.8 |
| r4 = | ∞ (pupil) | d4 = | 8.000 | n3 = 1.883 | v3 = 40.8 |
| r5 = | −10.6525 | d5 = | 1.727 | | |
| r6 = | 225.1706 | d6 = | 1.024 | n4 = 1.60311 | v4 = 60.7 |
| r7 = | 794.5057 | d7 = | 0.803 | | |
| r8 = | 7.7627 | d8 = | 3.448 | n5 = 1.6968 | v5 = 55.5 |
| r9 = | 7.0551 | d9 = | 1.200 | n6 = 1.84666 | v6 = 23.8 |
| r10 = | 6.6689 | d10 = | 1.754 | | |
| r11 = | 21.0094 | d11 = | 1.000 | n7 = 1.84666 | v7 = 23.8 |
| r12 = | 5.2971 | d12 = | 3.637 | n8 = 1.60311 | v8 = 60.7 |
| r13 = | −17.1652 | d13 = | 0.300 | | |
| r14 = | 9.0345 | d14 = | 2.401 | n9 = 1.72916 | v9 = 54.7 |
| r15 = | 40.5646 | d15 = | 12.000 | | |
| r16 = | 19.9468 | d16 = | 30.262 | n10 = 1.51633 | v10 = 64.1 |
| r17 = | −9.0769 | d17 = | 1.018 | n11 = 1.85026 | v11 = 32.3 |
| r18 = | −18.5715 | d18 = | 0.300 | | |
| r19 = | 34.7626 | d19 = | 3.093 | n12 = 1.8061 | v12 = 40.9 |
| r20 = | ∞ | d20 = | 19.606 | n13 = 1.51633 | v13 = 64.1 |
| r21 = | ∞ | d21 = | 3.093 | n14 = 1.8061 | v14 = 40.9 |

TABLE 8-continued

Lens data of the twelfth embodiment

| | | | |
|---|---|---|---|
| r22 = −34.7626 | d22 = 0.300 | | |
| r23 = 18.5715 | d23 = 1.018 | n15 = 1.85026 | v15 = 32.3 |
| r24 = 9.0769 | d24 = 30.262 | n16 = 1.51633 | v16 = 64.1 |
| r25 = −19.9468 | d25 = 14.000 | | |
| r26 = 19.9468 | d26 = 30.262 | n17 = 1.51633 | v17 = 64.1 |
| r27 = −9.0769 | d27 = 1.018 | n18 = 1.85026 | v18 = 32.3 |
| r28 = −18.5715 | d28 = 0.300 | | |
| r29 = 34.7626 | d29 = 3.093 | n19 = 1.8061 | v19 = 40.9 |
| r30 = ∞ | d30 = 19.606 | n20 = 1.51633 | v20 = 64.1 |
| r31 = ∞ | d31 = 3.093 | n21 = 1.8061 | v21 = 40.9 |
| r32 = −34.7626 | d32 = 0.300 | | |
| r33 = 18.5715 | d33 = 1.018 | n22 = 1.85026 | v22 = 32.3 |
| r34 = 9.0769 | d34 = 30.262 | n23 = 1.51633 | v23 = 64.1 |
| r35 = −19.9468 | d35 = 14.000 | | |
| r36 = 19.9468 | d36 = 30.262 | n24 = 1.51633 | v24 = 64.1 |
| r37 = −9.0769 | d37 = 1.018 | n25 = 1.85026 | v25 = 32.3 |
| r38 = −18.5715 | d38 = 0.300 | | |
| r39 = 34.7626 | d39 = 3.093 | n26 = 1.8061 | v26 = 40.9 |
| r40 = ∞ | d40 = 19.606 | n27 = 1.51633 | v27 = 64.1 |
| r41 = ∞ | d41 = 3.093 | n28 = 1.8061 | v28 = 40.9 |
| r42 = −34.7626 | d42 = 0.300 | | |
| r43 = 18.5715 | d43 = 1.018 | n29 = 1.85026 | v29 = 32.3 |
| r44 = 9.0769 | d42 = 30.262 | n30 = 1.51633 | v30 = 64.1 |
| r45 = −19.9468 | d45 = 19.000 | | |
| r46 = −11.8408 | d46 = 5.820 | n31 = 1.72916 | v31 = 54.7 |
| r47 = −9.1946 | d47 = 0.300 | | |
| r48 = 24.0775 | d48 = 10.000 | n32 = 1.618 | v32 = 63.4 |
| r49 = −26.2109 | d49 = 7.000 | n33 = 1.5927 | v33 = 35.3 |
| r50 = 63.4749 | d50 = 3.000 | | |
| r51 = −8.3204 | d51 = 5.376 | n34 = 1.7552 | v34 = 27.5 |
| r52 = −38.8722 | d52 = 10.000 | n35 = 1.72916 | v35 = 54.7 |
| r53 = −19.1304 | d53 = 3.000 | | |
| r54 = −83.1506 | d54 = 7.000 | n36 = 1.816 | v36 = 46.6 |
| r55 = −41.8244 | d55 = 8.346 | | |
| r56 = −26.1283 | d56 = 4.325 | n37 = 1.51633 | v37 = 64.1 |
| r57 = −7.8805 | d57 = 4.552 | n38 = 1.78472 | v38 = 25.7 |
| r58 = −14.4880 | d58 = 0.300 | | |
| r59 = 31.7804 | d59 = 5.000 | n39 = 1.5725 | v39 = 57.8 |
| r60 = 6326.3883 | d60 = 36.032 | | |
| r61 = ∞ (image position) | | | |

TABLE 9

Lens data of the thirteenth embodiment

| | | | |
|---|---|---|---|
| r1 = ∞ | d1 = 0.400 | n1 = 1.7682 | v1 = 71.8 |
| r2 = ∞ | d2 = 0.500 | | |
| r3 = 14.7408 | d3 = 0.500 | n2 = 1.883 | v2 = 40.8 |
| r4 = 1.5441 | d4 = 0.400 | | |
| r5 = ∞ | d5 = 0.572 | n3 = 1.8061 | v3 = 40.9 |
| r6 = ∞ (pupil) | d6 = 7.966 | n4 = 1.8061 | v4 = 40.9 |
| r7 = −5.9996 | d7 = 0.300 | | |
| r8 = 38.8172 | d8 = 1.360 | n5 = 1.60311 | v5 = 60.7 |
| r9 = −54.0250 | d9 = 1.040 | | |
| r10 = 10.8354 | d10 = 11.720 | n6 = 1.60311 | v6 = 60.7 |
| r11 = −36.1554 | d11 = 1.000 | n7 = 1.84666 | v7 = 23.8 |
| r12 = 5.7085 | d12 = 1.444 | | |
| r13 = 17.6383 | d13 = 1.000 | n8 = 1.84666 | v8 = 23.8 |
| r14 = 5.3388 | d14 = 3.339 | n9 = 1.60311 | v9 = 60.7 |
| r15 = −10.4808 | d15 = 0.300 | | |
| r16 = 10.4139 | d16 = 2.316 | n10 = 1.72916 | v10 = 54.7 |
| r17 = 1299.7086 | d17 = 12.000 | | |
| r18 = 20.9531 | d18 = 28.137 | n11 = 1.51633 | v11 = 64.1 |
| r19 = −9.0377 | d19 = 1.029 | n12 = 1.85026 | v12 = 32.3 |
| r20 = −17.1424 | d20 = 0.300 | | |
| r21 = 37.8341 | d21 = 1.462 | n13 = 1.8061 | v13 = 40.9 |
| r22 = ∞ | d22 = 26.759 | n14 = 1.51633 | v14 = 64.1 |
| r23 = ∞ | d23 = 1.462 | n15 = 1.8061 | v15 = 40.9 |
| r24 = −37.8341 | d24 = 0.300 | | |
| r25 = 17.1424 | d25 = 1.029 | n16 = 1.85026 | v16 = 32.3 |
| r26 = 9.0377 | d26 = 28.137 | n17 = 1.51633 | v17 = 64.1 |
| r27 = −20.9531 | d27 = 14.000 | | |
| r28 = 20.9531 | d28 = 28.137 | n18 = 1.51633 | v18 = 64.1 |
| r29 = −9.0377 | d29 = 1.029 | n19 = 1.85026 | v19 = 32.3 |

TABLE 9-continued

Lens data of the thirteenth embodiment

| | | | |
|---|---|---|---|
| r30 = −17.1424 | d30 = 0.300 | | |
| r31 = 37.8341 | d31 = 1.462 | n20 = 1.8061 | v20 = 40.9 |
| r32 = ∞ | d32 = 26.759 | n21 = 1.51633 | v21 = 64.1 |
| r33 = ∞ | d33 = 1.462 | n22 = 1.8061 | v22 = 40.9 |
| r34 = −37.8341 | d34 = 0.300 | | |
| r35 = 17.1424 | d35 = 1.029 | n23 = 1.85026 | v23 = 32.3 |
| r36 = 9.0377 | d36 = 28.137 | n24 = 1.51633 | v24 = 64.1 |
| r37 = −20.9531 | d37 = 14.000 | | |
| r38 = 20.9531 | d38 = 28.137 | n25 = 1.51633 | v25 = 64.1 |
| r39 = −9.0377 | d39 = 1.029 | n26 = 1.85026 | v26 = 32.3 |
| r40 = −17.1424 | d40 = 0.300 | | |
| r41 = 37.8341 | d41 = 1.462 | n27 = 1.8061 | v27 = 40.9 |
| r42 = ∞ | d42 = 26.759 | n28 = 1.51633 | v28 = 64.1 |
| r43 = ∞ | d43 = 1.462 | n29 = 1.8061 | v29 = 40.9 |
| r44 = −37.8341 | d44 = 0.300 | | |
| r45 = 17.1424 | d45 = 1.029 | n30 = 1.85026 | v30 = 32.3 |
| r46 = 9.0377 | d46 = 28.137 | n31 = 1.51633 | v31 = 64.1 |
| r47 = −20.9531 | d47 = 19.000 | | |
| r48 = −13.4332 | d48 = 7.000 | n32 = 1.72916 | v32 = 54.7 |
| r49 = −11.0047 | d49 = 0.300 | | |
| r50 = 17.1878 | d50 = 5.837 | n33 = 1.618 | v33 = 63.4 |
| r51 = 57.8341 | d51 = 7.000 | n34 = 1.5927 | v34 = 35.3 |
| r52 = 38.7072 | d52 = 4.174 | | |
| r53 = −8.1955 | d53 = 6.919 | n35 = 1.7552 | v35 = 27.5 |
| r54 = 42.2429 | d54 = 10.000 | n36 = 1.72916 | v36 = 54.7 |
| r55 = 19.4465 | d55 = 0.300 | | |
| r56 = 944.8567 | d56 = 4.699 | n37 = 1.816 | v37 = 46.6 |
| r57 = −50.3836 | d57 = 18.931 | | |
| r58 = 136.6914 | d58 = 5.000 | n38 = 1.51633 | v38 = 64.1 |
| r59 = −21.5686 | d59 = 5.000 | n39 = 1.78472 | v39 = 25.7 |
| r60 = −47.7722 | d60 = 3.000 | | |
| r61 = 24.4617 | d61 = 5.000 | n40 = 1.5725 | v40 = 57.8 |
| r62 = 207.2457 | d62 = 24.000 | | |
| r63 = ∞ (image position) | | | |

TABLE 10

Lens data of the twenty third embodiment

| | | | |
|---|---|---|---|
| r1 = ∞ | d1 = 0.4 | n1 = 1.769000 | v1 = 71.8 |
| r2 = ∞ | d2 = 0.3 | | |
| r3 = ∞ | d3 = 0.5 | n2 = 1.784720 | v2 = 25.8 |
| r4 = 2.18120 | d4 = 0.8 | | |
| r5 = ∞ | d5 = 6.524779 | n3 = 1.806098 | v3 = 40.9 |
| r6 = ∞ | d6 = 0.000000 | n4 = 1.806098 | v4 = 40.9 |
| r7 = ∞ | d7 = 10.000000 | n5 = 1.806098 | v5 = 40.9 |
| r8 = −18.90821 | d8 = 2.000000 | | |
| r9 = 11.34978 | d9 = 7.000000 | n6 = 1.589130 | v6 = 61.2 |
| r10 = −6.85269 | d10 = 7.000000 | n7 = 1.784718 | v7 = 25.7 |
| r11 = −9.21315 | d11 = 1.757525 | | |
| r12 = −5.83605 | d12 = 1.329338 | n8 = 1.784718 | v8 = 25.7 |
| r13 = 21.54459 | d13 = 5.000000 | n9 = 1.772499 | v9 = 49.6 |
| r14 = −9.87710 | d14 = 0.300000 | | |
| r15 = 23.34659 | d15 = 5.000000 | n10 = 1.729157 | v10 = 54.7 |
| r16 = −46.95906 | d16 = 9.832604 | | |

TABLE 11

Lens data of the twenty fourth embodiment

| | | | |
|---|---|---|---|
| r1 = ∞ | d1 = 0.4 | n1 = 1.769000 | v1 = 71.8 |
| r2 = ∞ | d2 = 0.3 | | |
| r3 = ∞ | d3 = 0.5 | n2 = 1.784720 | v2 = 25.8 |
| r4 = 2.24795 | d4 = 0.8 | | |
| r5 = ∞ | d5 = 26.000000 | n3 = 1.806098 | v3 = 40.9 |
| r6 = ∞ | d6 = 0.000000 | n4 = 1.806098 | v4 = 40.9 |
| r7 = ∞ | d7 = 28.856575 | n5 = 1.806098 | v5 = 40.9 |
| r8 = −36.97230 | d8 = 15.000000 | | |
| r9 = 10.27055 | d9 = 13.872951 | n6 = 1.496999 | v6 = 31.6 |
| r10 = −6.76542 | d10 = 8.669330 | n7 = 1.846660 | v7 = 23.8 |
| r11 = −12.08426 | d11 = 4.358284 | | |
| r12 = −6.61021 | d12 = 3.807170 | n8 = 1.846660 | v8 = 23.8 |

TABLE 11-continued

Lens data of the twenty fourth embodiment

| | | | |
|---|---|---|---|
| r13 = −10.66959 | d13 = 4.004968 | n9 = 1.772499 | ν9 = 49.6 |
| r14 = −10.95412 | d14 = 3.679284 | | |
| r15 = −13.63092 | d15 = 8.940710 | n10 = 1.729157 | ν10 = 54.7 |
| r16 = −11.40751 | d16 = 9.956806 | | |
| r17 = 18.08889 | d17 = 37.945337 | n11 = 1.516330 | ν11 = 64.1 |
| r18 = −8.56598 | d18 = 6.671087 | n12 = 1.850259 | ν12 = 32.3 |
| r19 = −23.41526 | d19 = 0.300000 | | |
| r20 = 39.63203 | d20 = 1.000000 | n13 = 1.806098 | ν13 = 40.9 |
| r21 = ∞ | d21 = 5.000000 | n14 = 1.516330 | ν14 = 64.1 |
| r22 = ∞ | d22 = 5.000000 | n15 = 1.516330 | ν15 = 64.1 |
| r23 = ∞ | d22 = 1.000000 | n16 = 1.806098 | ν15 = 40.9 |
| r24 = −39.63203 | d23 = 0.300000 | | |
| r25 = 23.41526 | d25 = 6.671087 | n17 = 1.850259 | ν17 = 32.3 |
| r26 = 8.56598 | d26 = 37.945337 | n18 = 1.516330 | ν18 = 64.1 |
| r27 = −18.08889 | d27 = 10.000000 | | |
| r28 = 18.08889 | d28 = 37.945337 | n19 = 1.516330 | ν19 = 64.1 |
| r29 = −8.56598 | d29 = 6.671087 | n20 = 1.850259 | ν20 = 32.3 |
| r30 = −23.41526 | d30 = 0.300000 | | |
| r31 = 39.63203 | d31 = 1.000000 | n21 = 1.806098 | ν21 = 40.9 |
| r32 = ∞ | d32 = 5.000000 | n22 = 1.516330 | ν22 = 64.1 |
| r33 = ∞ | d33 = 5.000000 | n21 = 1.516330 | ν21 = 64.1 |
| r34 = ∞ | d34 = 1.000000 | n22 = 1.806098 | ν22 = 40.9 |
| r35 = −39.63203 | d35 = 0.300000 | | |
| r36 = 23.41526 | d36 = 6.671087 | n25 = 1.850259 | ν25 = 32.3 |
| r37 = 8.56598 | d37 = 37.945337 | n26 = 1.516330 | ν26 = 64.1 |
| r38 = −18.08889 | d38 = 10.000000 | | |
| r39 = 18.08889 | d39 = 37.945337 | n27 = 1.516330 | ν27 = 64.1 |
| r40 = −8.56598 | d40 = 6.671087 | n28 = 1.850259 | ν28 = 32.3 |
| r41 = −23.41526 | d41 = 0.300000 | | |
| r42 = 39.63203 | d42 = 1.000000 | n29 = 1.806098 | ν29 = 40.9 |
| r43 = ∞ | d43 = 5.000000 | n30 = 1.516330 | ν30 = 64.1 |
| r44 = ∞ | d44 = 5.000000 | n31 = 1.516330 | ν31 = 64.1 |
| r45 = ∞ | d45 = 1.000000 | n32 = 1.806098 | ν32 = 40.9 |
| r46 = −39.63203 | d46 = 0.300000 | | |
| r47 = 23.41526 | d47 = 6.671087 | n33 = 1.850259 | ν33 = 32.3 |
| r48 = 8.56598 | d47 = 37.945337 | n34 = 1.516330 | ν34 = 64.1 |
| r49 = −18.08889 | d49 = 15.000000 | | |
| r50 = −15.76035 | d50 = 7.000000 | n35 = 1.816000 | ν35 = 46.6 |
| r51 = 10.49216 | d51 = 0.300000 | | |
| r52 = 19.16924 | d52 = 1.000000 | n36 = 1.729157 | ν36 = 54.7 |
| r53 = 10.37555 | d53 = 1.000000 | n37 = 1.755199 | ν37 = 27.5 |
| r54 = 8.20791 | d54 = 6.363656 | | |
| r55 = −24.61446 | d55 = 3.366619 | n38 = 1.592701 | ν38 = 35.3 |
| r56 = 9.99541 | d56 = 9.925109 | n39 = 1.618000 | ν39 = 63.4 |
| r57 = −27.28005 | d57 = 0.547138 | | |
| r58 = 22.89857 | d58 = 7.000000 | n40 = 1.729157 | ν40 = 54.7 |
| r59 = 465.13444 | d59 = 100.501554 | | |

TABLE 12

Lens data of the twenty fifth embodiment

| R | D | N | ν |
|---|---|---|---|
| r1 = ∞ | d1 = 0.400000 | n1 = 1.769000 | ν1 = 71.8 |
| r2 = ∞ | d2 = 0.300000 | | |
| r3 = −5.97394 | d3 = 0.500000 | n2 = 1.784720 | ν2 = 25.8 |
| r4 = −81.88587 | d4 = 0.400000 | | |
| r5 = ∞ | d5 = 7.000000 | n3 = 1.806098 | ν3 = 40.9 |
| r6 = ∞ | d6 = 0.000000 | n4 = 1.806098 | ν4 = 40.9 |
| r7 = ∞ | d7 = 5.000000 | n5 = 1.806098 | ν5 = 40.9 |
| r8 = −19.02807 | d8 = 0.300000 | | |
| r9 = 19.68776 | d9 = 1.500000 | n6 = 1.603112 | ν6 = 60.7 |
| r10 = −143.32901 | d10 = 0.300000 | | |
| r11 = 8.84976 | d11 = 2.000000 | n7 = 1.603112 | ν7 = 60.7 |
| r12 = 205.54794 | d12 = 2.000000 | n8 = 1.846660 | ν8 = 23.8 |
| r13 = 7.54926 | d13 = 3.000000 | | |
| r14 = 11.00667 | d14 = 3.000000 | n9 = 1.846660 | ν9 = 23.8 |
| r15 = 6.70344 | d15 = 2.697123 | n10 = 1.603112 | ν10 = 60.7 |
| r16 = −29.22995 | d16 = 0.300000 | | |
| r17 = 25.03133 | d17 = 5.000000 | n11 = 1.729157 | ν11 = 54.7 |
| r18 = −19.09934 | d18 = 14.067359 | | |
| r19 = 20.97714 | d19 = 31.002854 | n12 = 1.516330 | ν12 = 64.1 |
| r20 = −9.61884 | d20 = 1.000000 | n13 = 1.850259 | ν13 = 32.3 |

TABLE 12-continued

Lens data of the twenty fifth embodiment

| R | D | N | ν |
|---|---|---|---|
| r21 = −18.35394 | d21 = 0.300000 | | |
| r22 = 39.59182 | d22 = 1.000000 | n14 = 1.806098 | ν14 = 40.9 |
| r23 = ∞ | d23 = 12.733214 | n15 = 1.516330 | ν15 = 64.1 |
| r24 = ∞ | d24 = 12.733214 | n16 = 1.516330 | ν16 = 64.1 |
| r25 = ∞ | d25 = 1.000000 | n17 = 1.806098 | ν17 = 40.9 |
| r26 = −39.59182 | d26 = 0.300000 | | |
| r27 = 18.35394 | d27 = 1.000000 | n18 = 1.850259 | ν18 = 32.3 |
| r28 = 9.61884 | d28 = 31.002854 | n19 = 1.516330 | ν19 = 64.1 |
| r29 = −20.97714 | d29 = 13.999522 | | |
| r30 = 20.97714 | d30 = 31.002854 | n20 = 1.516330 | ν20 = 64.1 |
| r31 = −9.61884 | d31 = 1.000000 | n21 = 1.850259 | ν21 = 32.3 |
| r32 = 18.35394 | d32 = 0.300000 | | |
| r33 = 39.59182 | d33 = 1.000000 | n22 = 1.806098 | ν22 = 40.9 |
| r34 = ∞ | d34 = 12.733214 | n23 = 1.516330 | ν23 = 64.1 |
| r35 = ∞ | d35 = 12.733214 | n24 = 1.516330 | ν24 = 64.1 |
| r36 = ∞ | d36 = 1.000000 | n25 = 1.806098 | ν25 = 40.9 |
| r37 = −39.59182 | d37 = 0.300000 | | |
| r38 = 18.35394 | d38 = 1.000000 | n26 = 1.850259 | ν26 = 32.3 |
| r39 = 9.61884 | d39 = −31.002854 | n27 = 1.516330 | ν27 = 64.1 |
| r40 = −20.97714 | d40 = 22.951000 | | |
| r41 = 51.24000 | d41 = 4.900000 | n28 = 1.712995 | ν28 = 53.9 |
| r42 = −30.80800 | d42 = 0.350000 | | |
| r43 = 15.16600 | d43 = 4.930000 | n29 = 1.617001 | ν29 = 62.8 |
| r44 = 47.26000 | d44 = 1.650000 | n30 = 1.592701 | ν30 = 35.3 |
| r45 = 10.61000 | d45 = 7.000000 | | |
| r46 = −8.87100 | d46 = 2.070000 | n31 = 1.755199 | ν31 = 27.5 |
| r47 = −42.79500 | d47 = 7.380000 | n32 = 1.696800 | ν32 = 56.5 |
| r48 = −13.94800 | d48 = 0.480000 | | |
| r49 = ∞ | d49 = 4.700000 | n33 = 1.804000 | ν34 = 46.6 |
| r50 = −45.75100 | d50 = 8.660000 | | |
| r51 = 47.10400 | d51 = 3.500000 | n34 = 1.516330 | ν34 = 64.1 |
| r52 = −22.01500 | d52 = 1.500000 | n35 = 1.784718 | ν35 = 25.7 |
| r53 = −48.13700 | d53 = 1.000000 | | |
| r54 = 79.15800 | d54 = 3.000000 | n36 = 1.572501 | ν36 = 57.8 |
| r55 = −79.15800 | d55 = 32.098487 | | |

TABLE 13

Lens data of the twenty sixth embodiment

| | | | |
|---|---|---|---|
| r1 = ∞ | d1 = 1.0 | n1 = 1.51633 | ν1 = 64.15 |
| r2 = ∞ | d2 = 0.3 | | |
| r3 = ∞ | d3 = 1.5 | n2 = 1.72916 | ν2 = 54.68 |
| r4 = 4.4560 | d4 = 2.5 | | |
| r5 = ∞ | d5 = 22.02 | n3 = 1.88300 | ν3 = 40.78 |
| r6 = ∞ (pupil) | d6 = 5.39 | n4 = 1.88300 | ν4 = 40.78 |
| r7 = −10.3990 | d7 = 1.02 | | |
| r8 = −8.6190 | d8 = 2.0 | n5 = 1.62004 | ν5 = 36.25 |
| r9 = ∞ | d9 = 3.5 | n6 = 1.788 | ν6 = 47.38 |
| r10 = −14.1680 | d10 = 2.28 | | |
| r11 = 24.1810 | d11 = 6.14 | n7 = 1.51633 | ν7 = 64.15 |
| r12 = −11.7470 | d12 = 3.0 | n8 = 1.78472 | ν8 = 25.71 |
| r13 = ∞ | d13 = 8.65 | | |
| r14 = 38.2890 | d14 = 3.0 | n9 = 1.59551 | ν9 = 39.21 |
| r15 = 11.4220 | d15 = 6.0 | n10 = 1.51633 | ν10 = 64.15 |
| r16 = −19.2720 | d16 = 10.0 | | |

TABLE 14

Lens data of the twenty seventh embodiment

| | | | |
|---|---|---|---|
| r1 = ∞ | d1 = 0.4 | n1 = 1.7682 | ν1 = 71.8 |
| r2 = ∞ | d2 = 0.5 | | |
| r3 = −12.44196 | d3 = 0.5 | n2 = 1.883 | ν2 = 40.8 |
| r4 = 3.50665 | d4 = 0.4 | | |
| r5 = ∞ | d5 = 7.0 | n3 = 1.80610 | ν3 = 40.9 |
| r6 = ∞ (pupil) | d6 = 7.0 | n4 = 1.80610 | ν4 = 40.9 |
| r7 = −9.32306 | d7 = 0.3 | | |
| r8 = 24.40418 | d8 = 1.3301 | n5 = 1.60311 | ν5 = 60.7 |
| r9 = −51.70650 | d9 = 0.8047 | | |

TABLE 14-continued

Lens data of the twenty seventh embodiment

| | | | |
|---|---|---|---|
| r10 = 10.49630 | d10 = 10.0 | n6 = 1.60311 | v6 = 60.7 |
| r11 = −12.17332 | d11 = 1.0 | n7 = 1.84666 | v7 = 23.8 |
| r12 = 5.56286 | d12 = 1.7183 | | |
| r13 = −11.69704 | d13 = 1.0 | n8 = 1.84666 | v8 = 23.8 |
| r14 = −221.94536 | d14 = 2.1568 | n9 = 1.60311 | v9 = 60.7 |
| r15 = −8.24002 | d15 = 0.3 | | |
| r16 = 10.31164 | d16 = 2.3746 | n10 = 1.72916 | v10 = 54.7 |
| r17 = −30.38097 | d17 = 12.0 | | |
| r18 = 20.97714 | d18 = 31.0029 | n11 = 1.51633 | v11 = 64.1 |
| r19 = −9.61884 | d19 = 1.0 | n12 = 1.85026 | v12 = 32.3 |
| r20 = −18.35394 | d20 = 0.3 | | |
| r21 = 39.59182 | d21 = 1.0 | n13 = 1.8061 | v13 = 40.9 |
| r22 = ∞ | d22 = 25.4664 | n14 = 1.51633 | v14 = 64.1 |
| r23 = ∞ | d22 = 1.0 | n15 = 1.8061 | v15 = 40.9 |
| r24 = −39.59182 | d23 = 0.3 | | |
| r25 = 18.35394 | d25 = 1.0 | n16 = 1.85026 | v16 = 32.3 |
| r26 = 9.61884 | d26 = 31.0029 | n17 = 1.51633 | v17 = 64.1 |
| r27 = −20.97714 | d27 = 13.9995 | | |
| r28 = 20.97714 | d28 = 31.0029 | n18 = 1.51633 | v18 = 64.1 |
| r29 = −9.61884 | d29 = 1.0 | n19 = 1.85026 | v19 = 32.3 |
| r30 = −18.35394 | d30 = 0.3 | | |
| r31 = 39.59182 | d31 = 1.0 | n20 = 1.8061 | v20 = 40.9 |
| r32 = ∞ | d32 = 25.4664 | n21 = 1.51633 | v21 = 64.1 |
| r33 = ∞ | d33 = 1.0 | n22 = 1.8061 | v22 = 40.9 |
| r34 = −39.59182 | d34 = 0.3 | | |
| r35 = 18.35394 | d35 = 1.0 | n23 = 1.85026 | v23 ' 32.3 |
| r36 = 9.61884 | d36 = 31.0029 | n24 = 1.51633 | v24 = 64.1 |
| r37 = −20.97714 | d37 = 13.9995 | | |
| r38 = 20.97714 | d38 = 31.0029 | n25 = 1.51633 | v25 = 64.1 |
| r39 = −9.61884 | d39 = 1.0 | n26 = 1.85026 | v26 = 32.3 |
| r40 = −18.35394 | d40 = 0.3 | | |
| r41 = 39.59182 | d41 = 1.0 | n27 = 1.8061 | v27 = 40.9 |
| r42 = ∞ | d42 = 25.4664 | n28 = 1.51633 | v28 = 64.1 |
| r43 = ∞ | d43 = 1.0 | n29 = 1.8061 | v29 = 40.9 |
| r44 = −39.59182 | d44 = 0.3 | | |
| r45 = 18.35394 | d45 = 1.0 | n30 = 1.85026 | v30 = 32.3 |
| r46 = 9.61884 | d46 = 31.0029 | n31 = 1.51633 | v31 = 64.1 |
| r47 = −20.97714 | d47 = 7.004 | | |

What is claimed is:

1. An endoscope comprising:

an elongated inserted section;

an illuminating light projecting means projecting an illuminating light from the distal end side of said insertion section;

an objective optical system arranged on the distal end side of said insertion section, having at least two optical systems having plural pupils receiving the light from an object illuminated by said illuminating light and forming at least two images not equal to each other, said plural pupils being arranged so as not to be superimposed, and one image transmitting optical system arranged within said inserted section and having a single optical axis, transmitting said two images simultaneously, wherein said two optical systems have two optical axes not parallel with each other and form images different in the visual field direction from each other.

2. An endoscope, comprising:

an objective optical system having plural visual field direction s and plural pupils corresponding to the visual field directions, the plural pupils being arranged so as not to be superimposed, and the objective optical system forming at least one object image;

a transmitting optical system for med to be of a size equal to or larger am the size of the plural pupils from the objective optical system and having a single optical axis, transmitting rearward the object image and said plural pupils from said objective optical system simultaneously.

3. An endoscope according to claim 2, further comprising a pupil separating means for separating plural pupils corresponding respectively to beams in different directions and transmitted by said transmitting optical system and an image forming optical system forming object images formed by the beams included in a range of the pupils corresponding to separated respective visual field directions.

4. An endoscope according to claim 3, wherein the pupil separating means is arranged near the plural pupils transmitted by said transmitting optical system on a side on which the rays are projected by said transmitting optical system.

5. An endoscope according to claim 3, further comprising plural image taking means for receiving respectively plural object images formed by said image forming optical system and forming images.

6. An endoscope according to claim 5 wherein said pupil separating means has a reflecting means directing the plural beams separated by an optical member in a direction substantially parallel with the optical axis of said transmitting optical system and said plural image taking means receive the beams reflected by said reflecting means and take respectively the object images formed by said image forming optical system.

7. An endoscope comprising:

an objective optical system, said objective optical system having plural visual field directions and plural pupils corresponding to these visual field directions and formed so as not to be superimposed on each other and forming object images, and a transmitting optical system having a single optical axis and transmitting the object images and plural pupils from said objective optical system simultaneously;

wherein said objective optical system further comprises a front side optical system which receives beams in directions different from each other and projects said beams as plural substantially afocal beams arranged substantially in parallel along the optical axis of said transmitting optical system and a rear side optical system which has a single optical axis common with said transmitting optical system, converges the plural beams from said front side optical system and forms object images rearward, and wherein said image transmitting optical system transmits rearward the object images and plural pupils, and is formed to be of a size equal to or larger than the size of the plural pupils corresponding to the plural beams transmitted from said rear side optical system.

8. An endoscope according to claim 7, further comprising an image forming optical system having an optical axis common with said transmitting optical system and forming an object image formed of the beam included in the range of plural pupils corresponding to the respective visual field directions from said transmitting optical system.

9. An endoscope according to claim 8 wherein said image forming optical system is an ocular optical system forming plural object images corresponding to different visual field directions so as to be observable with the naked eyes.

10. An endoscope according to claim 9 wherein a means setting plural pupils corresponding to the respective beams in said plural different directions is provided in either of said objective optical system and said transmitting optical system.

11. An endoscope according to claim 8 wherein a means setting plural pupils corresponding to the respective beams in said plural different directions is provided in either of said objective optical system and said transmitting optical system.

12. An endoscope comprising an objective optical system having plural visual field directions and plural pupils corresponding to said plural visual field directions; and a transmitting optical system having a single optical axis, wherein said objective optical system comprises a front side optical system including plural pupils receiving respectively plural beams in directions different from each other and a prism optical system varying at least one of said beams and converting the respective beams to beams directed in substantially the same direction and a rear side optical system forming object images made of plural beams from said front side optical system in substantially the same position, and wherein said transmitting optical system transmits rearward the object images and plural pupils from said rear side optical system simultaneously.

13. An endoscope comprising:

an objective optical system having plural visual field directions and plural pupils corresponding to said plural visual field directions, and a transmitting optical system having a single optical axis, wherein said objective optical system has a front side optical system including plural lenses having optical axes in directions different from each other and a prism optical system receiving the respective beams having passed through said plural lenses and converting said beams to plural beams arranged substantially in parallel along the optical axis of said transmitting optical system and a rear side optical system having a size including the beams projected out of said front side optical system and having a single axis and having a convergence for projected rays to simultaneously form images of the plural beams, and wherein said transmitting optical system transmits rearward the object images and plural pupils from said rear side optical system simultaneously.

14. An endoscope according to claim 13 wherein an ocular optical system having an optical axis common with said transmitting optical system is arranged on the proximal side of the transmitting optical system.

15. An endoscope according to claim 13, further comprising a reflecting means directing the plural beams projected out of said optical system in respectively different directions, plural image forming optical systems provided in the respective light paths of the respective beams to form object images of the respective beams reflected by said reflecting means and plural image taking means taking images by receiving the respective object images formed by said image forming optical system.

16. An endoscope comprising:

an objective optical system; and a transmitting optical system, wherein said transmitting optical system has a single optical axis, wherein said objective optical system further comprises a front side optical system including a lens having a negative refractive power and a rear side optical system including a lens having a positive refractive power. and has a convergence, wherein said front side optical system includes plural lenses having optical axes in directions different from each other and a prism receiving beams in directions different from each other and converting said beams to plural beams arranged substantially in parallel with the single optical axis of said transmitting optical system, and wherein said rear side optical system has a size including the beams projected out of said front side optical system, and has a single optical axis. and forms images of objects of said plural beams simultaneously through said transmitting optical system on an image surface.

* * * * *